(12) United States Patent
Kazimtrova et al.

(10) Patent No.: US 9,217,027 B2
(45) Date of Patent: Dec. 22, 2015

(54) THROMBIN INHIBITOR

(75) Inventors: Maria Kazimtrova, Bratislava (SK); R. Manjunatha Kini, Singapore (SG); Cho Yeow Koh, Singapore (SG)

(73) Assignee: Isis Innovation Limited, Oxford (GB)

( * ) Notice: Subject to any disclaimer, the term of this patent is extended or adjusted under 35 U.S.C. 154(b) by 1557 days.

(21) Appl. No.: 12/665,256

(22) PCT Filed: Jun. 18, 2008

(86) PCT No.: PCT/IB2008/002109
§ 371 (c)(1),
(2), (4) Date: Jul. 30, 2010

(87) PCT Pub. No.: WO2008/155658
PCT Pub. Date: Dec. 24, 2008

(65) Prior Publication Data
US 2013/0183237 A1    Jul. 18, 2013

(30) Foreign Application Priority Data

Jun. 18, 2007 (GB) .................................. 0711779.9

(51) Int. Cl.
| | | |
|---|---|---|
| *A61K 51/00* | (2006.01) | |
| *A61M 36/14* | (2006.01) | |
| *G01N 33/53* | (2006.01) | |
| *C12N 15/09* | (2006.01) | |
| *C12N 1/20* | (2006.01) | |
| *C12N 15/00* | (2006.01) | |
| *C12N 9/96* | (2006.01) | |
| *C12N 9/99* | (2006.01) | |
| *A61K 38/57* | (2006.01) | |
| *C07K 14/81* | (2006.01) | |
| *C07K 14/745* | (2006.01) | |
| *A61K 38/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *A61K 38/04* | (2006.01) | |
| *A61K 38/36* | (2006.01) | |
| *A61K 51/08* | (2006.01) | |
| *C07K 7/06* | (2006.01) | |
| *C07K 7/08* | (2006.01) | |
| *C12Q 1/56* | (2006.01) | |

(52) U.S. Cl.
CPC ............... *C07K 14/811* (2013.01); *A61K 38/36* (2013.01); *A61K 38/57* (2013.01); *A61K 51/08* (2013.01); *C07K 7/06* (2013.01); *C07K 7/08* (2013.01); *C12Q 1/56* (2013.01)

(58) Field of Classification Search
USPC ........................................................ 424/1.69
See application file for complete search history.

(56) References Cited

U.S. PATENT DOCUMENTS

| | | |
|---|---|---|
| 5,196,404 A | 3/1993 | Maraganore et al. |
| 6,060,451 A | 5/2000 | DiMaio et al. |

FOREIGN PATENT DOCUMENTS

| | | |
|---|---|---|
| EP | 0276014 A2 | 7/1988 |
| WO | 95/11921 A1 | 5/1995 |
| WO | 96/10638 A1 | 4/1996 |
| WO | 96/30407 A1 | 10/1996 |
| WO | 98/00443 A1 | 1/1998 |
| WO | 98/12318 A1 | 3/1998 |
| WO | 03/091284 A1 | 11/2003 |
| WO | WO 03091284 A1 * | 11/2003 |
| WO | 2004/076484 A1 | 9/2004 |
| WO | 2008/155658 A2 | 12/2008 |

OTHER PUBLICATIONS

Koh et al. "Variegin, a Novel Fast and Tight Binding Thrombin Inhibitor from the Tropical Bont Tick" J Biol Sci 282:29101-29113. Published Oct. 5, 2007.*
Andreescu et al. "Trousseau's Syndrome Treated with Long-Term Subcutaneous Lepirudin (Case Report and Review of the Literature)" J. Thrombosis and Thrombolysis 11:33-37. Published 2001.*
Varki A "Trousseau's syndrome: multiple definitions and multiple mechanisms" Blood 110:1723-1729. Published online May 11, 2007.*
Blat, Yuval, "Non-Competitive Inhibition by Active Site Binders," Chem. Biol. Drug Des., vol. 75:535-540 (2010).
Bode, Wolfram et al., "The refined 1.9-A X-ray crystal structure of D-Phe-Pro-Arg chloromethylketone-inhibited human alpha-thrombin: Structure analysis, overall structure, electrostatic properties, detailed active-site geometry, and structure-function relationships," Protein Science, vol. 1:426-471 (1992).
Eriksson, Bengt I. et al., "Dabigatran etexilate," Nature Reviews Drug Discovery, vol. 7:557-558 (2008).
Greinacher, Andreas et al., "The direct thrombin inhibitor hirudin," Thromb. Haemost., vol. 99:819-829 (2008).
Koh, Cho Yeow et al., "Noncompetitive Inhibitor of Thrombin," ChemBioChem, vol. 10:2155-2158 (2009).
Otlewski, Jacek et al., "The many faces of protease-protein inhibitor interaction," The EMBO Journal, vol. 24 (7):1303-1310 (2005).
Perona, John J. et al., "Structural basis of substrate specificity in the serine proteases," Protein Science, vol. 4:337-360 (1995).

(Continued)

*Primary Examiner* — Christina Bradley
*Assistant Examiner* — Zachary J Miknis
(74) *Attorney, Agent, or Firm* — Nelson Mullins Riley & Scarborough LLP; Jane E. Remillard, Esq.

(57) ABSTRACT

The invention relates to thrombin inhibitors derived from the salivary glands of haematophagous arthropods and in particular to bivalent and trivalent thrombin inhibitors that act by interacting with thrombin at two or three different sites.

11 Claims, 21 Drawing Sheets

(56) References Cited

OTHER PUBLICATIONS

Figure 1A:
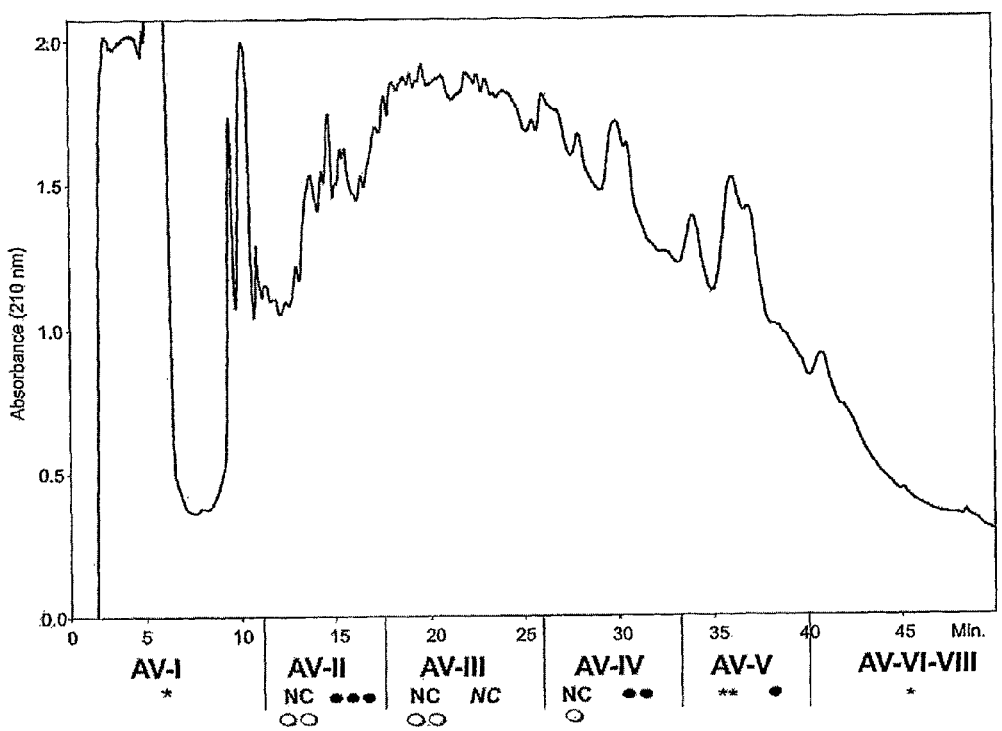

Plotnick, Michael I. et al., "Distortion of the Active Site of Chymotrypsin Complexed with a Serpin," Biochemistry, vol. 35:7586-7590 (1996).

Qiu, Xiayang et al., "Structure of the Hirulog 3-Thrombin Complex and Nature of the S' Subsites of Substrates and Inhibitors," Biochemistry, vol. 31:11689-11697 (1992).

Vindigni, Alessandro et al., "Site-specific dissection of substrate recognition by thrombin," Nature Biotechnology, vol. 15:891-895 (1997).

Warkentin, Theodore E. et al., "Bivalirudin," Thromb. Haemost., vol. 99:830-839 (2008).

Yeh, Robert W. et al., "Argatroban: Update," Am. Heart J., vol. 151:1131-1138 (2006).

Fuentes-Prior, Paglo et al., "Structure of the thrombin complex with triabin, a lipocalin-like exosite-binding inhibitor derived from a triatomine bug," Proc. Natl. Acad. Sci. USA, vol. 94:11845-11850 (1997).

Gieseler, Frank et al., "Activated coagulation factors in human malignant effusions and their contribution to cancer cell metastasis and therapy," Thromb. Haemost., vol. 97:1023-1030 (2007).

Grutter, Markus G. et al., "Crystal structure of the thrombin-hirudin complex: a novel mode of serine protease inhibition," The EMBO Journal, vol. 9(8):2361-2365 (1990).

Gurm, Hitinder, S. et al., "Thrombin, an ideal target for pharmacological inhibition: A review of direct thrombin inhibitors," Am. Heart J., vol. 149:S43-S53 (2005).

Harvey, R.P. et al., "Cloning and expression of a cDNA coding for the anticoagulant hirudin from the bloodsucking leech, *Hirudo medicinalis*," Proc. Natl. Acad. Sci, USA, vol. 83:1084-1088 (1986).

Kazimirova, Maria et al., "Anti-proliferative activity and apoptotic effects of tick salivary gland extracts on human HeLa cells," Neuro Endocrinol Lett., vol. 27(Suppl. 2):48-52 (2006).

Koh, Cho Yeow et al., "Variegin, a Novel Fast and Tight Binding Thrombin Inhibitor from the Tropical Bont Tick," The Journal of Biological Chemistry, vol. 282(40):29101-29113 (2007).

Lehman, Sam J. et al., "Bivalirudin in percutaneous coronary intervention," Vascular Health and Risk Management, vol. 2(4):357-363 (2006).

Lewis, Bruce E. et al., "Direct thrombin inhibition during percutaneous coronary intervention in patients with heparin-induced thrombocytopenia," Expert Rev. Cardiovasc., vol. 5(1):57-68 (2007).

MacLean, Alexandra A. et al., "Bivalirudin in Peripheral Interventions," Techniques in Vascular and Interventional Radiology, vol. 9:80-83 (2006).

Maraganore, J. M. et al., "Design and Characterization of Hirulogs: A Novel Class of Bivalent Peptide Inhibitors of Thrombin," Biochemistry, vol. 29:7095-7101 (1990).

Markwardt, Fritz, "The Development of Hirudin as an Antithrombotic Drug," Thrombosis Research, vol. 74(1):1-23 (1994).

Myles, Timothy et al., "Electrostatic Steering and Ionic Tethering in the Formation of Thrombin-Hirudin Complexes: The Role of the Thrombin Anion-Binding Exosite-I," Biochemistry, vol. 40:4972-4979 (2001).

Naski, Michael C. et al., "The COOH-terminal Domain of Hirudin," The Journal of Biological Chemistry, vol. 265 (23):13484-13489 (1990).

Ni, Feng et al., "Conformational Stability of a Thrombin-Binding Peptide Derived from the Hirudin C-Terminus," Biochemistry, vol. 31:2545-2554 (1992).

Noeske-Jungblut, Christiane et al., "Triabin, a Highly Potent Exosite Inhibitor of Thrombin," The Journal of Biological Chemistry, vol. 270(48):28629-28634 (1995).

Page, M.J. et al., "Determinants of specificity in coagulation proteases," Journal of Thrombosis and Haemostasis, vol. 3:2401-2408 (2005).

Rezaie, Alireza R., "Kinetics of Factor Xa Inhibition by Recombinant Tick Anticoagulant Profile: Both Active Site and Exosite Interactions Are Required for a Slow- and Tight-Binding Inhibition Mechanism," Biochemistry, vol. 43:3368-3375 (2004).

Richardson, John L. et al., "Crystal structure of the human a-thrombin-haemadin complex: an exosite II-binding inhibitor," The EMBO Journal, vol. 19(21):5650-5660 (2000).

Rydel, Timothy J. et al., "Refined Structure of the Hirudin-Thrombin Complex," J. Mol. Biol., vol. 221:583-601 (1991).

Rydel, Timothy J. et al., "The Structure of a Complex of Recombinant Hirudin and Human a-Thrombin," Science, vol. 249:277-280 (1990).

Skrzypczak-Jankun, Ewa et al., "Structure of the Hirugen and Hirulog 1 Complexes of a-Thrombin," J. Mol. Biol., vol. 221:1379-1393 (1991).

Van De Locht, Andreas et al., "The ornithodorin-thrombin crystal structure, a key to the TAP enigma?" The EMBO Journal, vol. 15(22):6011-6017 (1996).

Van De Locht, Andreas et al., "Two heads are better than one: crystal structure of the insect derived double domain Kazal inhibitor rhodniin in complex with thrombin," The EMBO Journal, vol. 14(21):5149-5157 (1995).

Watson, Kristin et al., "Comparison of Patient Outcomes with Bivalirudin versus Unfractionated Heparin in Percutaneous Coronary Intervention," Pharmacotherapy, vol. 27(5):647-656 (2007).

Witting, Joyce I. et al., "Thrombin-specific inhibition by and slow cleavage of hirulog-1," Biochem. J., vol. 283:737-743 (1992).

\* cited by examiner

Level 1

Level 2

Level 3

Level 4

Level 5

THROMBIN INHIBITOR

The present invention relates to thrombin inhibitors derived from the salivary glands of haematophagous arthropods and in particular to bivalent and trivalent thrombin inhibitors that act by interacting with thrombin at two or three different sites.

All documents mentioned in the text and listed at the end of this description are incorporated herein by reference.

Blood coagulation is part of the physiological response to vascular injury, in which circulating zymogens of serine proteases are sequentially activated by limited proteolysis leading to the formation of fibrin clot. Within this network of reactions, thrombin plays a central role in maintaining the integrity of hemostasis. Thrombin interacts with most of the zymogens and their cofactors, playing multiple procoagulant and anticoagulant roles in blood coagulation[1,2]. As a procoagulant protease, the first traces of thrombin generated in the initiation phase activate factor V (FV) and factor VIII (FVIII) to provide positive feedback leading to thrombin burst. Thrombin can also activate factor XI, triggering the intrinsic pathway. Thrombin cleaves fibrinogen to fibrin, forming insoluble clots. Fibrin polymers are further strengthened and stabilized through covalent cross-linking driven by thrombin activated factor XIII. Thrombin also contributes to the generation of a platelet plug, possibly through two mechanisms: (a) it activates platelets by interacting with protease-activated receptors (PARs) and glycoprotein V; and (b) it prevents destabilization of the platelet plug, by inactivating ADAMTS13, a disintegrin and metalloprotease with a thrombospondin type 1 motif, that cleaves von Willebrand factor (VWF). As an anticoagulant protease, thrombin activates protein C (APC) in the presence of the cofactor thrombomodulin. APC inactivates factor Va (FVa) and factor VIIIa (FVIIIa), down-regulating the generation of thrombin[1-5].

Thromboembolic disorders are major causes of mortality and morbidity[6]. Anticoagulants are pivotal in the prophylaxis and treatment of these disorders. Although heparin and coumarin derivatives (vitamin K antagonists) are the cornerstones of anticoagulation therapy, both classes of drugs have well-documented limitations, such as a narrow therapeutic window and highly variable dose-response. These limitations drive the continual and intense effort to develop new anticoagulants, mainly targeting specific coagulation factors[7]. Thrombin represents a good target owing to its central role in the coagulation cascade[6,8].

Thrombin inhibitors such as heparin and its analogues, which have been in widespread therapeutic use for decades, are indirect thrombin inhibitors, that is, they act as part of an antithrombin complex and do not themselves interact directly with the thrombin active site. This means that they can only inactivate soluble thrombin but cannot react with fibrin-bound thrombin. Direct thrombin inhibitors are capable of inactivating both soluble and fibrin-bound thrombin. This confers considerable therapeutic benefits since these agents can inhibit the ongoing coagulation process within the clot itself, not just the formation of new clot (Di Nisio, M., S. Middeldorp, and H. R. Buller. 2005. Direct thrombin inhibitors. N Engl J Med 353: 1028-40).

Some examples of direct thrombin inhibitors include hirudin, hirulog (or bivalirudin) and agratroban[7-9]. Haematophagous animals have developed a rich reservoir of inhibitors for blood coagulation proteases during evolution[16-20] and two known direct thrombin inhibitors, hirudin and hirulog, are derived from a haematophagous animal. Hirudin is a 65-amino acids protein isolated from the salivary gland of medicinal leech *Hirudo medicinalis*[7,8,10]. It has a globular N-terminal domain and an acidic C-terminal tail, both of which bind to sites in the thrombin molecule. This C-terminal tail interacts with thrombin exosite-I through electrostatic and hydrophobic interactions. The N-terminal domain binds to an apolar site near the active site of thrombin, obstructing its accessibility[11-13]. Hirulog (bivalirudin), a 20-mer polypeptide, is a product of rational design by grafting the hirudin C-terminal tail to an active site binding moiety $_D$-Phe-Pro-Arg-Pro using four Gly residues as spacer[14,15]. Unlike hirudin and bivalirudin which are bivalent inhibitors that bind to the exosite I and active site of thrombin, argatroban is a univalent inhibitor and binds only to the active site[8].

The problem with direct thrombin inhibitors that interact with the active site of thrombin, however, is that they may eventually be cleaved by thrombin, resulting in loss of inhibitory activity. There remains a need for more effective direct thrombin inhibitors and, in particular, for thrombin inhibitors that are less likely to lose inhibitory activity as a result of thrombin cleavage.

DESCRIPTION OF THE INVENTION

According to a first aspect of the invention, there is provided a method of inhibiting thrombin activity by exposing thrombin to a molecule or molecules which interact with exosite I and the active site on thrombin. Preferably, said molecule or molecules interact with all of exosite I, exosite II and the active site on thrombin.

According to a second aspect of the invention, there is provided a thrombin inhibitor molecule or molecules suitable for use in the methods of the first aspect of the invention which interact with exosite I and the active site of thrombin. Preferably, the thrombin inhibitor molecule or molecules interact with all of exosite I, exosite II and the active site of thrombin.

Preferably, the molecule or molecules of the first or second aspects of the invention inhibit thrombin activity by first interacting with exosites I and II and then interacting with the active site of thrombin.

According to a third aspect of the invention, there is also provided a complex of a molecule or molecules of the second aspect of the invention and thrombin, wherein the thrombin inhibitor molecule interacts with exosite I and the active site of thrombin, preferably with all of exosite I, exosite II and the active site of thrombin.

Preferably, the molecule used in the method of the first aspect of the invention, the thrombin inhibitor molecule of the second aspect of the invention or present in the complexes of the third aspect of the invention is the variegin protein having the amino acid sequence SDQGDVAEPKMHKTAPPFD-FEAIPEEYLDDES (SEQ ID NO 1) or a functional equivalent of said variegin protein.

The isolation of the variegin protein having the amino acid sequence described above from the saliva of the tick *Amblyomma variegatum* is described in WO03/091284 in which the variegin protein is termed EV445. WO03/091284 discloses that the variegin protein inhibits thrombin-stimulated platelet aggregation. However, WO03/091284 does not provide any experimental evidence as to whether the variegin protein is a direct thrombin inhibitor that exerts its effects by direct interaction with thrombin.

Surprisingly, it has now been found that the variegin protein not only interacts directly with thrombin but that it does so at three separate sites. The results presented herein show that residues 1-7 of the variegin protein interact with exosite II of thrombin, residues 8-14 of the variegin protein interact with and bind to the active site of thrombin and residues 15-32 of the variegin protein interact with and bind to exosite I of thrombin. Existing direct thrombin inhibitors, both natural and synthetic, e.g. hirudin and hirulog, are bivalent. They interact with an exosite on thrombin and the thrombin active site itself. The variegin protein is the first example known to the inventors of a thrombin inhibitor that interacts with both thrombin exosites and the thrombin active site. Interaction of residues 1-7 and 15-32 of the variegin protein with the thrombin exosites II and I appears to align residues 8-14 of the variegin protein for binding with the thrombin active site, with subsequent binding of residues 15-32 with exosite I reinforcing the active site binding.

Unlike other thrombin inhibitors, the variegin protein is shown herein not to cross-react with other serine proteases, a feature that is also believed to be due to its ability to interact with multiple domains in thrombin.

The natural variegin protein which is glycosylated at position 14 is shown herein to display a high affinity for thrombin and high levels of inhibitory activity (Ki of approximately 10.4 pM and IC50 of approximately 0.99 nM) in an amidolytic assay of the type described above. A synthetic variegin protein having the same sequence but no glycosylation at position 14 displays a Ki of around 146 pM and an $IC_{50}$ of around 5.40 nM in an amidolytic assay of the type described above. The speed of onset of thrombin inhibitory action is believed to be due to the nature of variegin interaction with thrombin and is useful in clinical situations where rapid and potent anticoagulation are desired, such as emergency use following acute myocardial infarction, thrombotic stroke, pulmonary embolism or disseminated intravascular coagulation. The data presented herein show that variegin has a plasma half-life of 0.86 hours and a terminal elimination half-life of 117.2 hours. Autoradiography studies presented herein shown that variegin is rapidly excreted by the renal route confirming that it is likely to be particularly useful for short-term anticoagulation during surgical procedures.

The crystal structure of thrombin has been elucidated and the identities and locations of the active site, exosite I and exosite II of thrombin are well-known. Thrombin is highly homologous to other serine proteases such as chymotrypsin, and has an active site pocket in which the substrate binds surrounded by two charged regions, exosites I and II. The terms "active site", "exosite I" and "exosite II" of thrombin as used herein are thus intended to refer to these sites as described in the art, for example as described in Lane et al (Blood, 2005 Oct. 15; 106(8):2605-12).

In brief, the term "active site" is used to describe the pocket in thrombin in which the fibrinogen substrate binds and which contains the active serine residue (S195) framed by the 60- and γ-loops. The 60-loop is hydrophobic with a structural rigidity provided by two adjacent Pro residues (P60b, P60c). It interacts with hydrophobic residues of the substrate, N-terminal to the cleavage site. The γ-loop is more mobile, hydrophilic, and can make contact with residues C-terminal to the cleavage site. The term "exosite I" as used herein is the site adjacent to the active site centred on residues K36, H71, R73, R75, Y76, R77a, and K109/110. The term "exosite II" as used herein is the site adjacent to the active site centred on residues R93, K236, K240, R101, and R233 on the opposite site of thrombin to exosite I.

The molecule or molecules of the invention may interact with the sites on thrombin by electrostatic interaction. Such electrostatic interactions may be short-range electrostatic interactions and/or long-range electrostatic interactions. Preferably, the electrostatic interactions are strong enough to form an ionic bond between the molecule and the sites on thrombin.

The ability of the molecules of the invention to inhibit thrombin activity may be determined by standard assays known in the art. For example, thrombin amidolytic activity may be assessed by detecting the formation of p-nitroaniline following incubation of thrombin with postulated thrombin inhibitors in the presence of S2238. The molecules of the invention may have an $IC_{50}$ of less than 30 nM, less than 25 nM, less than 20 nM, less than 15 nM, less than 14 nM, less than 13 nM, less than 12 nM, or less than 11 nM. Preferably, the molecules of the invention have an $IC_{50}$ of less than 10 nM, preferably less than 9 nM, less than 8 nM, less than 7 nM, less than 6 nM, less than 5 nM, less than 4 nM, less than 3 nM, less than 2 nM or less than 1 nM when assessed in such a thrombin amidolytic assay. The molecules of the invention may have a Ki of less than less than 15 nM, less than 10 nM, less than 5 nM, less than 1 nM, less than 750 pM, less than 500 pM, less than 400 pM, less than 300 pM, or less than 250 pM. Preferably, the molecules of the invention have a Ki of less than 200 pM, preferably less than 150 pM, less than 100 pM, less than 50 pM, less than 30 pM, less than 25 pM, less than 20 pM, less than 15 pM when assessed in such a thrombin amidolytic assay. Preferably, the molecule or molecules of the first or second aspects of the invention inhibit thrombin activity by preventing access of fibrinogen to the active site of thrombin. The fibrinogenolytic activity of the molecules of the invention may be assessed by detecting ability to prolong fibrinogen clotting time, e.g. by incubating the molecules with fibrinogen and initiating clotting by the addition of thrombin.

The ability of the molecule or molecules of the first and second aspects of the invention to interact with sites on the thrombin molecule may be determined through methods such as those described in the examples herein. For example, a molecule having amidolytic activity in the assay described above is able to interact with the thrombin active site, whereas fibrinogenolytic activity requires binding of fibrinogen to both the active site and exosite I of thrombin. Molecules which display both amidolytic activity and fibrinogenlytic activity may thus be inferred to interact with both the active site and exosite I. The ability of the molecules to interact with exosite II may be assessed by analysis of a change in the binding kinetics of the reaction. The presence of an interaction with the exosite II appears to result in fast binding characteristics and deletion of residues interacting with exosite II results in a change in binding characteristics from fast to slow. Deletion mutants may be used to determine the precise locations of domains in the molecule binding to these different sites.

Preferably, the molecule or molecules used in the method of the first and the molecule or molecules of the second aspect of the invention inhibit thrombin specifically. Preferably, the molecule or molecules of the invention display very low levels of inhibition of other serine proteases, preferably no inhibition of other serine proteases at all. The ability of the molecule or molecules of the invention to inhibit thrombin specifically may be tested by assessing its ability to inhibit the amidolytic activities of a variety of serine proteases in the amidolytic assay described above, using specific chromogenic substrates for each serine protease. Preferably, the molecule or molecule of the invention do not inhibit other fibrinolytic serine proteases (such as plasmin, TPA and urokinase), anticoagulant protease APC or other anticoagulant serine proteases (such as FXIIa, FXI1, FX1, FIXa, FVIIa and kallikrein), or other classical serine proteases (such as chymotrypsin and trypsin).

Preferably, the molecule or molecules used in the method of the first aspect and the molecule or molecules of the second aspect of the invention have a random coil structure. The random coil structure of the molecules of the invention may be assessed by circular dichroism spectroscopy.

The molecule or molecules used in the method of the first aspect and the molecule or molecules of the second aspect of the invention may have a half-life when administered in vivo of less than 1 hour.

As disclosed above, the molecule used in the method of the first aspect of the invention and the molecule of the second aspect of the invention is preferably the variegin protein or a functional equivalent thereof.

"Functional equivalents" of the variegin protein invention include molecules that show significant structural similarity to the variegin protein and retain the preferred characteristics of molecules of the invention discussed above. In particular, functional equivalents retain the ability to interact with exosite I and the active site on thrombin and preferably to interact with exosite I, exosite II and the active site on thrombin. Functional equivalents of the variegin protein thus preferably have a random coil structure, retain the preferred Ki and IC50 values discussed above in connection with other molecules of the invention and display the ability to inhibit thrombin activity specifically.

The results presented herein show that the affinity of the variegin protein for thrombin is such that, unlike bivalent or univalent direct thrombin inhibitors such as bivalirudin, the variegin protein does not show any significant loss of thrombin activity even when it has been cleaved by thrombin. It is postulated that the ability of the variegin protein to interact at several sites leads to strong affinity of the protein to the thrombin active site and this strong affinity is retained by variegin cleavage products even after cleavage by thrombin. These cleavage products are thus considered together to be functional equivalents of the variegin protein. The variegin protein is cleaved by thrombin between amino acids 10 and 11. The method of the first aspect of the invention may therefore comprise inhibiting thrombin activity by exposing thrombin to the cleavage products of variegin having the amino acid sequences SDQGDVAEPK (SEQ ID NO 2) and MHKTAPPFDFEAIPEEYLDDES (MH22) (SEQ ID NO 3), or functional equivalents of these cleavage products. Additionally, the complex of the third aspect of the invention may comprise thrombin and the cleavage products of variegin having the amino acid sequences SDQGDVAEPK (SEQ ID NO 2) and MHKTAPPFDFEAIPEEYLDDES (SEQ ID NO 3), or functional equivalents of these cleavage products.

Functional equivalents of the variegin sequence or cleavage products also include variants in which 1, 2, 3, 4, 5, 6, 7, 8, 9, 10 or more amino acids in the variegin protein sequence, or variegin protein cleavage product sequences, have been substituted for alternative amino acids, provided that the ability to interact with thrombin at exosite I and the active site, preferably at exosite II, exosite I and the active site is retained.

Preferably, variants will contain conservative amino acid substitutions compared to the original variegin protein sequence. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr.

The results presented herein demonstrate the existence of variants of the variegin protein having amino acid substitutions at some or all of positions 4, 5, 6, 8, 11, 12, 13, 14, 17, 18, 25 and 31 of the variegin protein sequence. The results presented herein also demonstrate that mutants of the variegin protein sequence having amino acid substitutions at positions 10 and 22 retain thrombin inhibitory activity. Preferred functional equivalents of the variegin protein thus include variants having amino acid substitutions at one or more of these positions. Preferred functional equivalents include variants in which Gly at position 4 is replaced by Ala or Ser, Asp at position 5 is replaced by Gly, Val at position 6 is replaced by Arg, Glu at position 8 is replaced by Gln, Lys at position 10 is replaced by Arg, Met at position 11 is replaced by Leu, His at position 12 is replaced by Pro, Lys at position 13 is replaced by Arg, Thr at position 14 is replaced by Asn, Pro at position 17 is replaced by Gin, Phe at position 18 is replaced by Gly, Ala at position 22 is replaced by Glu, Glu at position 25 is replaced by Asp, or Glu at position 31 is replaced by His. Functional equivalents include variants containing 1, 2, 3, 4, 5, 6, 7, 8, 9, 10, 11, 12, 13 or all 14 of these changes. A preferred variant is one in which the Glu at position 31 is replaced by His, said variant having the amino acid sequence SDQGDVAEPKMHKTAPPFDFEAIPEEYLDDHS (SEQ ID NO 4). This variant may additionally include substitutions at the positions mentioned above and at other positions within the molecule. Another variant of the invention is a variant of one of the cleavage products having an amino acid substation of a Glu for an Ala at position of the variegin sequence which thus has the sequence MHKTAPPFDFEEIPEEYLDDES (MH22A22E) (SEQ ID NO 7).

Preferably, such variants of the variegin protein or cleavage products display an improved ability to inhibit thrombin activity. Such an improved ability to inhibit 30 thrombin activity may be due to improved interaction with one or more of the exosite I, exosite II and/or active site on thrombin. Improved inhibition of thrombin activity may be assessed by determination of the $IC_{50}$ and Ki values of such variants using the assays described herein. Such variants may also display a similar half-life in vivo to the variegin protein.

The term "functional equivalent" also includes fragments of the variegin protein or fragments of variants thereof, provided that these fragments retain the ability to interact with the exosite I and active site on thrombin, preferably with the exosite I, exosite II and active site on thrombin. Such fragments will typically be identical to the variegin protein sequence or variants thereof except for the loss of 1, 2, 3, 4, 5, 6, 7, 8, 9 or 10 amino acids from the N-terminal and 1, 2, 3 or 4 amino acids from the C-terminal of the variegin protein sequence. Such fragments may also contain amino acid substitutions at one or more of the positions recited above. Examples of such fragments include fragments having an amino acid sequence selected from:

```
                                            (SEQ ID NO 6)
    EPKMHKTAPPFDFEAIPEEYLDDES (EP25)

(SEQ ID NO 7)
    EPKMHKTAPPFDFEEIPEEYLDDES (EP25A22E)

(SEQ ID NO 8)
    EPKMHKTAPPFDFEAIPEEYL (EP21)

(SEQ ID NO 20)
    MHKTAPPFDFEAIPEEYL (MH18)

(SEQ ID NO 9)
    DVAEPKMHKTAPPFDFEAIPEEYL (DV24)

(SEQ ID NO 10)
    DVAEPRMHKTAPPFDFEAIPEEYL (DV24K10R)

(SEQ ID NO 11)
    SDQGDVAEPKMHKTAPPFDFEAIPEEYL (SEQ ID NO 12)
    SDQADRAQPKLHRNAPQGDFEAIPDEYL
```

```
                                               (SEQ ID NO 13)
SDQSGRAQPKLPRNAPQGDFEAIPDEYL (SEQ ID NO 14)
SDQGDVAEPKMHKTAPPGDFEAIPEEYLD (SEQ ID NO 15)
SDQADVAEPKMHKTAPPGDFEAIPEEYLD
```

Functional equivalents also include modified forms of the variegin protein and variants and fragments thereof that have been modified by the addition of sugar groups or polymer groups to amino acids within the variegin protein or variants thereof. In particular, functional equivalents include glycosylated forms of the variegin protein. In the natural form of variegin, the Thr at position 14 of the full-length sequence is modified by a hexose moiety. Functional equivalents thus include the variegin protein, and variants and fragments of the variegin protein discussed above, modified by glycosylation at a position corresponding to position 14 of the variegin protein sequence. Functional equivalents also include the variegin protein, and variants and fragments thereof, that have been modified by glycosylation at other positions. Preferably, the glycosylation comprises introduction of a hexose residue. Functional equivalents also include PEGylated forms of the variegin protein and variants and fragments thereof. Such PEGylated forms are likely to be particularly useful to prolong the half-life of these molecules in certain medical applications.

A functional equivalent used according to the invention may also be a fusion protein, obtained, for example, by cloning a polynucleotide encoding the variegin protein or variant or fragment thereof in frame to the coding sequences for a heterologous protein sequence. The term "heterologous", when used herein, is intended to designate any polypeptide other than the variegin protein or its functional equivalent. Examples of heterologous sequences, comprising the fusion proteins, either at N- or at C-terminus, are the following: extracellular domains of membrane-bound protein, immunoglobulin constant regions (Fc region), multimerization domains, domains of extracellular proteins, signal sequences, export sequences, or sequences allowing purification by affinity chromatography. Many of these heterologous sequences are commercially available in expression plasmids since these sequences are commonly included in the fusion proteins in order to provide additional properties without significantly impairing the specific biological activity of the protein fused to them (Terpe K, Appl Microbiol Biotechnol, 60: 523-33, 2003). Examples of such additional properties are a longer lasting half-life in body fluids, the extracellular localization, or an easier purification procedure as allowed by a tag such as a histidine or HA tag.

Fusion proteins will also have medical applications. For example, since the variegin protein and functional equivalents thereof are able to bind thrombin, they can be used as a means of conveying a therapeutic molecule to the site of a fibrin or platelet thrombus. The heterologous protein may therefore be a therapeutic molecule that is useful in the treatment of a fibrin or a platelet thrombus. Preferably, such a therapeutic molecule is an anti-inflammatory agent or a thrombolytic agent.

The heterologous protein may also be a marker domain. Preferably, the marker domain is a fluorescent tag, an epitope tag that allows purification by affinity binding, an enzyme tag that allows histochemical or fluorescent labelling, or a radiochemical tag. In a preferred embodiment, the marker domain is a radiochemical tag. Such fusion proteins will be useful as diagnostic tools. For example, since the variegin protein is able to bind to thrombin, it can be used as a means of imaging a fibrin or platelet thrombus when linked to a suitable marker domain, such as a suitable radiochemical tag.

Methods for the generation of fusion proteins are standard in the art and will be known to the skilled reader. For example, most general molecular biology, microbiology, recombinant DNA technology and immunological techniques can be found in Sambrook et al. (2000) or Ausubel et al. (1991). Generally, fusion proteins may be most conveniently generated recombinantly from nucleic acid molecules in which two nucleic acid sequences are fused together in frame. These fusion proteins will be encoded by nucleic acid molecules that contain the relevant coding sequence of the fusion protein in question.

Functional equivalents also include multimers of the variegin proteins, variants, fragments, modified variants or fragments, or fusion proteins described above. These multimers constitute a further aspect of the invention as well as being useful for the method of the first aspect of the invention. It is considered that such multimers of the variegin protein may be particularly useful in order to bind and inhibit large quantities of thrombin. The variegin proteins within these multimers may all be linked to central linker moiety via their C-terminus. Alternatively, the variegin proteins may be linked in a long string N-terminus to C-terminus. Preferably, the multimers comprise 2, 3, 4, 5 or more copies of the variegin protein or variants, fragments functional equivalents thereof. The variegin protein or functional equivalents thereof within the multimer may all be identical to one another or they may be different. For example, a multimer may comprise several different variants of the variegin protein.

The method of the first aspect of the invention may be carried out in vitro or in vivo.

Where the method is carried out in vitro, it may be carried out in a cell-free system or in a cell comprising a nucleotide sequence encoding the molecule or molecules that interact with thrombin. The invention thus further provides a nucleic acid molecule comprising a nucleotide sequence encoding a thrombin inhibitor according to the second aspect of the invention that will be useful in the method of the first aspect of the invention. Such molecules include single- or double-stranded DNA, cDNA and RNA, as well as synthetic nucleic acid species. Preferably, the nucleic acid sequences comprise DNA.

These nucleic acid sequences may also be used when the method of the invention is conducted in vivo as discussed below.

The invention also includes cloning and expression vectors comprising the nucleic acid molecules of this aspect of the invention. Such expression vectors may incorporate the appropriate transcriptional and translational control sequences, for example enhancer elements, promoter-operator regions, termination stop sequences, mRNA stability sequences, start and stop codons or ribosomal binding sites, linked in frame with the nucleic acid molecules of the invention. Additionally, it may be convenient to cause the recombinant thrombin inhibitor molecule or molecules to be secreted from certain hosts. Accordingly, further components of such vectors may include nucleic acid sequences encoding secretion, signalling and processing sequences.

Vectors according to the invention include plasmids and viruses (including both bacteriophage and eukaryotic viruses), as well as other linear or circular DNA carriers, such as those employing transposable elements or homologous recombination technology. Many such vectors and expression systems are known and documented in the art (Fernandez & Hoeffler, 1998). Particularly suitable viral vectors include baculovirus-, adenovirus- and vaccinia virus-based vectors.

Suitable hosts for recombinant expression include commonly used prokaryotic species, such as *E. coli*, or eukaryotic yeasts that can be made to express high levels of recombinant proteins and that can easily be grown in large quantities. Mammalian cell lines grown in vitro are also suitable, particularly when using virus-driven expression systems. Another suitable expression system is the baculovirus expression system that involves the use of insect cells as hosts. An expression system may also constitute host cells that have the DNA incorporated into their genome. Proteins, or protein fragments may also be expressed in vivo, for example in insect larvae or in mammalian tissues.

A variety of techniques may be used to introduce vectors into prokaryotic or eukaryotic cells. Suitable transformation or transfection techniques are well described in the literature (Sambrook et al, 1989; Ausubel et al, 1991; Spector, Goldman & Leinwald, 1998). In eukaryotic cells, expression systems may either be transient (e.g. episomal) or permanent (chromosomal integration) according to the needs of the system.

The invention also provides antisense nucleic acid molecules which hybridise under high stringency hybridisation conditions to the nucleic acid molecules encoding a thrombin inhibitor molecule according to the second aspect of the invention. High stringency hybridisation conditions are defined herein as overnight incubation at 42° C. in a solution comprising 50% formamide, 5×SSC (150 mM NaCl, 15 mM trisodium citrate), 50 mM sodium phosphate (pH7.6), 5× Denhardts solution, 10% dextran sulphate, and 20 microgram/ml denatured, sheared salmon sperm DNA, followed by washing the filters in 0.1×SSC at approximately 65° C. In a preferred embodiment, a label capable of being detected is attached to these antisense nucleic acid molecules. Preferably, the label is selected from the group consisting of radio-isotopes, fluorescent compounds and enzymes.

The invention also includes transformed or transfected prokaryotic or eukaryotic host cells comprising a nucleic acid molecule, an antisense nucleic acid molecule or a vector as defined above. Preferably, the host cells are prokaryotic cells, preferably *E. coli* cells. Where the method of the invention is conducted in vitro, it may be conducted in such cells.

A further aspect of the invention provides a method for preparing a thrombin inhibitor molecule according to the second aspect of the invention which comprises culturing a host cell containing a nucleic acid molecule according to the invention under conditions whereby the protein is expressed and recovering the protein thus produced. The thrombin inhibitor thus produced may be used in the method of the first aspect of the invention.

Where the method of the first aspect of the invention is carried out in vivo, it may be used in therapy. In particular, methods carried out in vivo may be used to treat or prevent disorders of blood coagulation.

According to a preferred embodiment of the first aspect of the invention, there is thus provided a method of treating a patient suffering from a coagulopathy or preventing a patient developing a coagulopathy comprising inhibiting interaction of thrombin with fibrinogen at exosite II and the active site on the thrombin molecule. Preferably, the method of this embodiment of the first aspect of the invention comprises inhibiting interaction of thrombin with fibrinogen at all of exosite I, exosite II and the active site of thrombin.

Preferably, the method of this aspect of the invention comprises supplying the patient with a molecule or molecule of the second aspect of the invention that inhibits thrombin by interacting with exosite I and the active site, preferably by interacting with a molecule or molecules that interacts with exosite I, exosite II and the active site. Preferably, the molecule or molecules is the variegin protein or a functional equivalent thereof as described above. Alternatively, the method may comprise supplying a nucleic acid molecule encoding such a molecule or molecules of the second aspect of the invention, as described above.

By "coagulopathy" is meant any disorder of blood coagulation. The term "therapeutically effective amount" refers to the amount of compound needed to treat or ameliorate a targeted disease or condition. The term "prophylactically effective amount" used herein refers to the amount of compound needed to prevent a targeted disease or condition. The exact dosage will generally be dependent on the patient's status as the time of administration. Factors that may be taken into consideration when determining dosage include the severity of the disease state in the patient, the general health of the patient, the age, weight, gender, diet, time and frequency of administration, drug combinations, reaction sensitivities and the patient's tolerance or response to therapy. The precise amount can be determined by routine experimentation, but may ultimately lie with the judgement of the clinician. Generally, an effective dose will be from 0.01 mg/kg (mass of drug compared to mass of patient) to 50 mg/kg, preferably 0.05 mg/kg to 10 mg/kg.

Where the method of the invention is carried out in vivo, the molecule or molecules that interact with thrombin, or the nucleic acid molecules encoding them, are preferably supplied in the form of a pharmaceutical composition in conjunction with a pharmaceutically acceptable carrier.

The term "pharmaceutically acceptable carrier", as used herein, includes genes, polypeptides, antibodies, liposomes, polysaccharides, polylactic acids, polyglycolic acids and inactive virus particles or indeed any other agent provided that the excipient does not itself induce toxicity effects or cause the production of antibodies that are harmful to the individual receiving the pharmaceutical composition. Pharmaceutically acceptable carriers may additionally contain liquids such as water, saline, glycerol, ethanol or auxiliary substances such as wetting or emulsifying agents, pH buffering substances and the like. Excipients may enable the pharmaceutical compositions to be formulated into tablets, pills, dragees, capsules, liquids, gels, syrups, slurries, suspensions to aid intake by the patient. A thorough discussion of pharmaceutically acceptable carriers is available in Remington's Pharmaceutical Sciences (Mack Pub. Co., N.J. 1991).

Anticoagulants and thrombin inhibitors in particular have applications in the treatment and prevention of a wide range of diseases and conditions. The molecules and compositions described above may be used in any situation in which it is desired to induce anticoagulation to prevent or treat a coagulopathy.

Treatment when anticoagulation is desirable include procedures involving percutaneous, transvascular or transorgan catheterisation for diagnostic or therapeutic reasons. Such procedures may include but are not confined to: Coronary angioplasty; endovascular stent procedures; direct administration of thrombolytic agents via an arterial or venous catheter such as following stroke or coronary thrombosis; electrical cardioversion; placement of cardiac pacemaker leads; intravascular and intracardiac monitoring of pressure, gaseous saturation or other diagnostic parameters; radiological and other procedures involving percutaneous or transorgan catheterisation; to ensure the patency of long-term, indwelling, intravascular parenteral nutritional catheters; to ensure the patency of vascular access ports whether long or short term.

It has been demonstrated that the bivalent direct thrombin inhibitors such as bivalirudin are superior to heparin and its analogues for use during such procedures (Lehman, S. J., and D. P. Chew. 2006, Vasc Health Risk Manag 2: 357-63; Maclean, A. A. et al, 2006. Tech Vasc Interv Radiol 9: 80-3; Lewis, B. E., and M. J. Hursting. 2007., Expert Rev Cardiovasc Ther 5: 57-68.; Watson, K. et al, 2007, Pharmacotherapy 27: 647-56.). In particular the incidence of perioperative bleeding is substantially reduced and in patients with acute coronary syndrome (ACS) the incidence of subsequent MI is reduced (Stone, G. W. et al, 2006, N Engl J Med 355: 2203-16.; Manoukian, S. V. et al, 2007. J Am Coll Cardiol 49: 1362-8.; Stone, G. W. et al, 2007, Lancet 369: 907-19). It is therefore expected that the thrombin inhibitors discussed above will also be superior to heparin and its analogues for use during such procedures.

Additional in vivo applications of the methods of the first aspect of the invention include emergency anticoagulation after a thromboembolic event including but not limited to: acute myocardial infarction; thrombotic stroke; deep venous thrombosis; thrombophlebitis; pulmonary embolism; embolic and micro-embolic episodes where the source may be the heart, atherosclerotic plaque, valvular or vascular prostheses or an unknown source; disseminated intravascular coagulation (DIC).

The methods of the invention may also be used to prevent coagulation during organ perfusion procedures such as during cardiopulmonary bypass, hepatic bypass and as an adjunct to organ transplantation. The massive thrombotic reaction precipitated by CPB cannot fully be antagonised by indirect thrombin inhibitors such as heparin and its analogues (Edmunds, and Colman. 2006, Ann Thorac Surg 82: 2315-22.).

Further instances when anticoagulation is desirable include during haemodialysis, haemofiltration or plasma exchange procedures. Anticoagulation may also be desirable during surgical procedures involving cross clamping of blood vessels in order to minimise the risk of coagulation in the distal circulation. Such procedures may include but are not confined to endarterectomy, insertion of vascular prostheses, repair of aortic and other arterial aneurysms.

Additionally, the methods and the thrombin inhibitors of the invention may be useful to induce anticoagulation in heparin-resistant patients.

The methods and thrombin inhibitors may also be useful in the treatment or prevention of heparin-induced thrombocytopaenia. Such treatment may be administered to a patient with or at risk from HIT and with or without active thrombosis and may be administered until platelet counts have recovered to within the range of normal or until the risk of thrombosis has passed (Girolami and Girolami 2006, Semin Thromb Hemost 32: 803-9; Lewis, B. E., and M. J. Hursting. 2007. Expert Rev Cardiovasc Ther 5: 57-68.)

According to a particular aspect of the invention, the in vivo method involves supplying a patient suffering from a condition caused by thrombin accumulation with a fusion protein comprising thrombin inhibitors of the second aspect of the invention genetically or chemically fused to a therapeutic molecule, in a therapeutically effective amount. The methods of the invention involve direct interaction with thrombin. This feature means that they can be used to convey the therapeutic molecule to the site of thrombin accumulation. Preferably, the therapeutic molecule is an anti-inflammatory agent or a thrombolytic agent. Preferably, the condition is a fibrin or a platelet thrombus.

The thrombin inhibitors may be administered by any suitable route. Preferred routes of administration include intravenous, intramuscular or subcutaneous injection and oral administration. The treatment may be continuously administered by intravenous infusion or as a single or repeated bolus injection. The thrombin inhibitor may be administered individually to a patient or may be administered in combination with other agents, drugs or hormones. For example, the thrombin inhibitors of the invention may be administered with oral anticoagulants such as coumarin derivatives until such time as the patient has become stabilised, following which the patient may be treated with the coumarin derivatives alone.

The invention further provides that the methods of the first aspect of the invention may be used in diagnosis. Since these methods involve inhibiting thrombin activity specifically by interaction with thrombin, they can be used to detect the presence of thrombin and hence to diagnose conditions caused by thrombin accumulation, such as a fibrin or platelet thrombus. The invention therefore provides that the method of the first aspect of the invention may involve diagnosing a condition caused by thrombin accumulation by administering a thrombin inhibitor of the second aspect of the invention as described above to a patient or to tissue isolated from a patient, and detecting the presence of said thrombin inhibitor or functional equivalent thereof, wherein the detection of said thrombin inhibitor or functional equivalent bound to thrombin is indicative of said disease or condition. Preferably, the thrombin inhibitor or functional equivalent is in the form of a fusion protein comprising a marker domain, as described in more detail above, to facilitate detection. Preferably, the marker domain is a radiochemical tag so that detection can be carried out using known imaging methods. Preferably, the disease or condition is a fibrin or platelet thrombus.

According to a further aspect of the first aspect of the invention, the in vivo method of the first aspect of the invention may be used to treat a malignant disease or a condition associated with malignant disease.

It has been recognised for decades that malignant disease is often associated with an increased tendency to thromboembolic episodes. Trousseau's syndrome, for example, is characterised by fleeting thrombophlebitis and underlying malignancy and thrombin inhibitors such as heparin have been used in its management (Varki A. Trousseau's Syndrome: multiple definitions and multiple mechanisms. Blood 2007). More recently it has become apparent that the generation of procoagulant factors including thrombin may be a cause rather than a result of certain aspects of malignant disease (Nierodzik M L, Karpatkin S. Thrombin induces tumor growth, metastasis, and angiogenesis: Evidence for a thrombin-regulated dormant tumor phenotype. Cancer Cell 2006; 10(5):355-62.).

Thrombin, VEGF and IGFII have been shown to promote the survival and invasivity of cancer cells (Gieseler F, Luhr I, Kunze T, et al. Activated coagulation factors in human malignant effusions and their contribution to cancer cell metastasis and therapy. Thromb Haemost 2007; 97(6):1023-30.). Thrombin cleavage of the COOH terminus of osteopontin has been shown to promote breast cancer in mice (Mi Z, Oliver T, Guo H, Gao C, Kuo P C. Thrombin-cleaved COOH(—) terminal osteopontin peptide binds with cyclophilin C to CD147 in murine breast cancer cells. Cancer Res 2007; 67(9):4088-97.). Thrombin appears to play a role in the metastasis of prostate cancer by decreasing cell adhesion to the extracellular matrix and positioning the malignant cell in a 'ready state' for migration (Loberg R D, Tantivejkul K, Craig M, Neeley C K, Pienta K J. PAR1-mediated RhoA activation facilitates CCL2-induced chemotaxis in PC-3 cells. J Cell Biochem 2007). It is possible therefore that the use of a potent thrombin inhibitor during surgical procedures such as radical prostatectomy or prostatic biopsy might reduce the release of malignant cells into the systemic circulation and decrease the survival of those cells that are released.

The method of the first aspect of the invention and molecules of the second aspect of the invention may therefore be useful for the treatment of Trousseau's syndrome particularly when heparin and its analogues are contraindicated (eg in heparin-induced thrombocytopaenia); for use as an anti-cancer agent; and for use during procedures such as surgical excision, manipulation or biopsy of malignant tumours in order to reduce the risk of metastasis. Where the molecule used in this aspect of the invention is a variegin protein or functional equivalent thereof, it is preferably in a modified form that has been glycosylated or PEGylated in order to increase the half-like of the molecule.

The results presented herein provide the first disclosure of the functional domains of the variegin protein, as well as the first disclosure of the cleavage products of the variegin molecule. In particular, the results presented herein disclose that residues 1-7 of the variegin protein interact with thrombin exosite II, residues 8-14 of the variegin protein interact with the active site of thrombin and residues 15-32 interact with thrombin exosite I binding site. These regions are believed to act together in the full-length variegin protein to inhibit thrombin activity. However, as discussed in the introduction, many existing thrombin inhibitors are univalent or bivalent binders. It is therefore expected that fragments of the variegin protein or variants thereof interacting with only one of these regions on thrombin will also be thrombin inhibitors. Indeed, the results presented herein show that a fragment containing the binding site for the thrombin active site and the binding site for exosite I (EP25) had an IC50 and Ki value similar to that of the full-length synthetic variegin protein. Fragments of the variegin protein that interact with just one or two sites within thrombin may have an advantage of the full-length variegin protein for medical applications in that they will be cleared more rapidly from the circulation. This makes them ideal for use in short procedures such as cardiac catheterisation where it is not desirable for anticoagulation to continue beyond the end of the procedure.

According to a further aspect of the invention, there is thus provided a thrombin inhibitor, wherein said thrombin inhibitor comprises a fragment of the variegin sequence and comprises an amino acid sequence selected from:

```
                                          (SEQ ID NO 6)
EPKMHKTAPPFDFEAIPEEYLDDES (EP25-interaction with
active site and exosite I)

(SEQ ID NO 16)
APPFDFEAIPEEYLDDES (AP18-interaction with exosite
I)

(SEQ ID NO 17)
SDQGDVAEPKMHKT (interaction with exosite II and
active site)

(SEQ ID NO 18)
SDQGDVA (interaction with exosite II)

(SEQ ID NO 19)
EPKMHKT (interaction with active site)

(SEQ ID NO 16)
APPFDFEAIPEEYLDDES (interaction with exosite I)

(SEQ ID NO 2)
SDQGDVAEPK (cleavage product 1)
```

```
                                          -continued
                                          (SEQ ID NO 3)
MHKTAPPFDFEAIPEEYLDDES (cleavage product 2; MH22)

(SEQ ID NO 8)
EPKMHKTAPPFDFEAIPEEYL (EP21)

(SEQ ID NO 20)
MHKTAPPFDFEAIPEEYL (MH18)

(SEQ ID NO 9)
DVAEPKMHKTAPPFDFEAIPEEYL (DV24)
or a functional equivalent thereof.
```

The thrombin inhibitor of this aspect of the invention is a fragment of the variegin protein and does not therefore contain the complete sequence of the variegin protein having the amino acid sequence SDQGDVAEPKMHKTAPPFDFEAIPEEYLDDES (SEQ ID NO 1). The thrombin inhibitor of this aspect of the invention may, however, contain additional amino acid residues from the variegin protein sequence at the N- or C-terminus of the specific fragment sequences recited above provided that the thrombin does not comprise all of the amino acids of the variegin protein.

The thrombin inhibitors of this aspect of the invention also include molecules containing more than one of the specific fragments recited above. For example, the thrombin inhibitor may comprise SDQGDVA (SEQ ID NO 18) (interaction with exosite II) and APPFDFEAIPEEYLDDES (interaction with exosite I) (SEQ ID NO 16). Preferably, these exosite II and exosite I interacting sites are connected by a linker molecule that is approximately the same length as the thrombin active binding site that is present in the full-length variegin protein.

The thrombin inhibitor of this aspect of the invention may consist of one of the sequences recited above or a functional equivalent thereof.

Thrombin inhibitors according to the fourth aspect of the invention preferably display the characteristics of the thrombin inhibitors of the second aspect of the invention discussed above, such as the preferred Ki and IC50 values and the ability to inhibit thrombin specifically without inhibiting other serine protease.

Functional equivalents of the thrombin inhibitors of this aspect of the invention include molecules that show significant structural similarity to the thrombin inhibitors of the fourth aspect of the invention and retain the ability to interact with the same regions of thrombin as the thrombin inhibitors from which they are derived. Functional equivalents according to this aspect of the invention include variants of the specific thrombin inhibitors recited above containing one or more amino acid substitutions that do not substantially alter the interaction of the thrombin inhibitor with thrombin. Preferably, such amino acid substitutions are conservative amino acid substitutions such as those described in connection with the molecules of the first and second aspects of the invention above. Preferred substitutions are those occurring at the amino acid positions discussed above in connection with variants of the full-length variegin protein.

Examples of such functional equivalents include variants having an amino acid sequence selected from:

```
                                          (SEQ ID NO 7)
       EPKMHKTAPPFDFEEIPEEYLDDES (EP25A22E)

(SEQ ID NO 10)
       DVAEPRMHKTAPPFDFEAIPEEYL (DV24K10R)

(SEQ ID NO 5)
       MHKTAPPFDFEEIPEEYLDDES (MH22A22E)
```

Functional equivalents of the thrombin inhibitors of this aspect of the invention also include fragments of the thrombin inhibitors provided that these fragments retain the ability to inhibit thrombin activity.

Functional equivalents also include modified forms of the thrombin inhibitors and fragments thereof that have been modified by the covalent attachment of additional groups, such as sugar groups or polymer groups. Examples of such modifications provided above in relation to the functional equivalents variegin protein for use in the method of the first aspect of the invention are equally applicable to the thrombin inhibitors of this aspect of the invention.

Functional equivalents of this aspect of the invention also include fusion proteins of the thrombin inhibitors. Suitable partners for inclusion in such fusion proteins are discussed above in connection with fusion proteins containing the full-length variegin sequence.

The invention further provides a complex of a thrombin inhibitor according to this aspect of the invention and thrombin.

The invention further provides nucleic acid molecules comprising nucleotide sequences encoding a thrombin inhibitor according to this aspect of the invention. Such molecules include single- or double-stranded DNA, cDNA and RNA, as well as synthetic nucleic acid species. Preferably, the nucleic acid sequences comprise DNA.

The invention further includes cloning and expression vectors comprising these nucleic acid molecules. Such vectors may comprise additional control sequences, such as those described in connection with expression vectors used in connection with the method of the first aspect of the invention and the thrombin inhibitors of the second aspect of the invention described above.

The invention further includes antisense molecules which hybridise under high stringency conditions to the nucleic acid molecules encoding a thrombin inhibitor molecule according to this aspect of the invention. Examples of high stringency conditions are described above in connection with the molecules of the first and second aspects of the invention.

The invention further includes transformed or transfected prokaryotic or eukaryotic host cells comprising a nucleic acid molecule, an antisense nucleic acid molecule or a vector encoding a thrombin inhibitor molecule of this aspect of the invention. Suitable host cells and methods for preparing such host cells are discussed above in connection with the first and second aspects of the invention.

The invention further includes a method of preparing a thrombin inhibitor molecule according to this aspect of the invention comprising culturing a host cell containing a nucleic acid molecule according to the invention under conditions whereby the protein is expressed and recovering the protein thus produced.

The invention further includes the use of the thrombin inhibitors according to this aspect of the invention in therapy. The thrombin inhibitors according to this aspect of the invention may be in the form of a pharmaceutical composition additionally comprising a pharmaceutically effective carrier, as discussed above. The thrombin inhibitors according to this aspect of the invention may be used in the treatment or prevention of any of the disorders that may be treated using the method or molecules of the first and second aspects of the invention discussed above. The thrombin inhibitors of this aspect of the invention may also be used in any of the diagnostic methods discussed in connection with the method and molecules of the first and second aspects of the invention above.

Various aspects and embodiments of the present invention will now be described in more detail by way of example. It will be appreciated that modification of detail may be made without departing from the scope of the invention.

FIGURES

FIG. 1. Purification of the thrombin inhibitor variegin isoforms. (A) In the first step, SGE was fractionated with a gradient of 10-100% of acetonitrile over 90 min. Protein concentrations in pooled fractions of AV-I to AV-VIII ranged from 0.08 (AV-I) to 1.39 µg/µl (AV-IV). For TT assays (control clotting time=19 s): NC—no clot after adding <0.01 µg protein/50 µl plasma; * prolonged clotting of >1 min after adding <0.01 µg protein/50 µl plasma;  prolonged clotting of >40 s after adding <0.01 µg protein/50 µl plasma; * any delayed in clotting in comparison with control. For APTT assays (control clotting time=40 s): NC—no clot after adding <0.01 µg protein/50 µl plasma; ●●● prolonged clotting of >1 min after adding <0.01 µg protein; ●● prolonged clotting >1 min after adding <0.1 µg protein/50 µl plasma; ● any delayed in clotting in comparison with control. For PT assays (control clotting time=15 s): ●● prolonged clotting of >1 min after adding 0.5 µg protein/50 µl plasma; ● any delayed in clotting in comparison with control. (B) Fraction AV-III was subjected to a second purification step with a gradient of 10-40% of acetonitrile over 60 min. Protein concentrations in fractions ranged from 0.05 to 0.17 µg/µl. The range of fractions with anticoagulant activities (dashed line, assayed with PT, APTT and TT) were tested for the anti-thrombin activity with S2238. Fractions indicated with asterisks inhibited thrombin amidolytic activity. Two fractions with the strongest activity (retention time 23.083 and 28.933 min, indicated by arrows) were further purified with third step of purification (gradient of 10-40% of acetonitrile over 60 min) (n=2). (C) The fraction with retention time 23.083 min separated into two main peaks denoted AV 3/5 and AV 5/5. (D) The fraction with retention time 28.933 has one main peak and with a small 'shoulder peak' and was denoted AV 6/5.

Figure 2:
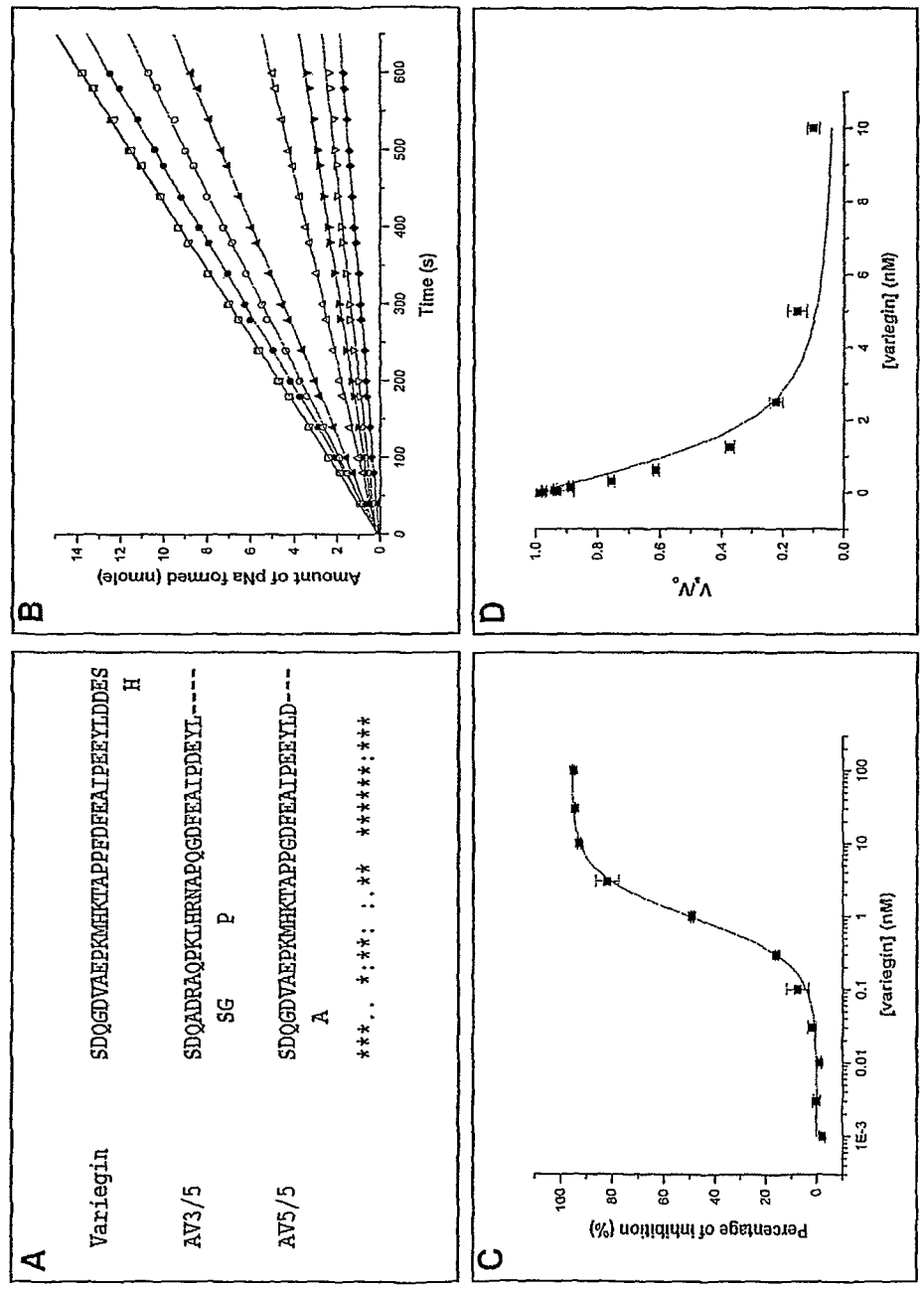

FIG. 2. Amino acid sequence of variegin and its thrombin inhibitory activity. (A) Sequences of peptides in fraction AV 6/5 (variegin), AV 3/5 and AV 5/5 are highly similar. (B) Example of linear progression curves of thrombin inhibition by variegin (■: 0.020 nM, □: 0.039 nM, ●: 0.078 nM, ○: 0.156 nM, ▲: 0.313 nM, ∆: 0.625 nM, ▼: 1.25 nM, ∇: 2.5 nM, ◆: 5 nM, 10 nM) using S2238 (100 µM) as substrate, showing steady state equilibrium achieved upon mixing. (C) The ability of variegin (0.001 nM, 0.003 nM, 0.01 nM, 0.03 nM, 0.1 nM, 0.3 nM, 1 nM, 3 nM, 10 nM, 30 nM and 100 nM) to inhibit thrombin (3.33 nM) amidolytic activity was assayed using active site directed substrate S2238 (100 µM). Dose response curve of thrombin inhibition by variegin (■) showed significant inhibition (~80%) for equimolar concentration of thrombin and variegin (3.33 nM). $IC_{50}$ of the inhibition is ~0.99±0.02 nM (n=3) (D) Since variegin behaved as a tight-binding inhibitor, inhibition of thrombin (1.8 nM) by variegin (■) at similar concentrations (0.020 nM, 0.039 nM, 0.078 nM, 0.156 nM, 0.313 nM, 0.625 nM, 1.25 nM, 2.5 nM, 5 nM, 10 nM) was examined using S2238 (100 µM) as substrate. Data obtained were fitted to equations (1) and (2) to derive a Ki of ~10.4±1.4 pM (n=3).

Figure 3:
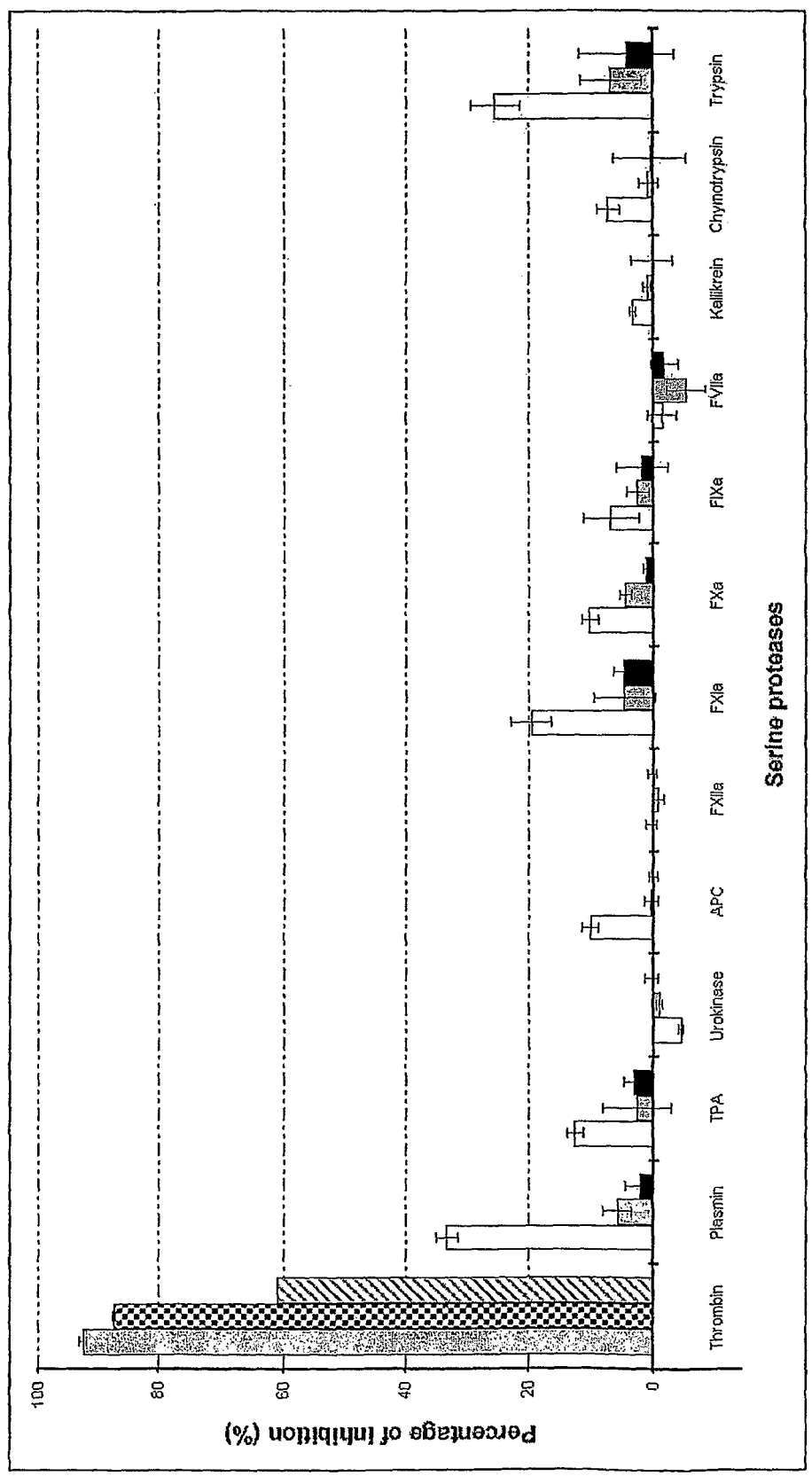

FIG. 3. Specificity of inhibition by variegin. S-variegin was screened against 13 serine proteases: fibrinolytic serine proteases (plasmin, TPA and urokinase), anticoagulant serine protease APC, procoagulant serine proteases (FXIIa, FXIa, FXa, FIXa, FVIIa, kallikrein and thrombin) and classical serine proteases (chymotrypsin and trypsin). The final concentrations of proteases and substrates are given in parentheses in nM and mM, respectively: plasmin (3.61)/S2251 (1.2), TPA (36.9)/S2288 (1), urokinase (40 U/ml)/S2444 (0.3), APC (2.14)/S2366 (0.67), FXIIa (20)/S2302 (1), FXIa (0.125)/S2366 (1), FXa (0.43)/S2765 (0.65), FIXa (333)/Spectrozyme® FIXa (0.4), FVIIa (460)/S2288 (1), kallikrein (0.93)/S2302 (1.1), α-thrombin (3.33)/S2238 (0.1), chymotrypsin (1.2)/S2586 (0.67) and trypsin (0.87)/S2222 (0.1). Thrombin was tested against three concentrations of s-variegin: (▨) represent 0.01 μM, (▩) represent 0.1 μM and (□) represent 1 μM. For the other proteases, much higher concentrations of s-variegin were used: (■) represent 1 μM, (□) represent 10 μM and (□) represent 100 μM (n=3).

Figure 4:
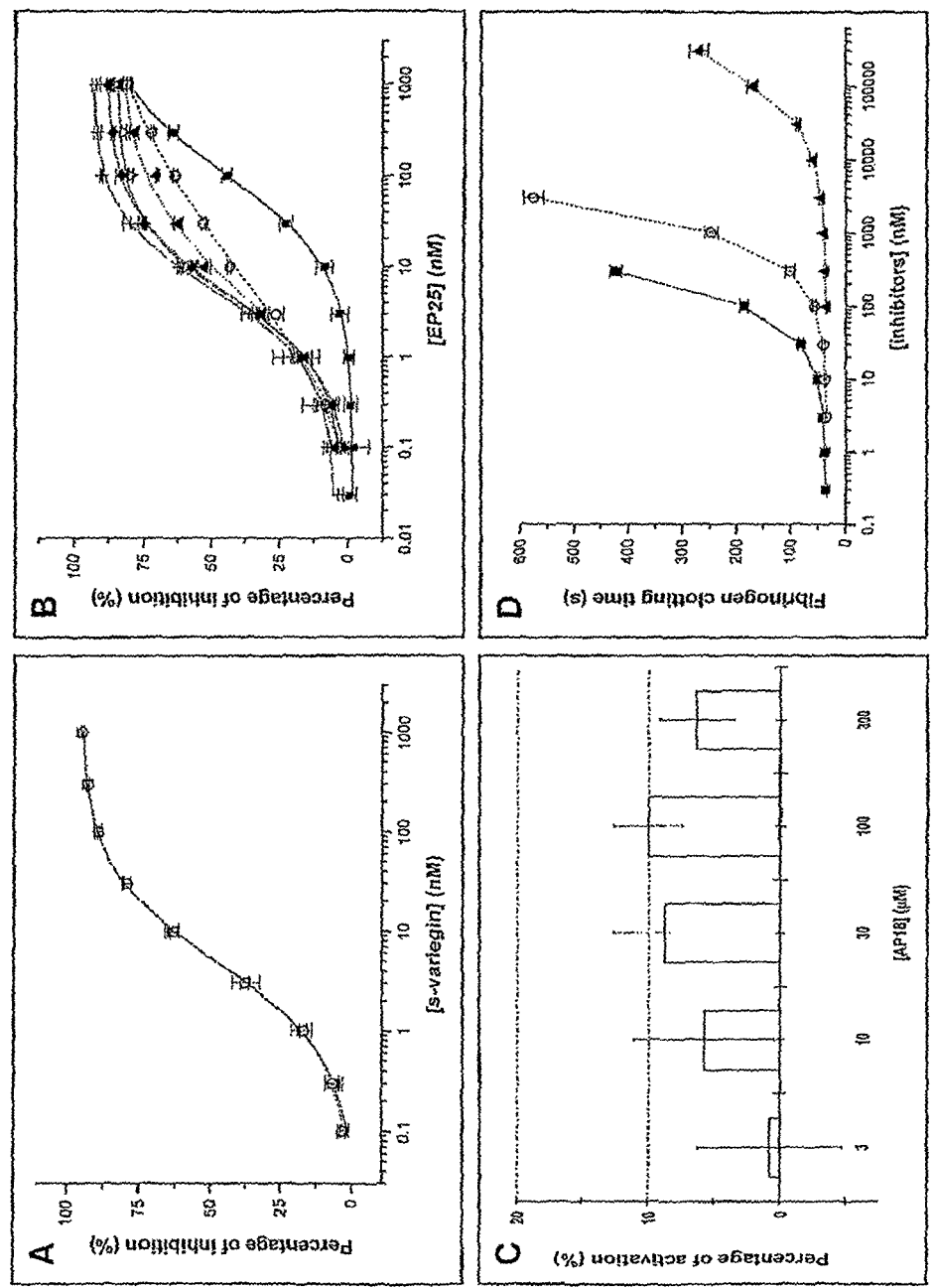

FIG. 4. Inhibition of thrombin by s-variegin, EP25 and AP18. (A) The ability of s-variegin, EP25 and AP18 to inhibit amidolytic activity of thrombin was assayed using active site directed substrate S2238 (100 μM). Dose response curve of thrombin (3.33 nM) inhibition by s-variegin (0.1 nM, 0.3 nM, 1 nM, 3 nM, 10 nM, 30 nM, 100 nM, 300 nM, 1000 nM) showed significant inhibition (~30%) for equimolar concentration of thrombin and variegin (3.33 nM). Dose-response curves and $IC_{50}$ of inhibition were independent of incubation time: (■) represents 10 min incubation ($IC_{50}$~5.40±0.95 nM) and (○) represents 10 min of incubation ($IC_{50}$~5.49±0.42 nM) (n=3). (B) Dose-response curves of thrombin (3.33 nM) inhibition by EP25 (0.1 nM, 0.3 nM, 1 nM, 3 nM, 10 nM, 30 nM, 100 nM, 300 nM, 1000 nM) showed an incubation time-dependent shift. $IC_{50}$ is ~139.30±7.02 nM without incubation (■), ~22.55±2.52 nM with 1 min incubation (○), ~10.39±1.53 nM with 2 min incubation (▲), ~6.42±0.50 nM with 5 min incubation (▽), ~6.80±0.57 nM with 10 min incubation (♦) and ~5.63±0.45 nM with 20 min of incubation (+) (n=3). (C) AP18 (3 μM, 10 μM, 30 μM, 100 μM, 300 μM) was unable to inhibit thrombin (3.33 nM) amidolytic activity on S2238 (100 μM); instead at high concentrations of AP18, hydrolysis of S2238 were slightly enhanced (n=3). (D) All three peptides, s-variegin (■); 0.3 nM, 1 nM, 3 nM, 10 nM, 30 nM 100 nM, 300 nM), EP25 (○; 3 nM, 10 nM, 30 nM, 100 nM, 300 nM, 1000 nM, 3000 nM) and AP18 (▲; 0.1 μM, 0.3 μM, 1 μM, 3 μM, 10 μM, 30 μM, 100 μM, 300 μM) prolonged fibrinogen clotting times (n=3). No pre-incubation of peptides with thrombin was carried out. AP18 inhibited thrombin fibrinogenolytic activity but not amidolytic activity, suggesting binding to exosite-I.

Figure 5:
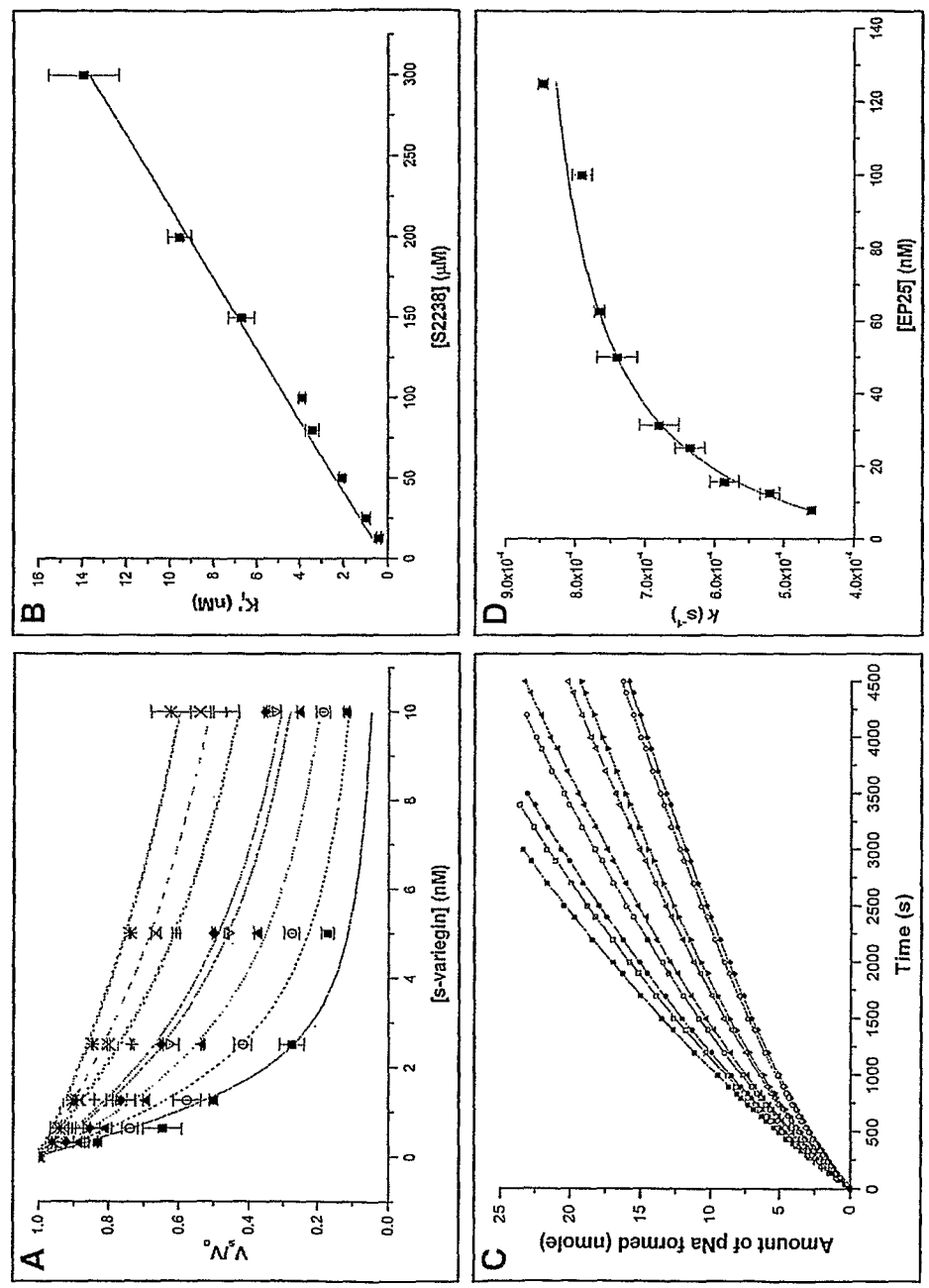

FIG. 5. Inhibitory constant $K_i$ of s-variegin and EP25. (A) S-variegin is a fast and tight binding inhibitor of thrombin. S-variegin (0.313 nM, 0.625 nM, 1.25 nM, 2.5 nM, 5 nM, 10 nM) was mixed with different concentrations of S2238: 12.5 μM (■), 25 μM (○), 50 μM (▲), 80 μM (▽), 100 μM (♦), 150 μM (+), 200 μM (×) and 300 μM (*) to determine $K_i'$. Reactions were started with the addition of thrombin (1.8 nM). Data were fitted to equation (1) (n=3) (B) Plot of $K_i'$ against substrate concentration showed a linear curve, indicating s-variegin competitively inhibited thrombin amidolytic activity on S2238. By fitting the data to equation (2), the inhibitory constant $K_i$ was shown to be ~146.4±13.6 pM. (C) Although EP25 also inhibited thrombin at equimolar concentrations if pre-incubated with thrombin, the initial inhibition without pre-incubation was weak. $K_i$ of EP25 was determined without pre-incubation with concentrations at least 8-fold greater than thrombin. Under these assay conditions, binding of EP25 to thrombin does not result in a significant depletion of free EP25 concentration, thus 'tight-binding' condition was not considered for data fitting. Progression curves of thrombin (0.9 nM) inhibition by different concentrations of EP25: 7.8 nM (■), 12.5 nM (□), 15.6 nM (●), 25 nM (○), 31.3 nM (▲), 50 nM (▽), 62.5 nM (▼), 100 nM (◇) and 125 nM (♦), using S2238 (100 μM) as substrate. The progression curves are non-linear, and showed two-phase equilibria typical of slow-binding inhibition. Data were fitted to equation (3) to obtain a k for each concentration of EP25 used (n=3). (D) Plot of the apparent first-order rate constant k against EP25 concentrations is a hyperbolic curve described by equation (4) and hence was fitted to the equation to obtain a $K_i'$ of ~529.7±76.7 pM, representing the dissociation constant of initial collision complex EI. The overall inhibitory constant $K_i$ was calculated from equation (5) and was found to be ~149.8±30.5 pM.

Figure 6:
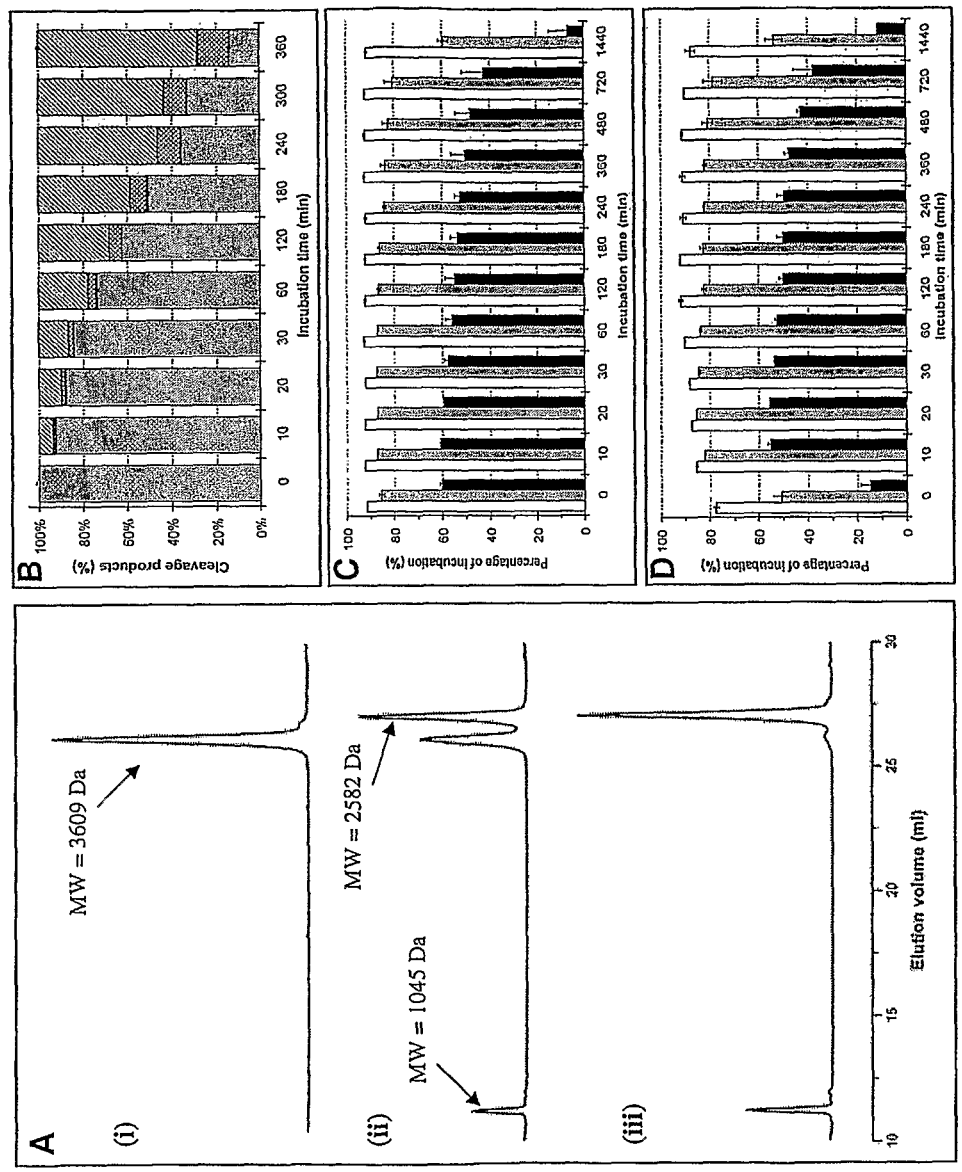

FIG. 6. Cleavage of s-variegin and EP25 by thrombin. (A) Typical chromatograms of HPLC analysis of s-variegin cleavage by thrombin at 37° C. (i) At incubation=0 min, the single peak correspond to uncleaved s-variegin. (ii) After 30 min incubation, two new peaks appeared corresponding to cleavage product of mass 1045 (representing N-terminal fragment SDQGDVAEPK (SEQ ID NO 2)) and of mass 2582 (representing C-terminal fragment MHKTAPPFDFEAIPEEYLDDES (SEQ ID NO 3)) while uncleaved s-variegin decreased in quantity. (iii) Cleavage is almost complete after 180 min incubation. (B) S-variegin (150 μM) was incubated with thrombin (5 μM) for various times at room temperature (n=2). S-variegin was present in 30-fold excess of thrombin. Cleavage of s-variegin by thrombin was analyzed with RP-HPLC. Relative percentage of uncleaved s-variegin (□), cleavage product of mass 1045 (representing N-terminal fragment SDQGDVAEPK) (SEQ ID NO 2) (▩) and cleavage product of mass 2582 (representing C-terminal fragment MHKTAPPFDFEAIPEEYLDDES) (SEQ ID NO 3) (▨) was calculated from the area under the peaks. (C) S-variegin was incubated with thrombin (3.33 nM) for up to 24 hr at room temperature and at various time points assayed for the ability to inhibit thrombin amidolytic activity on S2238 (100 μM). (D) Similar experiments were carried out replacing s-variegin with EP25. Concentrations of s-variegin or EP25: 10 nM (■), 100 nM (□) and 1000 nM (□) (n=2). At 100 nM of s-variegin or EP25, the inhibitors were also present in 30-fold excess of thrombin, and hence were used primarily for comparison with cleavage data from HPLC analysis.

Figure 7:
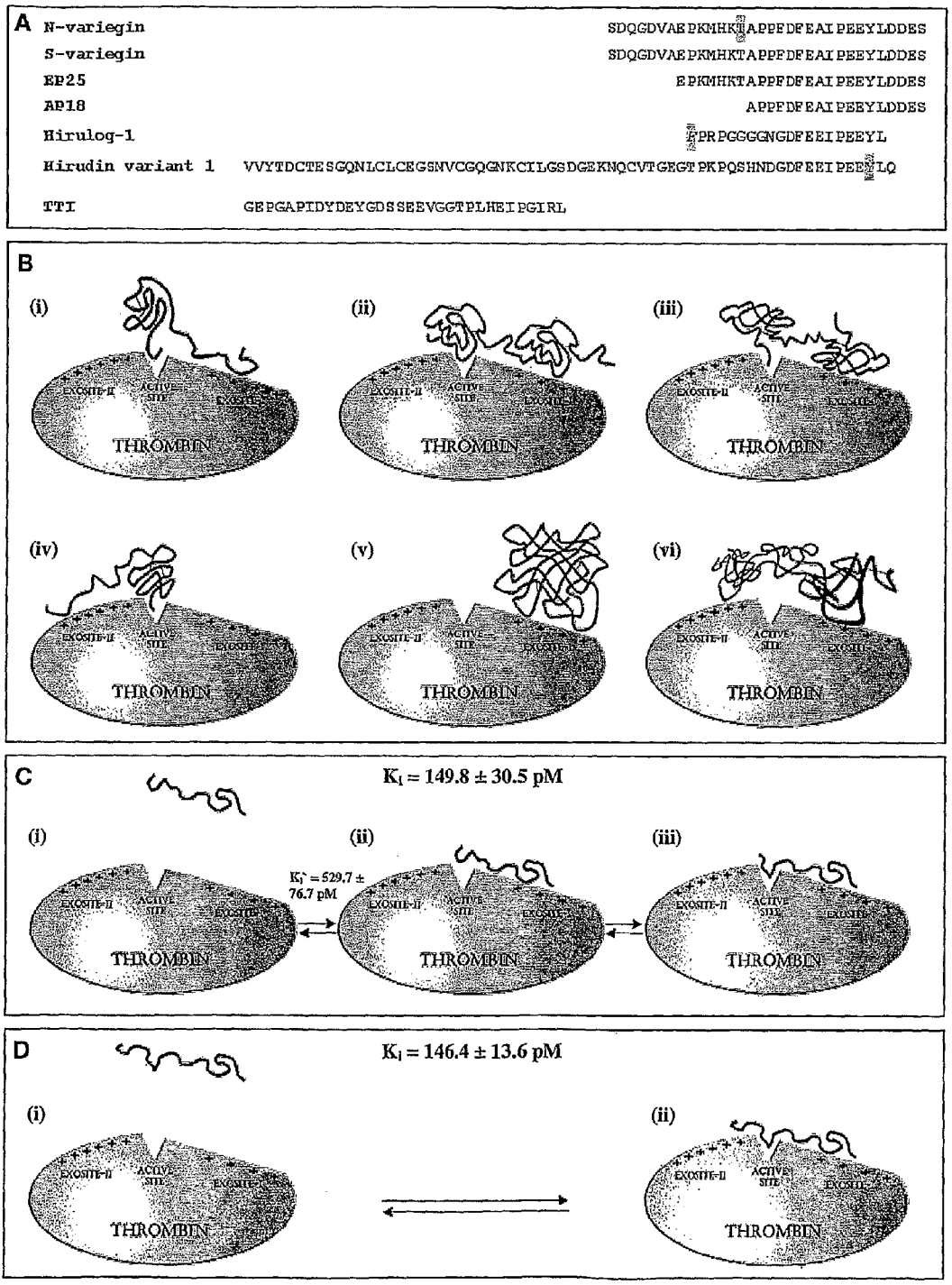

FIG. 7. Comparison of variegin with other thrombin inhibitors. (A) Amino acid sequence alignment of n-variegin, s-variegin, EP25, AP18, hirulog-1 and hirudin show highly similar C-terminal sequence. N-variegin is glucosylated at Thr (T), hirulog-1 contains a $_D$-Phe (F) and hirudin is sulfated at Tyr (Y). Sequence of TTI is distinctly different from variegin and was not aligned. (B) Schematic diagram showing different classes of thrombin inhibitors and their structural features. (i) Hirudin: compact N-terminus binds to active site, acidic and extended C-terminal binds to exosite-I; (ii) rhodniin: two Kazal-type domains in head-to-tail arrangement with the N-terminal domain binding to active site and the C-terminal domain binding to exosite-I; (iii) ornithodorin: two Kunitz-type domains in tail-to-tail arrangement with the N-terminal domain binding to active site and the C-terminal domain binds to exosite-I; (iv) haemadin: compact N-terminal domain binds to active site, acidic and extended C-terminus binds to exosite-II; (v) triabin: single β-barrel domain binds to exosite-I; (vi) bothrojaracin: two different chains of the C-type lectin domain bind to exosite-I and exosite-II respectively. Other prototypic thrombin inhibitors such as theromin and TTI are not represented due to lack of detailed structural information. (C) Proposed binding mechanism of EP-25 to thrombin: (i) electrostatic charges on C-terminus steer EP25 to thrombin and subsequently provide specific tethering interaction, (ii) without the steering effect of N-terminal residues (SDQGDVA (SEQ ID NO 18)) the active site binding moiety is not orientated properly to fit the thrombin active site, hence the initial collision complex (EI) has a higher $K_i$, and (iii) in a slow step the active site binding moiety (EPKMHKT (SEQ ID NO 19)) adopts the correct conformation for optimum binding and formation of a stabilized complex. (D) Proposed binding mechanism of variegin to thrombin: (i) complementary electrostatic charges between variegin N-terminus and thrombin exosite-II as well as between variegin C-terminus and thrombin exosite-I steer variegin to thrombin, (ii) all electrostatic interactions occurred rapidly and pre-orient active site binding moiety (EPKMHKT (SEQ ID NO 19)) in correct conformation for fast binding to thrombin active site.

Figure 8:
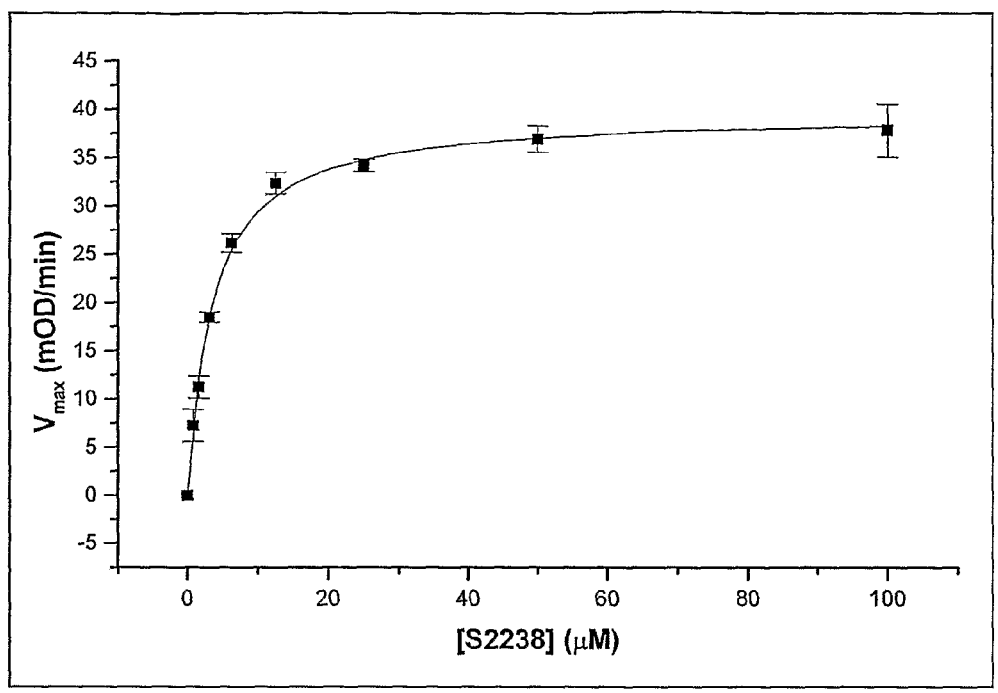

FIG. 8. Plot of reaction velocity ($V_{max}$) as a function of substrate (S2238) concentration following the Michaelis-Menton equation. $K_m$ calculated with Michaelis-Menton equation is determined to be 3.25±0.56 µM, similar to reported values[33,34].

Figure 9:
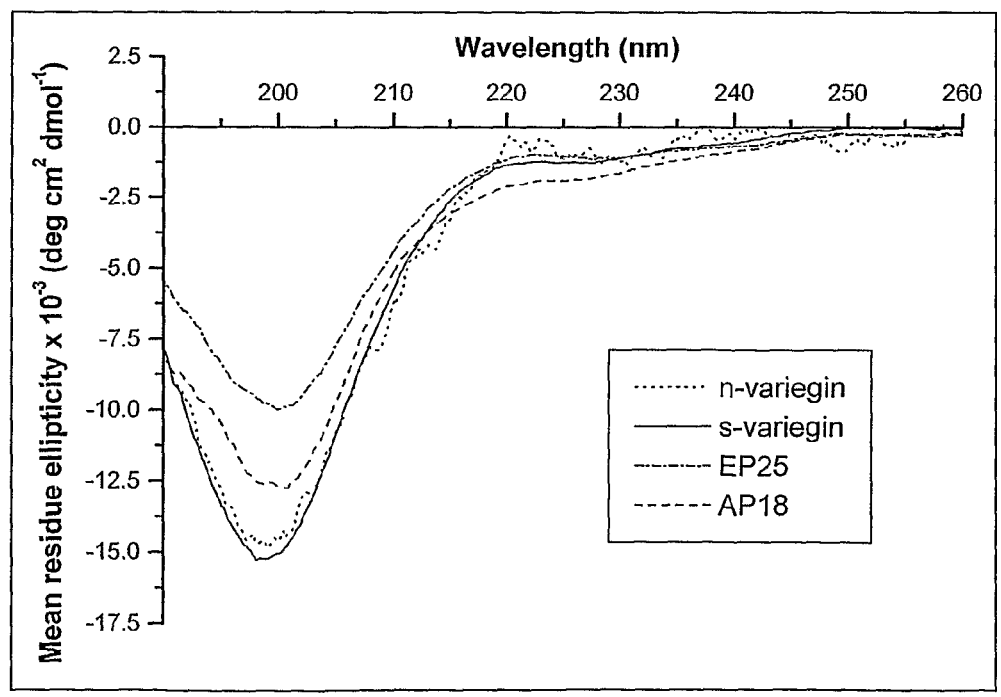

FIG. 9. Far-UV spectra (260-190 nm) of n-variegin, s-variegin, EP25 and AP18 dissolved in 10 mM of sodium phosphate buffer (pH7.4). All spectra were typical of a random coil protein.

Figure 10:
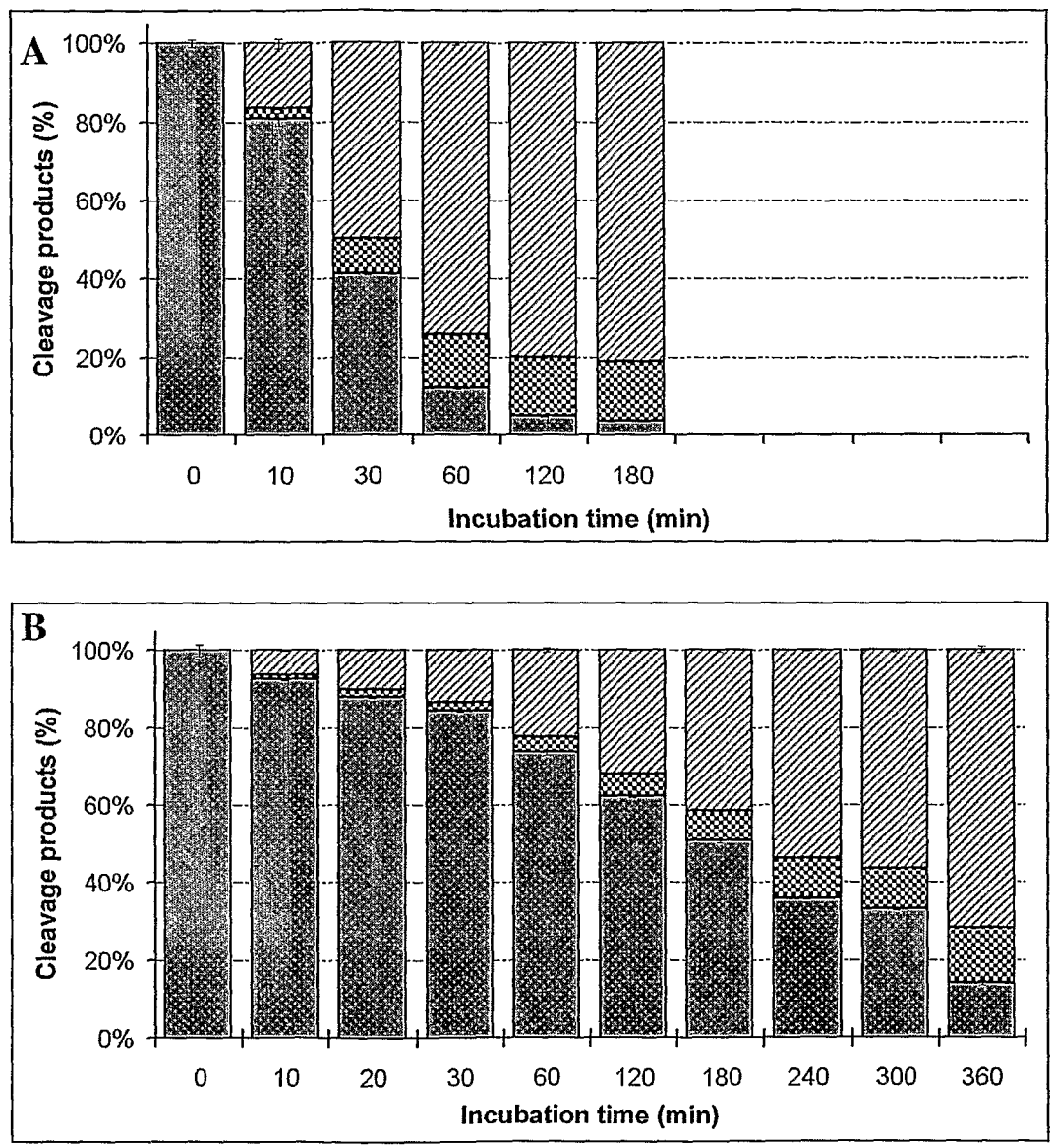

FIG. 10. RP-HPLC analysis showed that s-variegin was cleaved by thrombin at 37° C. and room temperature. (A) S-variegin (150 µM) was incubated with thrombin (5 µM) for various time at 37° C. (n=2). (B) S-variegin (150 µM) was incubated with thrombin (5 µM) for various time at room temperature (n=2). Relative percentages of uncleaved S-variegin (□), cleaved product of mass 1045 (representing N-terminal fragment SDQGDVAEPK (SEQ ID NO 2)) (▨) and cleavage product of mass 2582 (representing C-terminal fragment MHKTAPPFDFEAIPEEYLDDES) (SEQ ID NO 3) (▤) were calculated from the area under the peaks in the chromatograms.

Figure 11:
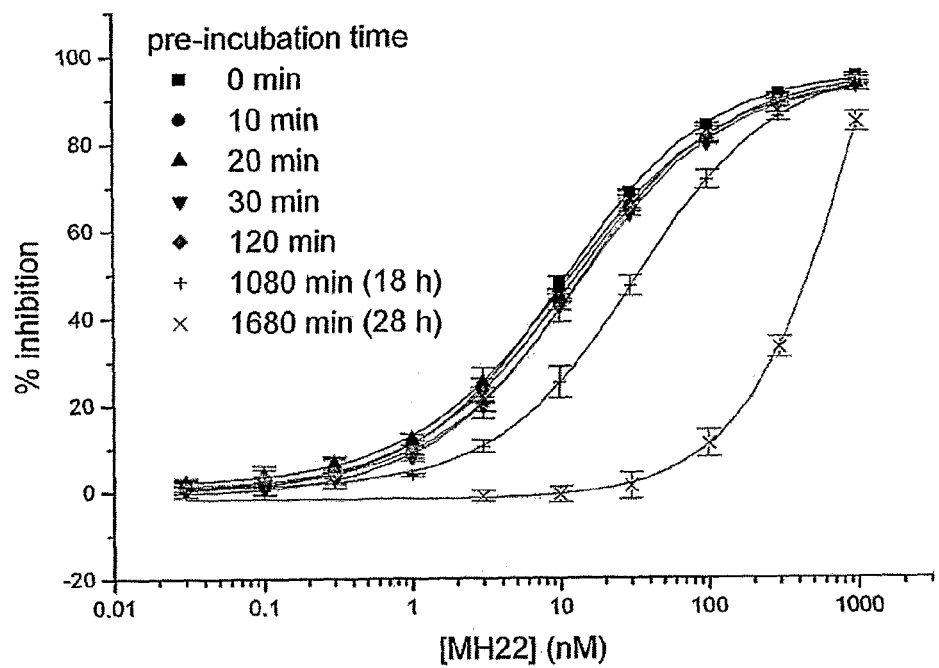

FIG. 11. Thrombin inhibitory activity of C-terminal fragment MHKTAPPFDFEAIPEEYLDDES (MH22) (SEQ ID NO 3) of variegin The ability of various concentrations of MH22 to inhibit thrombin amidolytic activity using active site directed substrate S2238 following incubation with thrombin at room temperature for 0 min (■), 10 min (●), 20 min (▲), 30 min (▼), 120 min (◆), 1080 min (+) or 1680 min (×) was assessed.

Figure 12:
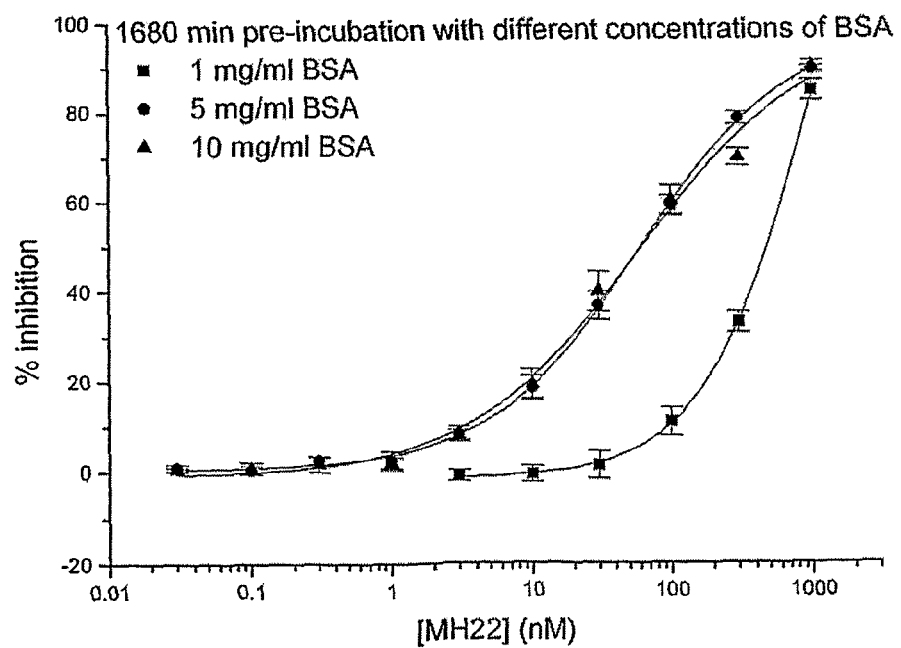

FIG. 12. Reversal of decrease in amidolytic activity of MH22. The decrease in the amidolytic activity of MH22 after prolonged incubation with thrombin (1680 min pre-incubation $IC_{50}$=479.7±16.1 nM) can be reversed by including increased concentrations of BSA (1 mg/ml (■), 5 mg/ml (●), 10 mg/ml) (▲) in the assay setup.

Figure 13:
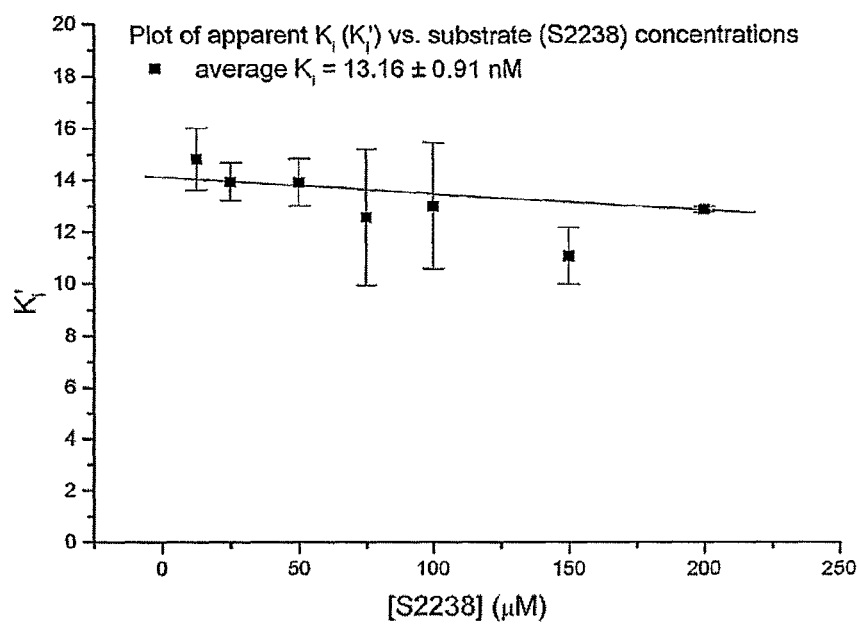

FIG. 13. Ki of MH22. The $K_i'$ of MH22 at different concentrations of substrate (S2238) was determined through the equation describing fast and tight binding. $K_i'$ did not change significantly throughout the concentration range used (12.5 nM to 200 nM), indicating that MH22 is a non-competitive inhibitor of thrombin amidolytic activity. $K_i'=K_i$ and the average $K_i$ was found to be 13.2±0.91 nM.

Figure 14:
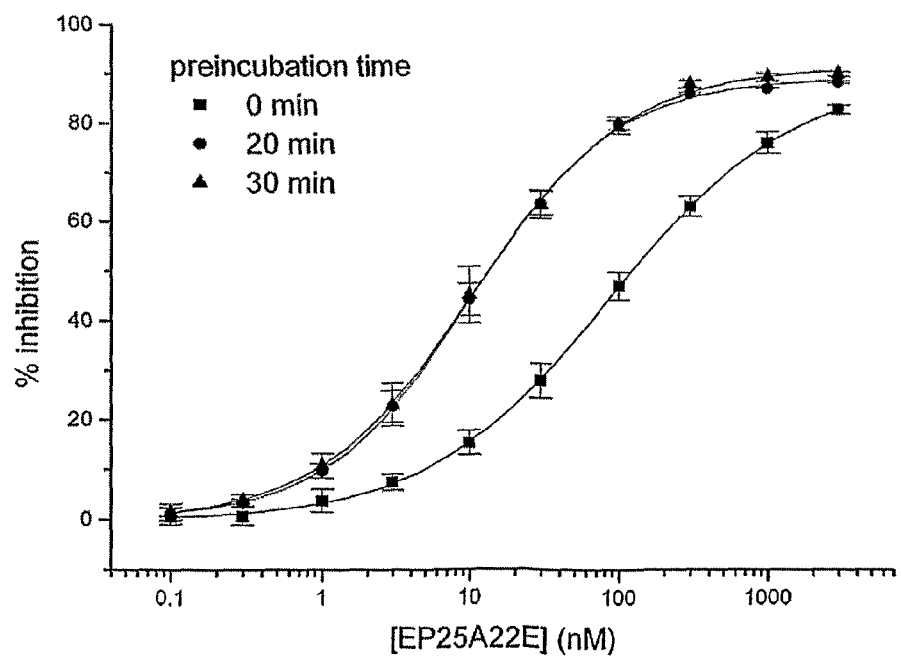

FIG. 14. Thrombin inhibitory activity of variegin mutant fragment EP25A22E. The ability of various concentrations of EP25A22E having the sequence EPKMHKTAPPFDFE E IPEEYLDDES (SEQ ID NO 7) to inhibit thrombin amidolytic activity using active site directed substrate S2238 following incubation with thrombin at room temperature for 0 min (■), 20 min (●) or 30 min (▲) was assessed. In EP25A22E, alanine 22 in s-variegin (alanine 15 in EP25) was replaced with glutamic acid since glutamic acid is present in the same position in hirudin.

Figure 15:
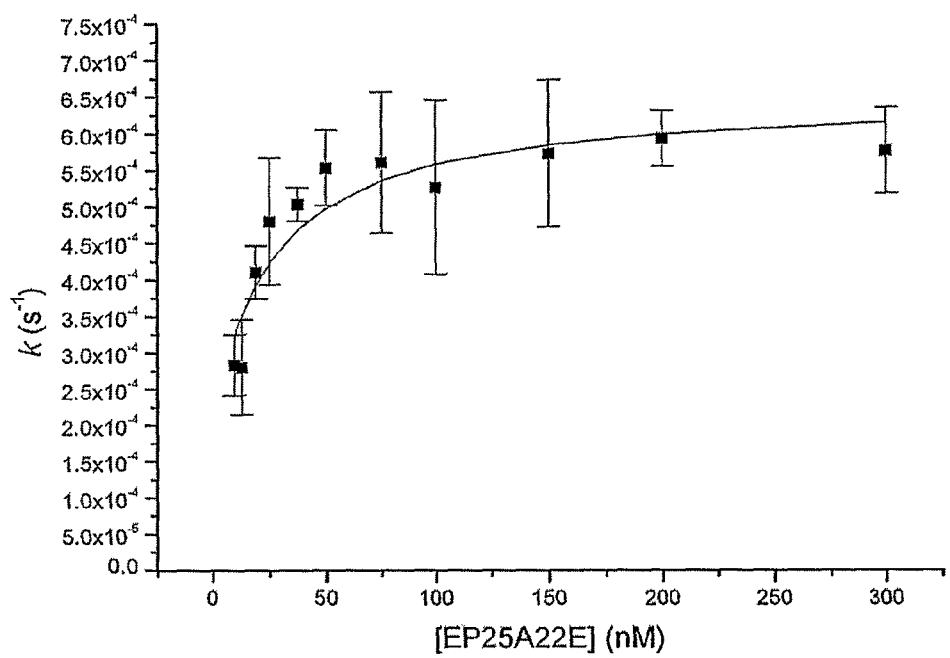

FIG. 15. Ki of EP25A22E. The $K_i$ of EP25A22E was determined using the slow binding inhibitor equation and was found to be 0.311±0.070 nM.

Figure 16:
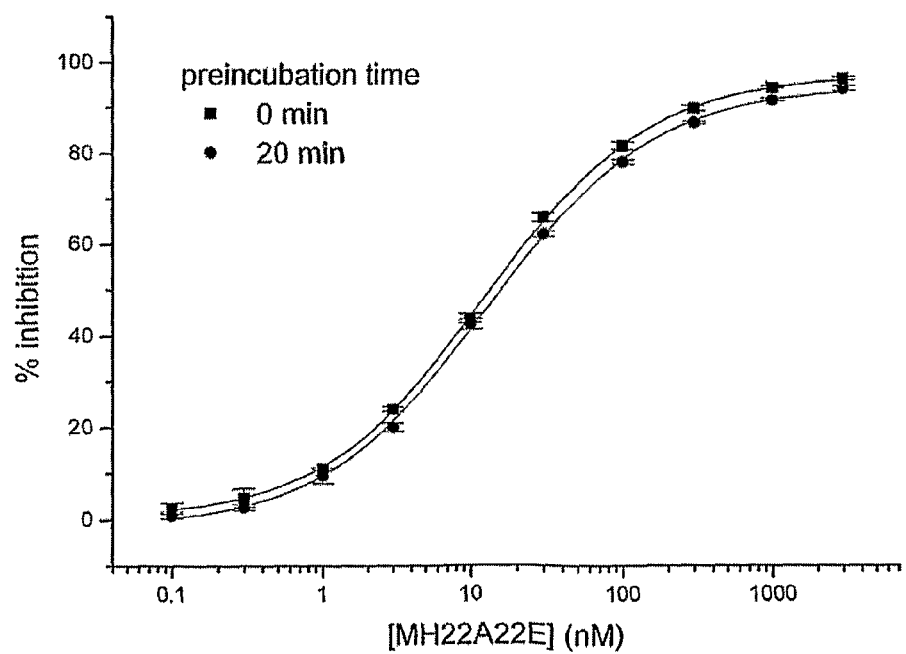

FIG. 16. Thrombin inhibitory activity of variegin mutant fragment MH22A22E. The ability of various concentrations of MH22A22E having the sequence MHKTAPPFDFE E IPEEYLDDES (SEQ ID NO 5) to inhibit thrombin amidolytic activity using active site directed substrate S2238 following incubation with thrombin at room temperature for 0 min (■) or 20 min (●) was assessed. MH22A22 is the C-terminal cleavage fragment of EP25A22E.

Figure 17:
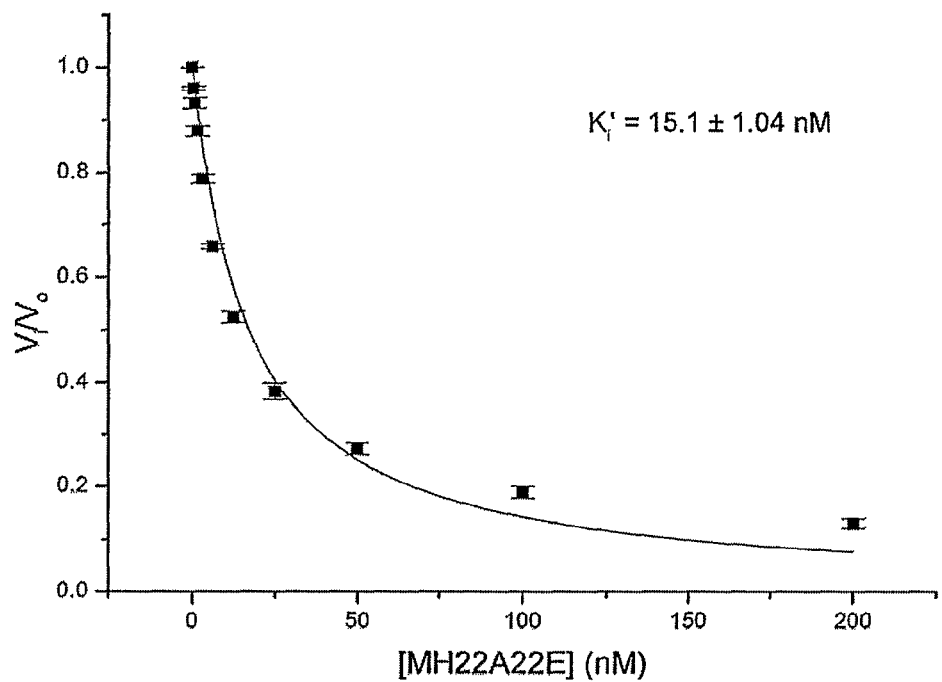

FIG. 17. Ki of MH22A22E MH22A22E has a $K_i'$ of 15.1±1.04 nM when tested with 100 µM of substrate (S2238).

Figure 18:
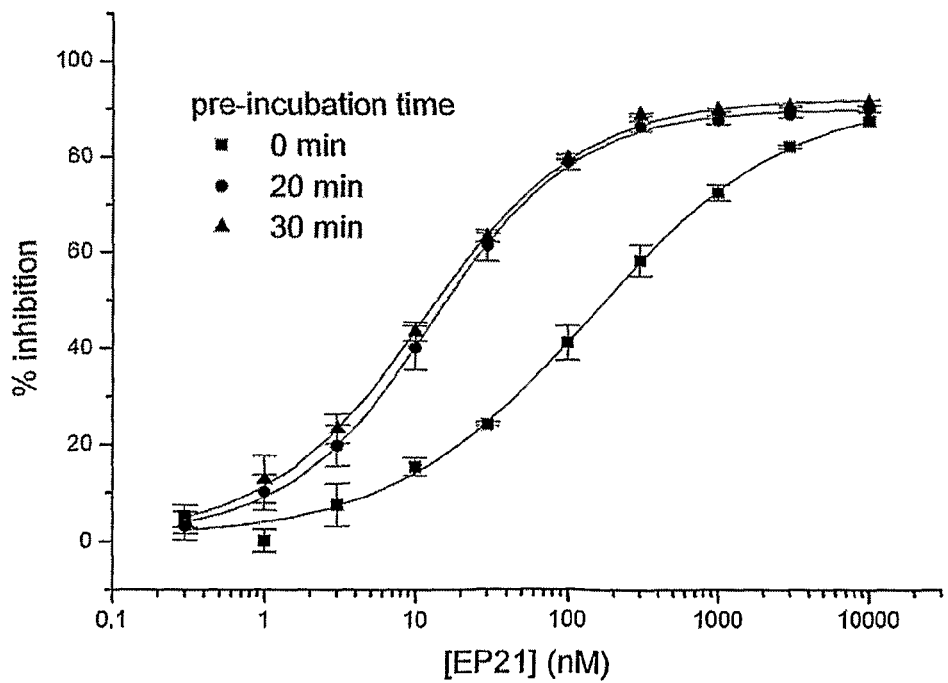

FIG. 18. Thrombin inhibitory activity of variegin fragment EP21. The ability of various concentrations of EP21 EPKMHKTAPPFDFEAIPEEYL (SEQ ID NO 8) to inhibit thrombin amidolytic activity using active site directed substrate S2238 following incubation with thrombin at room temperature for 0 min (■), 20 min (●) or 30 min (▲) was assessed. EP21 corresponds to EP25 except that it is missing four residues at the C-terminal.

Figure 19:
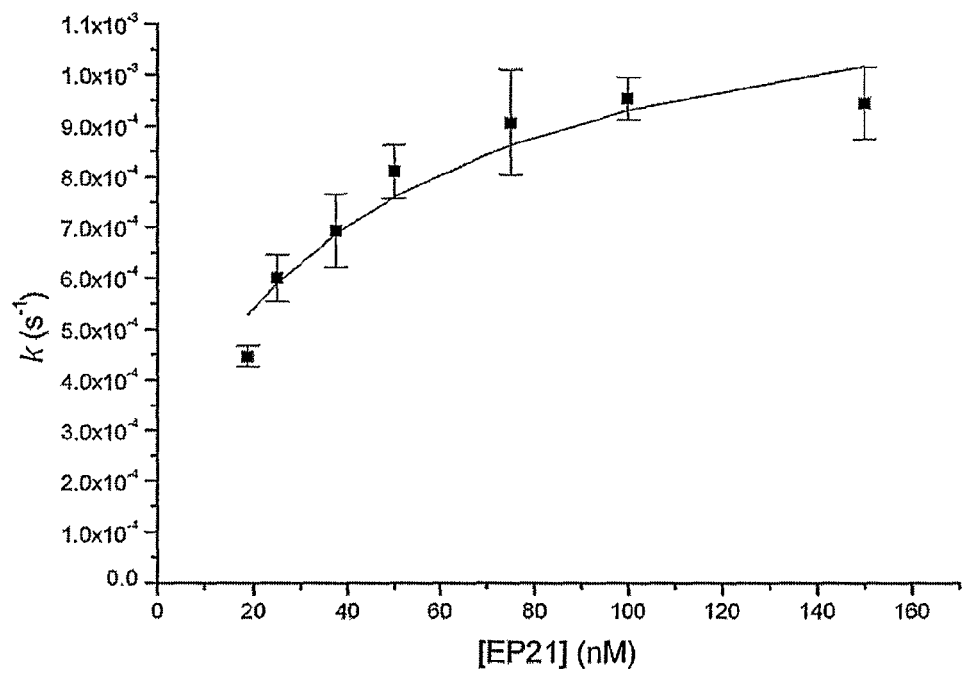

FIG. 19. Ki of EP21. $K_i$ of EP21, determined by slow binding equations was found to be 0.315±0.024 nM.

Figure 20:
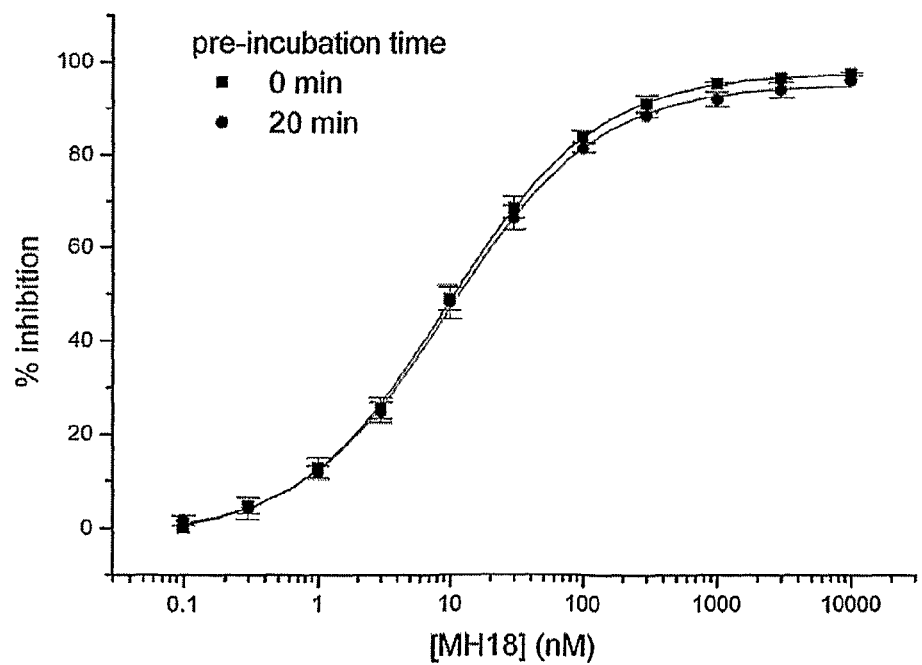

FIG. 20. Thrombin inhibitory activity of variegin fragment MH18. The ability of various concentrations of MH18 MHKTAPPFDFEAIPEEYL (SEQ ID NO 20) to inhibit thrombin amidolytic activity using active site directed substrate S2238 following incubation with thrombin at room temperature for 0 min (■) or 20 min (●) was assessed. MH18 corresponds to MH22 except that it is missing four residues at the C-terminal.

Figure 21:
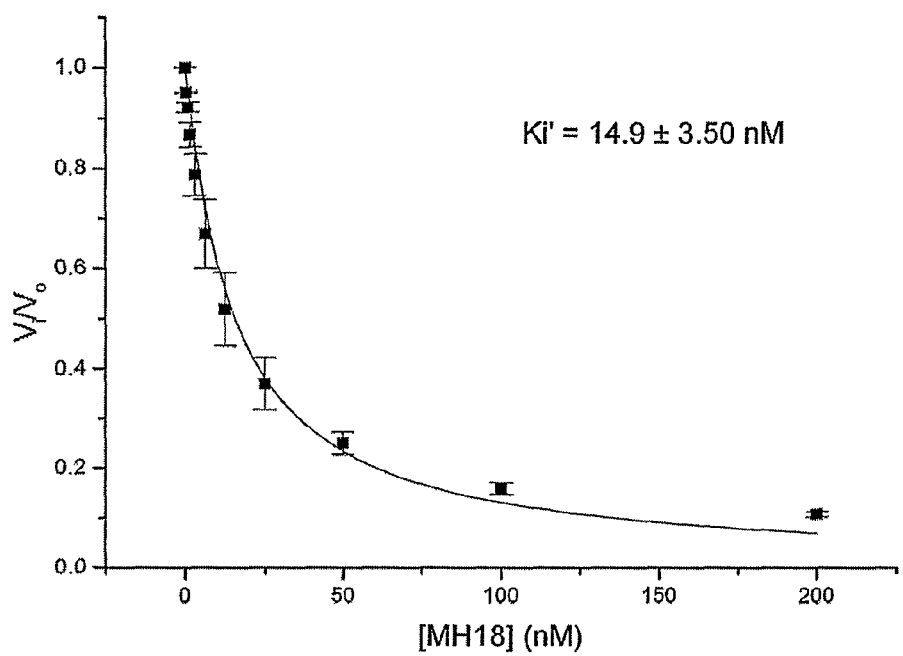

FIG. 21. Ki of MH18. Using fast and tight binding equation, $K_i'$ of MH18 at 100 µM substrate (S2238)=14.9±3.50 nM. Assuming the removal of four residues at the C-terminal did not alter the inhibition mechanism, MH18 is also a non-competitive inhibitor with $K_i$=14.9±3.50 nM.

Figure 22:
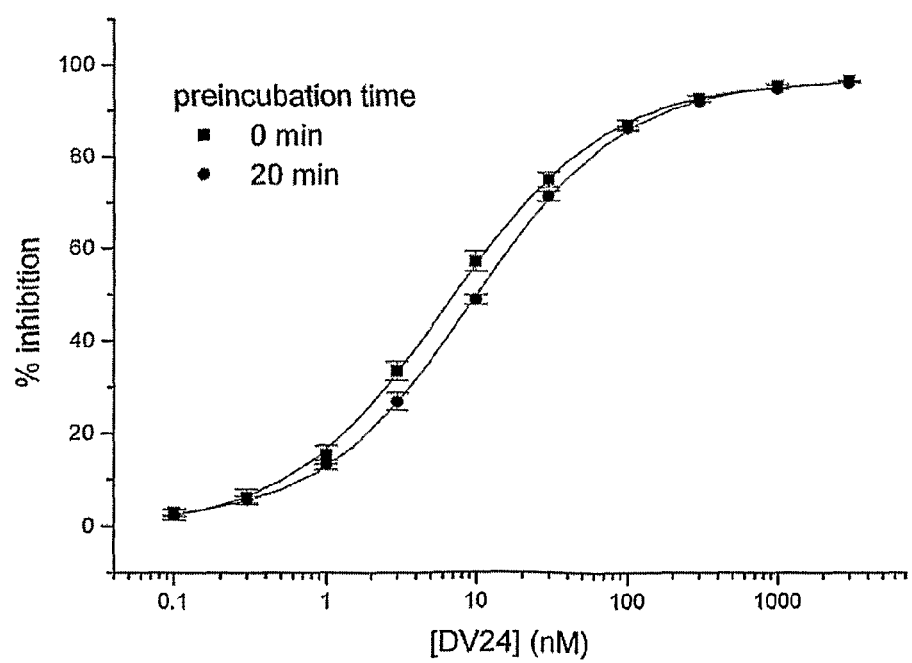

FIG. 22. Thrombin inhibitory activity of variegin fragment DV24. The ability of various concentrations of DV24 DVAEPKMHKTAPPFDFEAIPEEYL (SEQ ID NO 9) to inhibit thrombin amidolytic activity using active site directed substrate S2238 following incubation with thrombin at room temperature for 0 min (■) or 20 min (●) was assessed. DV24 corresponds to EP21 except that it contains an additional 3 residues at the N-terminal.

Figure 23:
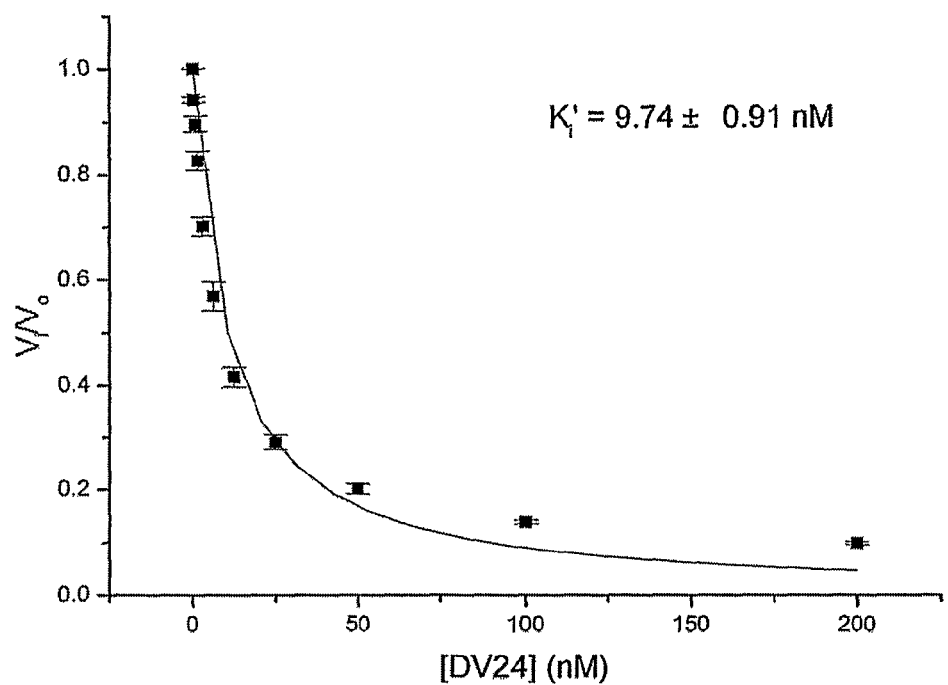

FIG. 23. Ki of D24. $K_i'$ of DV24 at 100 µM substrate (S2238)=9.74±0.91 nM and $K_i$ of DV24 was determined to be 0.306±0.029 nM, FIG. 24. Thrombin inhibitory activity of variegin mutant fragment DV24K10R. The ability of various concentrations of DV24K10R DVAEP R MHKTAPPFDFEAIPEEYL (SEQ ID NO 10) to inhibit thrombin amidolytic activity using active site directed substrate S2238 following incubation with thrombin at room temperature for 0 min (■) or 20 min (●) was assessed. DV2424K10R corresponds to DV24 except that it contains an arginine instead of a lysine at position 6 (amino acid 10 is variegin).

Figure 25:
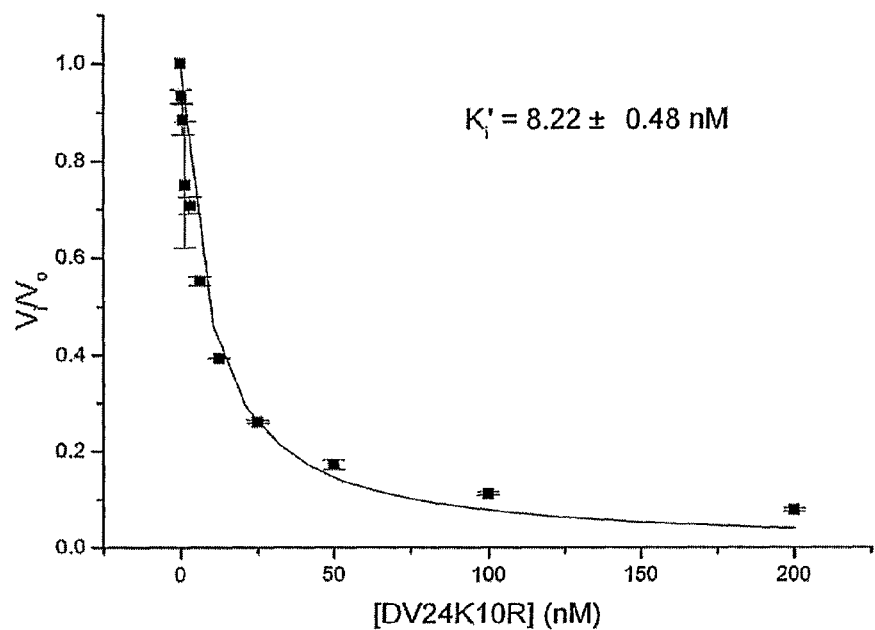
Figure 26:
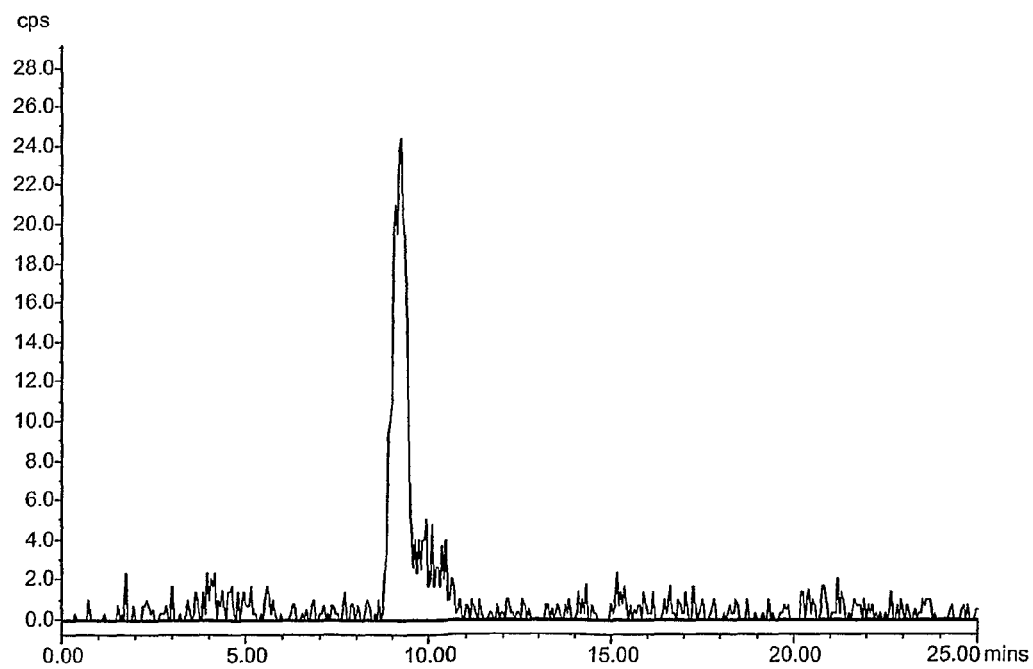

FIG. 25. Ki of DV24K10R. The $K_i$ of DV24K10R was determined to be 0.259±0.015 nM FIG. 26. HPLC radiochromatogram to show [³H]-Variegin dose solution FIG. 27. Distribution of radioactivity in tissues at 30 minutes following a single intravenous administration of [³H]-Variegin to a male albino rat (0.4 mg/kg). Levels 1 to 5 refer to successive 1 cm longitudinal sections through the rat body.

Figure 28:
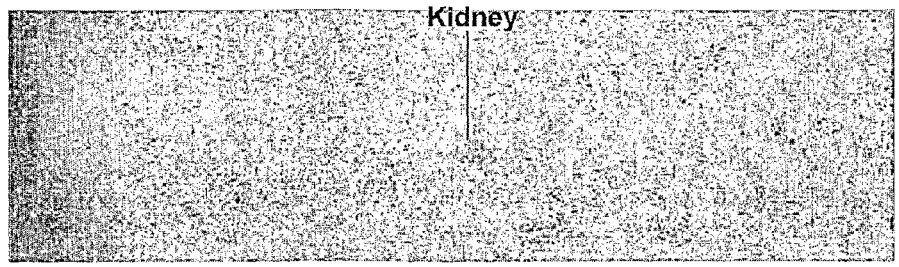
Figure 28:
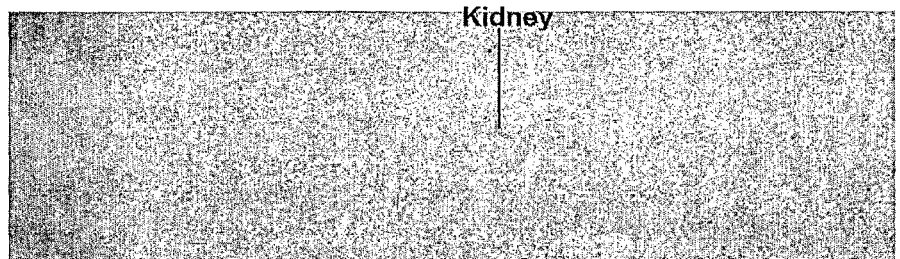
Figure 28:
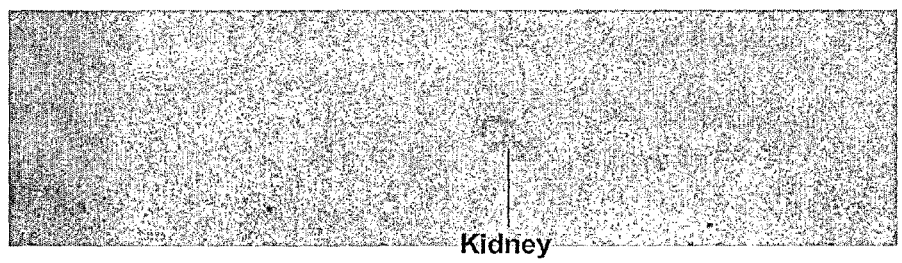
Figure 28:
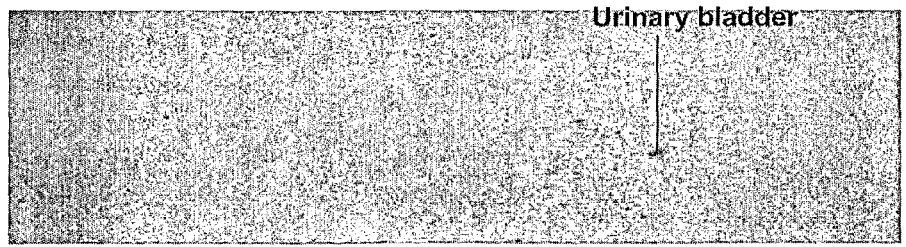
Figure 28:
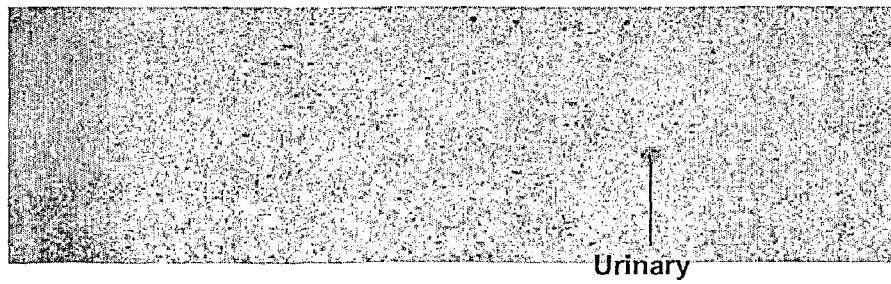

FIG. 28. Distribution of radioactivity in tissues at 1 hour following a single intravenous administration of [³H]-Variegin to a male albino rat (0.4 mg/kg). Levels 1 to 5 refer to successive 1 cm longitudinal sections through the rat body.

Figure 29:
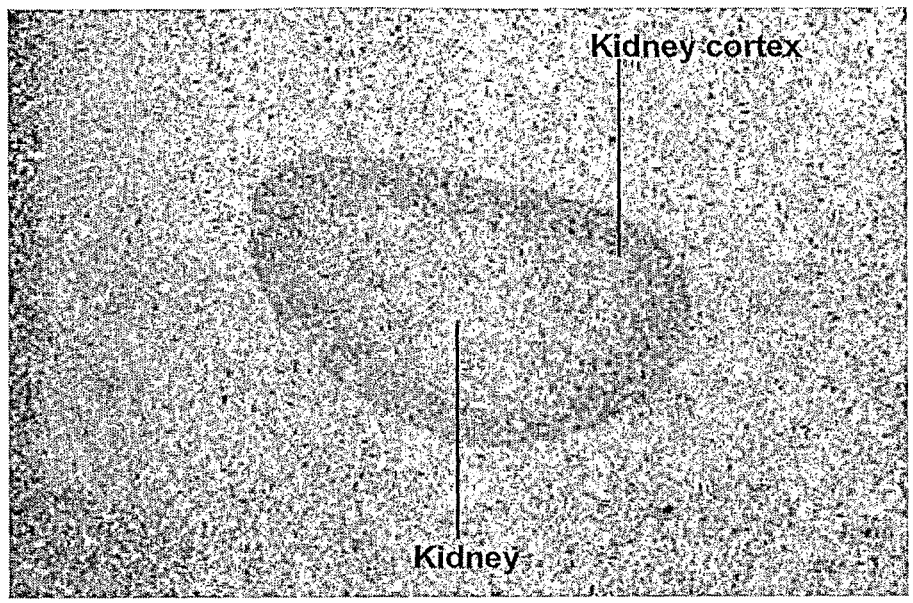
Figure 29:
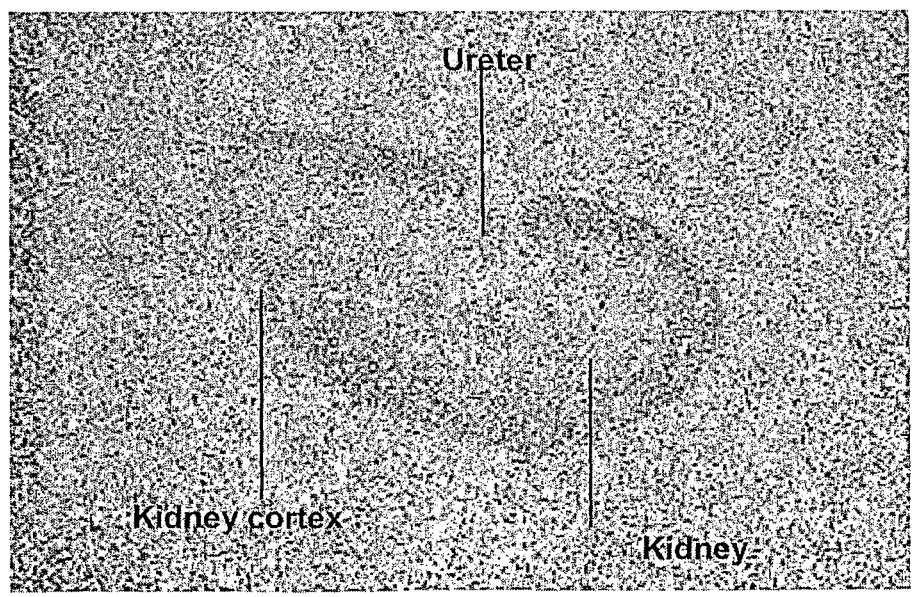

FIG. 29. Distribution of radioactivity in the kidney at 30 minutes following a single intravenous administration of [³H]-Variegin to a male albino rat (0.4 mg/kg)

EXAMPLES

Example 1

Analysis of Variegin and EP25

Material and Methods
Materials

Human citrated plasma was provided by the Department of Hematology and Transfusiology of the Slovak Institute of Cardiovascular Diseases. Thromboclotin reagent was from Dade AG (Düdingen, Switzerland). Thromboplastin IS reagent and Actin FS Activated PTT reagent were from Dade International Inc. (Miami, Fla.). 9-Fluorenylmethyloxycarbonyl (Fmoc)-L-amino acids, Fmoc-PEG-PS support resin, N,N-dimethylformamide (DMF), 20% v/v piperidine in DMF, O-(7-azabenzotriazol-1-yl)-1,1,3,-3-tetramethyluronium hexafluorophosphate (HATU) and N,N-diisopropylethylamine (DIPEA) were from Applied Biosystems (Foster City, Calif.). Trifluoroacetic acid (TFA), 1,2-ethanedithiol, thioanisole, bovine chymotrypsin and bovine serum albumin (BSA), were from Sigma Aldrich (St. Louis, Mo.). Human fibrinogen, FXIIa, tissue plasminogen activator (TPA), urokinase, kalikrein and bovine trypsin were from Merck Chemicals Ltd. (Nottingham, UK). Human factor IXa (FIXa), factor Xa (FXa), factor XIa (FXIa), APC and plasmin were from Hematologic Technologies, Inc. (Essex Junction, Vermont). Human factor VIIa (FVIIa) and recombinant α-thrombin were gifts from the Chemo-Sero-Therapeutic Research Institute (KAKETSUKEN, Japan)[21,22]. Chromogenic substrates S2222, S2238, S2251, S2288, S2302, S2366, S2444, S2586 and S2765 were from Chromogenix (Milano, Italy). Spectrozyme® FIXa was from American Diagnostica Inc. (Stamford, Conn.). All other chemicals and reagents used were of analytical grade.

Salivary Gland Extracts and Estimation of Protein Concentrations

The extraction procedure of *A. variegatum* SGE and estimation of protein concentrations during fractionation were described previously[23]

Purification of Variegin Isoforms

Figure 1B:
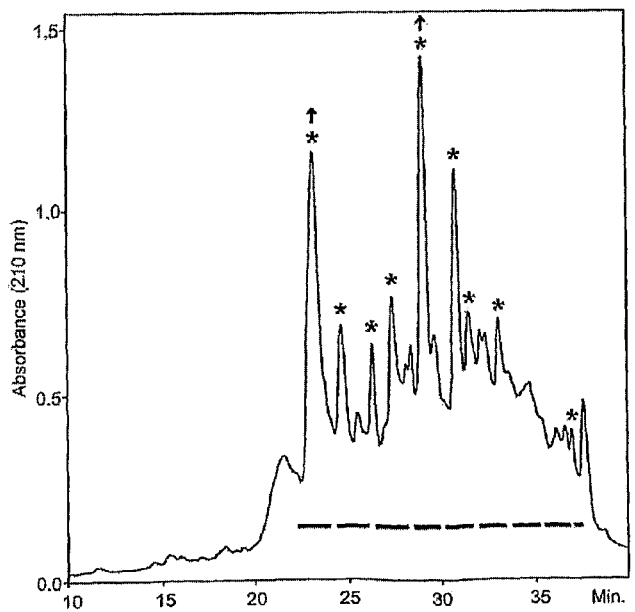
Figure 1C:
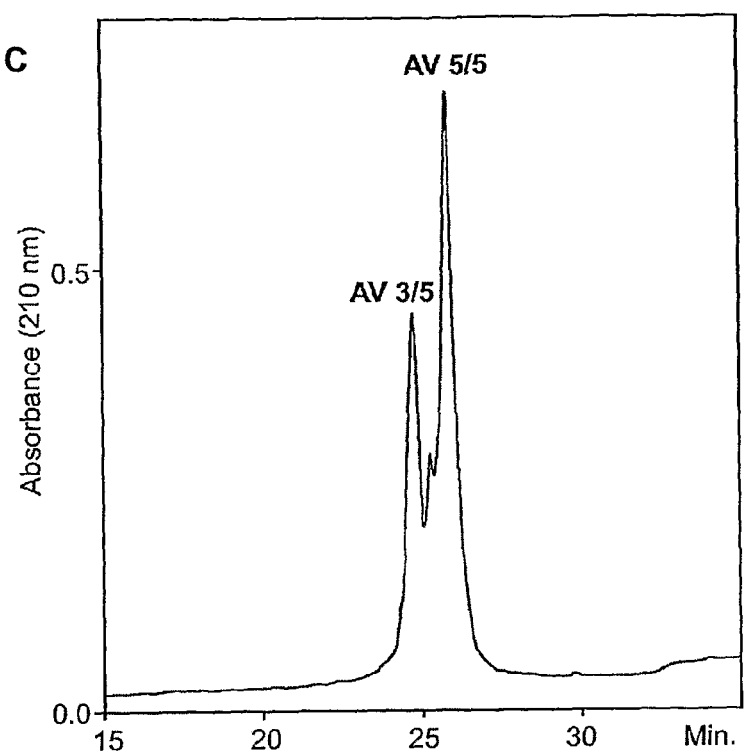
Figure 1D:
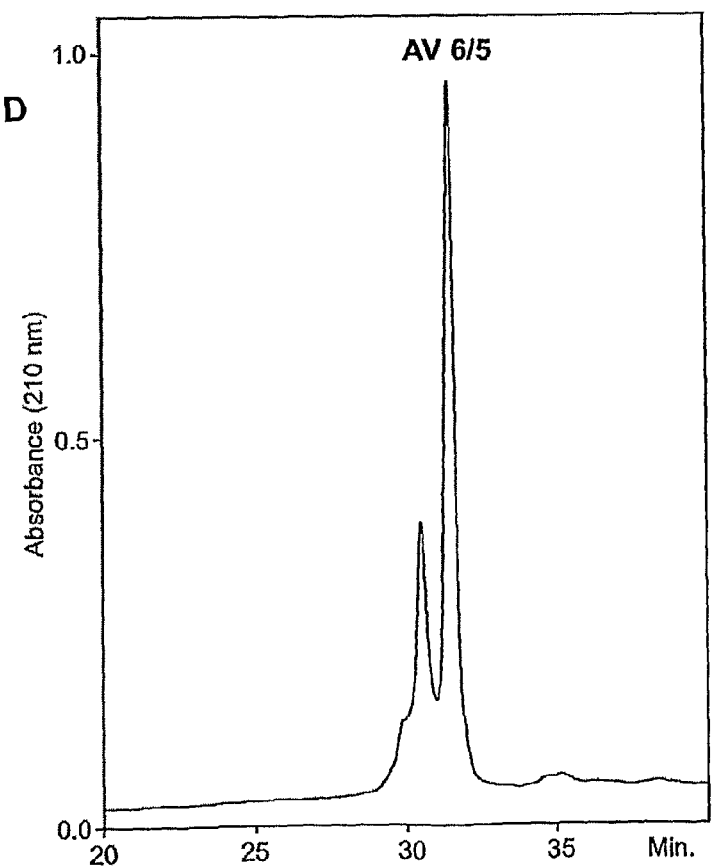

Variegin was purified by a three-step reverse-phase HPLC procedure with a Beckman Instruments 126/168 DAD HPLC system (Fullerton, Calif.). In the first step (FIG. 1A) SGE was loaded onto a Vydac C-4 (5 µm; 250×4.6 mm) column (Grace Vydac, Hesperia, Calif.). Pooled fractions that contained the strongest anticoagulant activity (FIG. 1A, fraction AV-III) were subjected to a second step (FIG. 1B) using a Beckman Ultrasphere C-18 (5 µm; 250×4.6 mm) column. Lastly, individual fractions were further purified using a Vydac C-18 (5 µm; 250×4.6 mm) column to obtain three fractions of potent anti-thrombin activity: AV 6/5, AV 3/5 and AV 5/5 (FIG. 1C-D). The major component in the AV 6/5 fraction was named variegin.

Coagulation Assays

Thrombin time (TT), prothrombin time (PT) and activated partial thromboplastin time (APTT) assays were used for the initial screens of anticoagulant activities in SGE and fractions. Citrated human plasma (50 µl) was pre-incubated with a maximum of 5 µl of the SGE or the same volume of 150 mM NaCl (control) at 37° C. for 1 min. After adding the corresponding reagents (TT: 50 µl of Thromboclotin reagent; PT: 100 µl of Thromboplastin IS reagent; APTT: 50 µl of Actin FS Activated PTT added for 3 min and reaction started with 50 µl of 20 mM $CaCl_2$), times required for the formation of fibrin clots were determined visually using a stop watch.

The activities of crude SGE and the three fractions (AV 6/5, AV 3/5 and AV 5/5) were verified at the Oxford Hemophilia Centre of Churchill Hospital (Oxford, UK). TT, PT and APTT were performed using an MDA-180 analyser (Organon Teknika Ltd., Cambridge, UK). 10 µl of SGE or diluted fractions containing AV 6/5, AV 3/5 and AV 5/5 were added to 290 µl of platelet poor plasma, mixed and incubated for 5 min at 37° C. The activities were also verified using a Thromboelastograph Analyzer (Haemoscope Inc., Skokie, Ill.). Five µl of samples were added to 335 µl of citrated whole blood, incubated for 5 min and the sample run on the TEG following recalcification.

Protein Sequence Analysis

The molecular weight of proteins present in AV 6/5, AV 3/5 and AV 5/5 were determined by Eurosequence (Groningen, the Netherlands) using a BIFLEX (Bruker-Franzen, Bremen, Germany) matrix-assisted laser desorption/ionization reflectron time-of-flight (MALDI-TOF) mass spectrometer equipped with a nitrogen laser (337 nm) and gridless delayed extraction ion source. Partial amino acid sequences were determined by N-terminal Edman-degradation using an automated sequencer (Model 494, Applied Biosystems). The complete sequence for AV 6/5 was determined by MALDI-MS analysis.

Peptide Synthesis and Purification

Three peptides (s-variegin, EP25 and AP18) were synthesized using solid phase peptide synthesis methods on an Applied Biosystems Pioneer Model 433A Peptide Synthesizer. Fmoc groups of amino acids were removed by 20% v/v piperidine in DMF and coupled using HATU/DIPEA in situ neutralization chemistry. All peptides were synthesized on preloaded PEG-PS resins. Cleavage by a cocktail of TFA/1, 2-ethanedithiol/thioanisole/water released peptide acids (—COOH). Synthetic peptides were purified by RP-HPLC on ÄKTA™ purifier (GE Healthcare, Uppsala, Sweden) with a SunFire™ C18 (5 µm; 250 mm×10 mm) (Waters, Milford, Mass.) column. The purity and mass of all peptides were determined by electrospray ionization mass spectrometry (ESI-MS) using a Perkin-Elmer Sciex API 300 LC/MS/MS System (Perkin-Elmer Sciex, Selton, Conn.).

Circular Dichroism (CD) Spectroscopy

Far-UV CD spectra (260-190 nm) of variegin, s-variegin, EP25 and AP18 dissolved in 10 mM of sodium phosphate buffer (pH 7.4) were recorded using a Jasco J-810 spectropolarimeter (Easton, Md.). All measurements were carried out at room temperature using 0.1 cm path length cuvettes with a scan speed of 50 nm/min, a resolution of 0.2 nm and a bandwidth of 2 nm.

Inhibition of Thrombin Amidolytic Activity

All assays for thrombin amidolytic activity on S2238 were performed in 96-wells microtiter plates in 50 mM Tris buffer (pH 7.4) containing 100 mM NaCl and 1 mg/ml BSA at room temperature. Typically, 100 µl of peptides and 100 µl of thrombin were pre-incubated for different durations before the addition of 100 µl of S2238. The rates of formation of colored product p-nitroaniline were followed at 405 nm for 10 min with an ELISA plate reader. Percentage inhibition was calculated by taking the rate of increase in absorbance in the absence of inhibitor as 0%. Dose-response curves were fitted using Origin software (MicroCal, Northampton, Mass.) to calculate $IC_{50}$ values.

Determination of the Inhibitory Constant $K_i$

The inhibitory constant, $K_i$, was determined using S2238 as substrate. When an enzyme is inhibited by an equimolar concentration of inhibitor, the binding of inhibitor to enzyme causes a significant depletion in the concentration of free inhibitors. This tight-binding inhibition is described by the following equation[24]:

$$V_s=(V_o/2E_t)\{[(K_i'+I_t-E_t)^2+4K_i'E_t]^{1/2}-(K_i'+I_t-E_t)\} \quad (1)$$

where $V_s$ is steady state velocity, $V_o$ is velocity observed in the absence of inhibitor, $E_t$ is total enzyme concentration, $I_t$ is total inhibitor concentration and $K_i'$ is apparent inhibitory constant. For competitive inhibition, $K_i$ is related to $K_i'$ by equation (2):

$$K_i'=K_i(1+S/K_m) \quad (2)$$

where Ki' increases linearly with S, $K_i$ is the inhibitory constant, S is the concentration of substrate and $K_m$ is the Michaelis constant for S2238 (determined to be 3.25±0.56 μM, FIG. 8, similar to reported values[24,25]). Both variegin and s-variegin were found to be tight-binding inhibitors. The data were fitted to these equations using Origin software.

If the rate of interaction of the inhibitor with the enzyme is slow so that the inhibited steady-state velocity is slowly achieved, the progress curve of product formation of this slow binding inhibition is described by equation (3)[26]:

$$P=V_st+(V_o-V_s)(1-e^{-kt})/k+P_o \quad (3)$$

where P is the amount of product formed, $P_o$ is initial amount of product, $V_s$ is final steady state velocity, $V_o$ is initial velocity, t is time, and k is apparent first-order rate constant.

There are two possible minimum kinetic mechanisms to describe such slow binding reactions[26,27]:

Scheme (1):

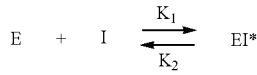

where E is enzyme, I is inhibitor and EI* is stable enzyme-inhibitor complex, $K_1$ is association rate constant and $K_2$ is dissociation rate constant. In this scheme, slow binding is mainly due to the slow $K_1$. The apparent first-order rate constant k will increase linearly with inhibitor concentration. Alternatively:

Scheme (2):

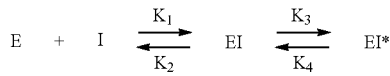

where EI is initial collision complex, $K_3$ is forward isomerization rate and $K_4$ is reverse isomerization rate. In this scheme, binding involves rapid formation of an initial collision complex (EI) that subsequently undergoes slow isomerization to the final enzyme-inhibitor complex (EI*). k increases hyperbolically with inhibitor concentrations. Dissociation constant of EI (denoted $K_i'$) can be calculated from equation (4):

$$k=K_4+K_3I_t/[I_t+K_i'(1+S/K_m)] \quad (4)$$

The overall inhibitory constant $K_i$ can be calculated from equation (5):

$$K_i=K_i'[K_4/(K_3+K_4)] \quad (5)$$

EP25 was found to be a slow binding inhibitor following the Scheme 2 mechanism. The data were fitted to these equations using Origin software.

Serine Protease Specificity

The selectivity profile of variegin was examined against 13 serine proteases: fibrinolytic serine proteases (plasmin, TPA and urokinase), anticoagulant serine protease APC, procoagulant serine proteases (FXIIa, FXIa, FXa, FIXa, FVIIa, kallikrein and thrombin) and classical serine proteases (chymotrypsin and trypsin). Effects of s-variegin on these serine proteases were determined by inhibition of their amidolytic activities assayed using specific chromogenic substrates.

Fibrinogen Clotting Time

The abilities of s-variegin, EP25 and AP18 to prolong fibrinogen clotting time were tested using a BBL fibrometer (BD, Franklin Lakes, N.J.). 200 μl of fibrinogen (final concentration 3 mg/ml) were incubated with 100 μl of peptides (various concentrations) at 37° C. Clotting of fibrinogen was initiated by the addition of 100 μl of thrombin (final concentration 20 nM). All reagents and samples were dissolved in 50 mM Tris buffer (pH 7.4) containing 100 mM NaCl.

Cleavage of s-Variegin by Thrombin

S-variegin and EP25 (final concentrations: 150 μM) were incubated with thrombin (final concentration: 5 μM) at both room temperature and 37° C. After various incubation times, the reactions were quenched with 0.1% TFA buffer (pH 1.8) and loaded onto a SunFire™ C18 column attached to an ÄKTA™ purifier. New peaks other than those present in the chromatogram of 0 min incubation were identified as cleavage products and subjected to ESI-MS to verify their masses. The peaks were integrated to calculate the area under the peaks and relative percentage of each peak.

Results

Purification of Variegin Isoforms

Crude SGE of *A. variegatum* exhibited potent anticoagulant activity in all three coagulation assays (PT, APTT and TT) (FIG. 9). Potency was in the order TT>>APTT>PT, indicating that SGE is a promising source of potent thrombin inhibitor(s). To purify this inhibitor(s), SGE was fractionated by RP-HPLC (FIG. 1A). After the first step of purification, the most potent anticoagulant fraction (AV-III) was subjected to a second purification step (FIG. 1B). The resulting fractions were screened for antithrombin activity in coagulation and chromogenic substrate assays. Two fractions with the strongest activity (retention time 23.083 and 28.933 min) were further purified in separate runs. The fraction with retention time 23.083 min was separated into two main peaks denoted AV 3/5 and AV 5/5 (FIG. 1C). The fraction with retention time 28.933 has one main peak and with a small 'shoulder peak' and was denoted AV 6/5 (FIG. 1D). The anticoagulant activities of these three fractions (AV 3/5, AV 5/5 and AV 6/5) along with crude SGE were verified by PT, APTT, TT and TEG assays. All four assays revealed that AV 6/5 contained the most potent anticoagulant activity, followed by AV 3/5 and AV 5/5 (Table 1).

TABLE 1

Anticoagulation activities of *Amblyomma variegatum* SGE (females fed for 9 days). Results show the mean of duplicate values. In controls 150 mM NaCl was substituted for SGE.

|  | TT (s) | APTT (s) | PT (s) |
|---|---|---|---|
| Control | 17 | 28 | 15 |
| SGE protein (μg) |  |  |  |
| 0.025 | 50 |  |  |
| 0.05 | 105 |  |  |
| 0.10 | >180 |  |  |

TABLE 1-continued

Anticoagulation activities of *Amblyomma variegatum* SGE (females fed for 9 days). Results show the mean of duplicate values. In controls 150 mM NaCl was substituted for SGE.

|      | TT (s) | APTT (s) | PT (s) |
|------|--------|----------|--------|
| 0.25 |        | 28       | 15     |
| 0.50 |        | 38       | 19     |
| 1.00 |        | 45       | 22     |
| 2.50 |        | >180     | 40     |
| 5.00 |        |          | >180   |

Protein Sequence Analysis

Partial sequences of all three fractions were determined by Edman degradation. For AV 6/5 the sequence and molecular weight were completed by MALDI-TOF. MALDI spectrum of AV 6/5 revealed a major m/z signal of 3769.96 Da (monoisotopic mass=3768.96 Da) and a minor m/z signal of 3777.79 Da (monoisotopic mass=3776.79 Da). The main component has the sequence SDQGDVAEPKMHKT(hex)APPFDFEAIPEEYLDDES (SEQ ID NO 1), where the Thr14 is modified by a hexose moiety. This was named variegin and was further characterized. The minor component (3776.79 Da) is almost identical to variegin, with Glu31 replaced by His. Partial sequences determined by Edman degradation revealed two components in the AV 3/5 fraction (m/z 3953.54 and 3409.57 Da) and three components in AV 5/5 (m/z 3680.23, 3368.94 and 3173.62 Da). All the sequences determined are highly similar to variegin (FIG. 2A). CD spectrum of variegin is typical of a random coil protein (Table 2).

TABLE 2

Anticoagulation activities of *A. variegatum* SGE and RP-HPLC fractions. AV 6/5 is the most potent fraction determined in all assays. The major component in AV 6/5 was sequenced and named variegin. Since APTT, PT and TT were performed in citrated platelet poor plasma (PPP), and thus represent a non-physiological milieu in which to assess its anticoagulant potential, the activity of the samples were also verified with TEG, which permits coagulation monitoring in whole blood using viscoelastic assessment of clot formation as an endpoint. (PNP: pooled normal plasma; r: r phase, the period of time of latency from the time that blood was placed in the TEG until the initial fibrin formation; k: k phase, a measure of the speed to reach a certain level of clot strength).

| Sample        | TEG                 | PT (s)  | APTT (s) | TT (s)  |
|---------------|---------------------|---------|----------|---------|
| Crude SGE     | Complete inhibition | No clot | No clot  | No clot |
| PNP           | Normal              | 13.6    | 25.6     | 12.2    |
| AV 6/5        | Inhibited           | —       | —        | —       |
| 1:200 dilution|                     | 15.3    | 59.2     | 78.9    |
| 1:500 dilution|                     | 14.4    | 48.3     | 39.2    |
| AV 3/5        | Prolonged r/k       | —       | —        | —       |
| 1:200 dilution|                     | 14.1    | 46.7     | 30.8    |
| 1:500 dilution|                     | 14.1    | 38.8     | 20.6    |
| AV 5/5        | Prolonged r/k       | —       | —        | —       |
| 1:200 dilution|                     | 13.8    | 38.5     | 21.4    |
| 1:500 dilution|                     | 13.8    | 33.7     | 15.6    |

BLAST results indicate that variegin does not show similarity to any known proteins in the database. Interestingly, its C-terminus (DFEAIPEEYL) (SEQ ID NO 21) is almost identical to the C-terminus of hirudin (residues 55 to 64: DFEEIPEEYL (SEQ ID NO 22)). Thus, we hypothesized that variegin C-terminus plays a similar role to hirudin C-terminus in binding to thrombin. However, Tyr63 of hirudin is sulfated[28,29] while the corresponding Tyr in variegin is not.

Inhibition of Thrombin Amidolytic Activity by Variegin and its $K_i$

The ability of variegin to inhibit thrombin amidolytic activity was assayed with S2238, a small peptidyl substrate that binds only to the active site. Variegin inhibited the amidolytic activity and progress curves of inhibition showed that steady state equilibrium was achieved upon mixing (FIG. 2B). Significant inhibition (~80%) was observed for equimolar concentrations of thrombin and variegin (3.33 nM). $IC_{50}$ of the inhibition is ~0.99±0.02 nM (FIG. 2C). Variegin is a fast and tight-binding competitive inhibitor of thrombin with a $K_i$ of ~10.4±1.4 pM (FIG. 2D).

Synthesis of s-Variegin and Variants

For further characterization, three peptides were synthesized, purified and characterized. Synthetic variegin (SDQGDVAEPKMHKTAPPFDFEAIPEEYLDDES (SEQ ID NO 1), s-variegin) has the complete sequence of variegin, while EP25 (EPKMHKTAPPFDFEAIPEEYLDDES) (SEQ ID NO 6) and AP18 (APPFDFEAIPEEYLDDES) (SEQ ID NO 16) have seven and 14 residues truncated from the N-terminus. Unlike native variegin (n-variegin) Thr is not glycosylated in s-variegin and EP25. CD spectra of s-variegin, EP25 and AP18 are all similar to that of n-variegin, typical of random coil proteins (FIG. 9).

Specificity of Inhibition by Variegin

To determine the specificity, s-variegin was screened against 13 serine proteases including thrombin. Apart from thrombin, no other serine proteases showed significant inhibition (≤5%) even at 1 μM of s-variegin. Inhibition of >10% was observed at much higher concentrations of s-variegin. The most susceptible proteases are plasmin, trypsin and FXIa, which were inhibited ~20 to 30% by 100 μM of s-variegin. In contrast, against thrombin, similar ~30% inhibition was observed at a concentration at least 4 orders of magnitude lower (~3.3 nM) (FIG. 3). Therefore, s-variegin is a specific and potent thrombin inhibitor.

Inhibition of Thrombin Amidolytic Activity by s-Variegin, EP25 and AP18

S-variegin is similar to n-variegin in that steady state equilibrium of inhibition was achieved upon mixing. It was 5-fold less active than n-variegin and ~30% inhibition was observed at equimolar concentrations of thrombin and s-variegin (3.33 nM). Dose-response curves showed an $IC_{50}$ value of 5.40±0.95 nM, independent of incubation time (0 min and 10 min) (FIG. 4A). Hence, s-variegin is also a fast and tight binding inhibitor of thrombin. The absence of Thr glycosylation in s-variegin might account for its weaker activity.

EP25 also inhibited amidolytic activity of thrombin. However, unlike n-variegin and s-variegin, progress curves of inhibition showed two-phase equilibria in the absence of pre-incubation. The steady state equilibrium inhibition was achieved relatively slowly after ~10 min pre-incubation. Dose-response curves of EP25 were dependent on incubation times. Thus the deletion of seven N-terminal residues (SDQGDVA (SEQ ID NO 18)) turned the binding mode from fast to slow. However, potency of EP25 was not affected by the deletion. When the final steady state equilibrium was achieved (20 min pre-incubation) EP25 inhibited thrombin to the same extent as s-variegin ($IC_{50}$ values for EP25 and s-variegin are 5.63±0.45 nM and 5.40±10.95 nM, respectively) (FIG. 4B).

In contrast, AP18 did not inhibit thrombin amidolytic activity even at 300 μM, suggesting that it did not bind to the active site. Instead, AP 18 enhanced thrombin amidolytic activity slightly in a dose-dependent manner (FIG. 4C). This is consistence with the reported behavior of hirudin C-terminus[28]. In summary, these results suggest that the active site binding moiety on variegin resides within position 8 to 14 (EPKMHKT).

Inhibition of Thrombin Fibrinogenolytic Activity

S-variegin, EP25 and AP18 all prolonged fibrinogen clotting time in a dose-dependent manner (FIG. 4D). Fibrinogen binds to both the active site and exosite-I of thrombin[1,2]. AP18 inhibited fibrinogenolytic but not amidolytic activity of thrombin, and hence we concluded that C-terminus of variegin binds to exosite-I. This observation is consistence with that of hirudin C-terminus[28,29]. The difference in activity between s-variegin and EP25 is likely to be due to the slow binding mode of EP25.

Inhibitory Constant $K_i$ of s-Variegin and EP25

$K_i$ of s-variegin and EP25 was determined using S2238 as substrate. S-variegin is a fast and tight binding inhibitor. $K_i'$ was determined in the presence of different concentrations of S2238 (FIG. 5A). S-variegin is a competitive inhibitor of thrombin and its $K_i'$ increased linearly with increasing concentrations of S2238 (equation 2) (FIG. 5B). The true inhibitory constant, $K_i$ was found to be ~146.4±13.6 pM, which is 14-fold higher than n-variegin (~10.4±1.4 pM). In contrast, EP25 is a slow binding inhibitor of thrombin. Progress curves of inhibition were fitted to equation 3 to obtain k for each concentration of EP25 (FIG. 5C). k, the apparent first-order rate constant for the establishment of the equilibrium between initial collision complex (EI) and final stable complex (EI*), increased hyperbolically with EP25 concentration (FIG. 5D), as described by Scheme (2). Thus, the binding between EP25 and thrombin involves the isomerization of EI to EI*. The dissociation constant of EI ($K_i'$, equation 4) was ~529.7±76.7 pM, while the overall inhibitory constant $K_i$ (equation 5) was ~149.8±30.5 pM. Thus, $K_i$ of EP25 is essentially the same as $K_i$ of s-variegin (~146.4±13.6 pM). These results confirmed that the deletion of seven N-terminal residues did not affect potency but switched the binding mode from fast to slow.

Cleavage of s-Variegin by Thrombin

Since variegin binds to the thrombin active site, it may be cleaved by thrombin, similar to other serine protease inhibitors[30]. Therefore we examined the cleavage of s-variegin by thrombin and its effects on inhibition. RP-HPLC analysis showed that s-variegin was indeed cleaved by thrombin at room temperature and 37° C. At 0 min of incubation only peaks corresponding to uncleaved s-variegin and thrombin were present. Two new peaks of cleavage products appeared and increased with increasing incubation time (FIG. 6A). These new peaks had molecular weights of 1045 Da (SDQGDVAEPK (SEQ ID NO 2)) and 2582 Da (MHKTAPPFDFEAIPEEYLDDES (SEQ ID NO 3)) respectively, and corresponded to cleavage at the Lys10-Met11 peptide bond. Cleavage proceeded faster at 37° C. than at room temperature (FIG. 9).

To verify the effect of variegin cleavage, s-variegin and EP25 were incubated with thrombin up to 24 h and at various time points assayed for the ability to inhibit thrombin amidolytic activity. The results showed that both s-variegin and EP25 lost their activity only after prolonged incubation with thrombin (FIG. 6B-D). Interestingly, at the same temperature (24° C.) and molar ratios (30-fold excess of s-variegin), after 60 min of incubation, ~30% of s-variegin was cleaved, yet no loss of inhibitory activity of s-variegin and EP25 was observed. 24 h of incubation was needed for ~30% loss of inhibitory activity of s-variegin and EP25. In the case of the slow binding inhibition of EP25, percentage inhibition increased with incubation time up to 20 min and then decreased due to cleavage by thrombin (FIG. 6D). Thus, it is likely that the cleavage product(s) retain strong binding to the thrombin active site.

Discussion

Variegin is one of the smallest thrombin inhibitors found in nature. Despite its small size and flexible structure, variegin binds to thrombin with strong affinity. Structure-activity studies indicate that variegin binds over an extended surface area of thrombin. The seven N-terminal residues affected the binding kinetics; when removed, the binding characteristics of variegin changed from fast to slow. Residues 8 to 14 appear to bind to the thrombin active site, and residues 15 to 32 appear to bind to exosite-I. Although variegin is cleaved by thrombin, its inhibitory activity was largely retained after cleavage.

Over the years, many thrombin inhibitors have been isolated from hematophagous animals and snake venom. However, no similarities were found in the primary structure of variegin and other thrombin inhibitors. The absence of cysteines, suggesting a flexible structure, also differs from prototypic thrombin inhibitors such as hirudin (compact N-terminus, acidic and extended C-terminus)[6,11-13], rhodniin (double domain Kazal-type inhibitor)[31,32], ornithodorin (double domain Kunitz-type inhibitor)[33] and theromin (acidic and antitastin-like N-terminus, compact C-terminus)[34], even though they all bind to the same sites on thrombin (active site and exosite-I) (FIG. 7A). Although variegin residues 19 to 28 are almost identical to hirudin C-terminus, their N-termini are completely different (FIG. 7B). Unlike hirudin, variegin is not sulfated at the Tyr residue and has three extra residues at the end. Desulfation of hirudin[24] or its C-terminal peptide (hirugen)[29] retained anti-thrombin activity despite a 10-fold reduction in affinity[24] and activity[29]. Our results indicated that AP18 binds to exosite-I and slightly enhanced thrombin amidolytic activity, comparable to the reported behavior of hirudin C-terminus[28,29], suggesting similar roles for these two sequences. This appears to be an example of convergent evolution in two phylogenetically distant lineages.

Variegin is also distinct from other thrombin inhibitors such as haemadin[35,36], triabin[37,38] and bothrojaracin[39]. Haemadin has a similar structure to hirudin, binding to the thrombin active site with its N-terminus, and to exosite-II with the extended C-terminus[35,36]. Triabin only inhibits exosite-I and has a similar structure to lipocalins[37,38]. Bothrojaracin, a C-type lectin protein, binds to both exosite-I and exosite-II[39]. Only two other thrombin inhibitors of similar size have been reported to date, but they appear to be unrelated to variegin. Despite also having 32 residues, tsetse thrombin inhibitor (TTI), isolated from tsetse fly *Glossina morsitans morsitans*[40,41], does not share any sequence similarity with variegin (FIG. 7A). Another low molecular weight thrombin inhibitor (3.2 kDa) was isolated from the camel tick, *Hyalomma dromedarii* (NTI-1)[42]. Unlike variegin, NTI-1 is a weak ($K_i$=11.7 µM) and non-competitive inhibitor of thrombin, binding to only one site on thrombin (FIG. 7A). Currently, no detailed structural information for NTI-1 is available.

Perhaps variegin is best compared with hirulogs, synthetic thrombin inhibitors designed by grafting the hirudin C-terminus to the active site binding moiety $_D$-Phe-Pro-Arg-Pro through a linker of four Gly residues[14] (FIG. 7A). While development of hirulogs (marketed as bivalirudin) represents successful rational drug design, variegin demonstrates the ability of nature to produce similar 'designs' through evolution. Thus, variegin can be described as a 'natural' hirulog. S-variegin and EP25 have several advantages over hirulogs as thrombin inhibitors. Firstly, variegin and EP25 comprise natural amino acids (hirulogs generally have $_D$-Phe). Secondly, even without Thr glycosylation, their affinity for thrombin is higher than that of hirulog-1. EP25 (comparable to hirulog-1 in length) inhibits thrombin with a much stronger affinity ($K_i$ values of EP25 and hirulog-1 are ~149.8±30.5 pM and ~2500 pM[43] respectively). Lastly, although both hirulogs and variegin are cleaved by thrombin, variegin (and EP25) loses its inhibitory activity towards thrombin at a much slower rate than hirulogs. For example, at an inhibitor to thrombin ratio of 3:1, hirulog-1 lost all inhibitory activity towards thrombin amidolytic activity after ~15 min[43] while s-variegin and EP25 lost >90% inhibitory activity only after 24 h incubation. Thus, variegin and EP25 appear to be superior to hirulogs.

Since the C-termini of hirulogs and variegin are highly similar (FIG. 7A), we propose that the improved affinity and delayed loss of activity of variegin are mainly due to the N-terminus. Our results showed that the active site binding moiety on variegin has the sequence EPKMHKT (SEQ ID NO 19), and thrombin cleaves variegin between K-M. This substrate sequence appears to be different from sequences of most natural substrates of thrombin. For example, Lys at P1, although possible, is very rarely observed[44]. Also, the presence of Glu at P3, Met at S1', His at S2' and glucosylated Thr at P4' are all uncommon[44,45]. Therefore, the identification of this unique active site binding moiety could have strong implications in both understanding thrombin substrate preference and the discovery of new leads for developing direct thrombin inhibitors.

Site-directed mutation and intrinsic fluorescence studies suggest the following events during binding of hirudin to thrombin[25,46]: (1) electrostatic steering due to the complementary electric fields of hirudin C-terminus and thrombin exosite-I, (2) ionic tethering through direct interactions between specific residues of hirudin C-terminus inducing conformational changes and stabilization of the thrombin-hirudin C-terminal complex, and (3) subsequent binding of hirudin N-terminus to the apolar site near the active site. The conformational changes upon binding of hirudin C-terminus (step 2) detected with intrinsic fluorescence studies were observed to be the rate limiting step[46]. Hirudin behaved as a slow binding inhibitor in high ionic strength solution (>0.2 M) where ionic interactions were impaired[24]. Interestingly, in variegin, the deletion of seven N-terminal residues led to a switch from a fast binding inhibitor to a slow binding inhibitor without significant loss of binding affinity. This slow binding observed for EP25 is presumably due to the loss of N-terminal residues instead of impaired ionic tethering observed for hirudin, suggesting a different rate limiting step. The kinetic studies indicate that the slow binding mode of EP25 probably involves isomerization of the thrombin-EP25 complex. We propose that long-range electrostatic interactions between the C-terminus of EP25 and thrombin exosite-I allow rapid formation of initial collision complex (EI). This leads to subsequent binding of EPKMHKT (SEQ ID NO 19) to the active site in a slow step to form the stabilized enzyme-inhibitor complex (EI*) through short range interactions (step 3 is the rate limiting step) (FIG. 7B). By contrast, in the full-length variegin, the N-terminus, possibly through two negatively charged residues in SDQGDVA (SEQ ID NO 18), provides an additional electrostatic steering effect to pre-orientate the N-terminus close to the active site allowing rapid formation of short-range interactions. The electrostatic steering effect of the N-terminus is facilitated by the presence of highly basic exosite-II. Exosite-II is located about 10 Å away from the active site, a distance that can theoretically be covered by the seven N-terminal residues in an extended conformation (FIG. 7C).

In summary, we present the isolation, characterization and structure-function relationships of a potent bivalent thrombin inhibitor, variegin. It is a novel class of thrombin inhibitor and provides an excellent platform for the development of new thrombin inhibitors.

Example 2

Analysis of Activity of Variants and Fragments of Variegin

The assays described above to determine the $IC_{50}$ and $K_i$ of s-variegin and EP25 were repeated as described in Example 1 except that 1.65 nM human plasma derived thrombin (from KAKETSUKEN, Japan) was used, instead of 3.33 nM recombinant human alpha-thrombin (from KAKETSUKEN, Japan).

In these experiments, s-variegin was found to have an $IC_{50}$ of around 9 nM and a $K_i$ or around 0.318 nM. EP25 was found to have an $IC_{50}$ of around 13 nM and a $K_i$ or around 0.365 nM. The reason for the difference between the $IC_{50}$ and $K_i$ values in this experiment compared to the results obtained in Example 1 was identified as being the use of human plasma derived thrombin instead of recombinant human alpha-thrombin.

Experiments were also conducted to assess the $IC_{50}$ and $K_i$ of a variety of variegin fragments and mutants of these fragments, as discussed below, and to compare the $IC_{50}$ and $K_i$ values of these fragments and mutants with the $IC_{50}$ and $K_i$ values of the known thrombin inhibitor hirulog-1 (bivalirudin). All of these experiments were also conducted using human plasma derived thrombin so that the results would be directly comparable.

A summary of these results is presented in Table 3 below.

Analysis of MH22-
MHKTAPPFDFEAIPEEYLDDES

Considering that s-variegin largely retains its activity after cleavage, we hypothesized that the cleavage product(s) remained tightly bond to thrombin. A peptide, MH22, that represents the C-terminal fragment after s-variegin cleavage was synthesized.

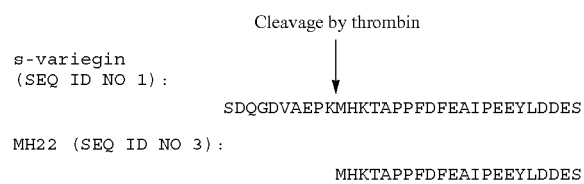

Without any pre-incubation with thrombin, MH22 was found to inhibit thrombin amidolytic activity with an $IC_{50}$ of 11.5±0.71 nM (FIG. 11). No significant change of inhibitory activity was observed when MH22 was pre-incubated with thrombin for a short period of time (10 min pre-incubation $IC_{50}=13.4\pm0.76$ nM; 20 min pre-incubation $IC_{50}=12.3\pm1.89$ nM), indicating that MH22 is fast binding.

MH22 shows decreased amidolytic activity after prolonged incubation with thrombin (1680 min pre-incubation $IC_{50}=479.7\pm16.1$ nM). This lost of activity can be reverted by increasing concentrations of BSA in assays setup (FIG. 12), indicating that activity lost was largely due to absorption of peptides to the reaction plates. With higher concentrations of BSA used, after 1680 min pre-incubation, $IC_{50}$ decreases from $479.7\pm16.1$ nM (1 mg/ml BSA) to $60.9\pm3.05$ nM (5 mg/ml BSA) and $62.9\pm10.9$ nM (10 mg/ml BSA).

The apparent $K_i'$ of MH22 at different concentrations of substrate (S2238) was determined through equation describing fast and tight binding. $K_i'$ did not change significantly throughout the concentration range used (12.5 nM to 200 nM), indicating that MH22 is a non-competitive inhibitor of thrombin amidolytic activity (FIG. 13). For non-competitive inhibitors, $K_i'=K_i$ and in this case the average $K_i$ was found to be $13.2\pm0.91$ nM.

```
                                           (SEQ ID NO 3)
Analysis of EP25A22E - EPKMHKTAPPFDFEEIPEEYLDDES
```

Next, peptide EP25A22E was synthesized. In this peptide, alanine 22 in s-variegin (alanine 15 in EP25) was replaced with glutamic acid since glutamic acid is present in the same position in hirudin.

```
EP25 (SEQ ID NO 6):     EPKMHKTAPPFDFEAIPEEYLDDES
EP25A22E (SEQ ID NO 7): EPKMHKTAPPFDFEEIPEEYLDDES
```

Similar to EP25, EP25A22E is a slow binding inhibitor, with $IC_{50}=124.3\pm22.7$ nM without pre-incubation with thrombin, $IC_{50}=13.5\pm2.08$ nM with 20 min of pre-incubation and $IC_{50}=13.6\pm3.15$ nM (FIG. 14). Compared to EP25, the replacement did not adversely affect the amidolytic activity.

$K_i$ of EP25A22E was determined using the slow binding inhibitor equation and was found to be $0.311\pm0.070$ nM (FIG. 15). Compared to the $K_i$ of EP25, the replacement did not therefore adversely affect binding affinity to thrombin.

```
                                           (SEQ ID NO 5)
Analysis of MH22A22E - MHKTAPPFDFEEIPEEYLDDES
```

The C-terminal fragment of EP25A22E cleavage, represented by peptide MH22A22E was synthesized.

```
EP25A22E (SEQ ID NO 7): EPKMHKTAPPFDFEEIPEEYLDDES
MH22A22E (SEQ ID NO 5):   MHKTAPPFDFEEIPEEYLDDES
```

Similar to MH22, $IC_{50}$ of MH22A22E is $13.6\pm0.45$ nM without pre-incubation with thrombin and $IC_{50}=15.6\pm0.36$ with 20 min pre-incubation (FIG. 16).

Again similar to MH22, MH22A22E has a $K_i'$ of $15.1\pm1.04$ nM when tested with 100 μM of substrate (S2238). Assuming the single residue replacement from alanine to glutamic acid did not alter the inhibition mechanism, MH22A22E is also a non-competitive inhibitor with $K_i=15.1\pm1.04$ nM (FIG. 17).

```
Analysis of EP21 having the sequence
                                           (SEQ ID NO 8)
EPKMHKTAPPFDFEAIPEEYL
and MH18 having the sequence
                                           (SEQ ID NO 20)
MHKTAPPFDFEAIPEEYL
```

Results from both EP25A22E and MH22A22E showed that replacement of alanine 22 with glutamic acid did not alter peptide activities. Next, peptides were synthesized by retaining the alanine residue.

Considering that s-variegin has an additional four residues on the C-terminal when compared to the known thrombin inhibitor hirulog, peptides EP21 and MH18 were synthesized to determine the role of the four additional residues.

```
EP21 (SEQ ID NO 8):   EPKMHKTAPPFDFEAIPEEYL
MH18 (SEQ ID NO 20):    MHKTAPPFDFEAIPEEYL
```

The ability of these two fragments to inhibit thrombin activity was assessed. No significant activity was lost when the four residues were removed. EP21 is also a slow binding inhibitor, with $IC_{50}$ of $176.9\pm6.77$ nM without pre-incubation with thrombin, $IC_{50}=16.2\pm2.93$ nM with 20 min pre-incubation and $IC_{50}=16.20\pm2.93$ nM with 30 min pre-incubation (FIG. 18). $K_i$ of EP21, determined by slow binding equations was found to be $0.315\pm0.024$ nM (FIG. 19).

Similarly, no significant loss of activity was observed for MH18. $IC_{50}=10.9\pm1.20$ nM without pre-incubation with thrombin and $IC_{50}=11.7\pm1.88$ nM with 20 min pre-incubation (FIG. 20).

Using fast and tight binding equation, $K_i'$ of MH18 at 100 μM substrate (S2238)=$14.9\pm3.50$ nM. Assuming the removal of four residues at the C-terminal did not alter the inhibition mechanism, MH18 is also a non-competitive inhibitor with $K_i=14.9\pm3.50$ nM (FIG. 21).

```
Analysis of DV24-
                                           (SEQ ID NO 9)
DVAEPKMHKTAPPFDFEAIPEEYL
```

Since we have postulated that the charged residues in the N-terminal of s-variegin are responsible for its fast binding kinetic, we synthesized a peptide DV24 with three extra residues on the N-terminal of EP21 to test if the peptide will switch to a fast binding mode.

```
EP21 (SEQ ID NO 8):  EPKMHKTAPPFDFEAIPEEYL
DV24 (SEQ ID NO 9):  DVAEPKMHKTAPPFDFEAIPEEYL
```

As predicted, DV24 is a fast and tight binding inhibitor, with $IC_{50}=7.49\pm0.28$ nM without pre-incubation with thrombin and $IC_{50}=10.1\pm0.60$ nM with 20 min pre-incubation (FIG. 22). DV24 is cleaved by thrombin and the activity observed after cleavage is due to the C-terminal fragment of the cleavage product (the fragment is represented by peptide MH18).

Using fast and tight binding equation, $K_i'$ of DV24 at 100 μM substrate (S2238)=$9.74\pm0.91$ nM and $K_i$ of DV24 was determined to be $0.306\pm0.029$ nM, assuming the peptide is a competitive inhibitor (FIG. 23).

```
                                           (SEQ ID NO 10)
Analysis of DV24K10R - DVAEPRMHKTAPPFDFEAIPEEYL
```

Considering most thrombin inhibitors have an arginine at the P1 position instead of lysine in s-variegin, we synthesized a peptide DV24K10R with the same replacement.

```
DV24    (SEQ ID NO 9):      DVAEPKMHKTAPPFDFEAIPEEYL

DV24K10R (SEQ ID NO 10):    DVAEPRMHKTAPPFDFEAIPEEYL
```

Figure 24:
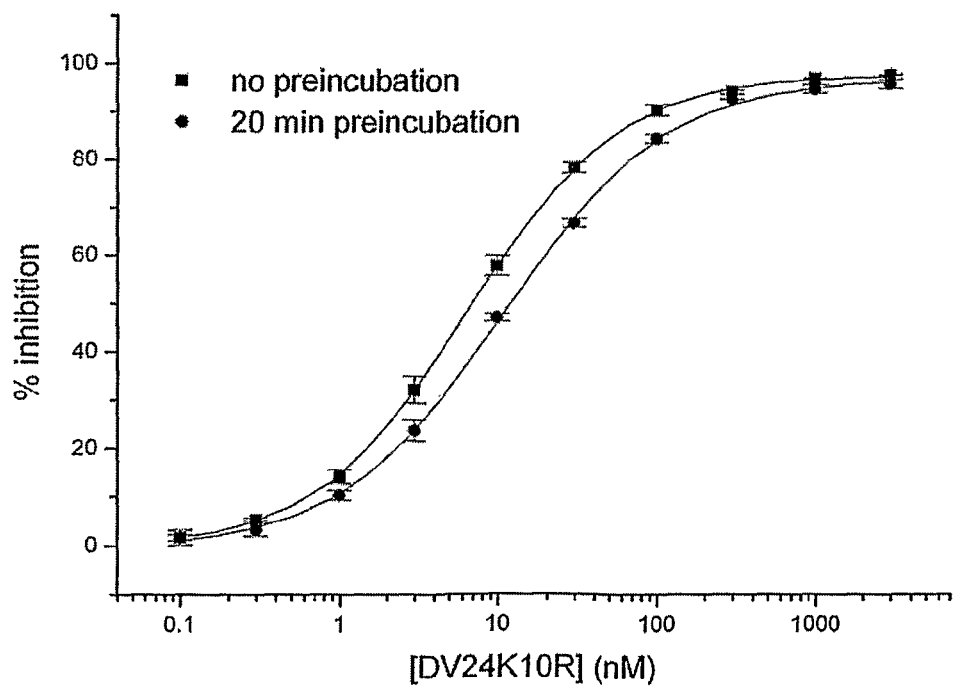

DV24K10R is also a fast and tight binding inhibitor, with $IC_{50}=6.98\pm0.76$ nM without pre-incubation with thrombin and $IC_{50}=12.01\pm0.41$ nM with 20 min pre-incubation (FIG. 24). DV24K10R is also cleaved by thrombin and the activity observed after cleavage is due to the C-terminal fragment of the cleavage product (the fragment is represented by peptide MH18).

Using fast and tight binding equation, $K_i'$ of DV24K10R at 100 μM substrate (S2238)=$8.22\pm0.48$ nM and $K_i$ of DV24K10R is determined to be $0.259\pm0.015$ nM, assuming the peptide is a competitive inhibitor (FIG. 25). Replacement of lysine with arginine thus improves the activity of the fragment.

Conclusion

These experimental results confirm the finding that fragments of variegin and mutants of these fragments are effective inhibitors of thrombin activity. Information resulting from these molecular substitution experiments also confirmed that interaction with exosite 2 is important in conferring the most rapid binding to thrombin.

TABLE 3

Comparison of $IC_{50}$ and $K_i$ values

| Peptide | Sequence | Pre-incubation time (min) | $IC_{50}$ (nM) | $K_i$ (nM) |
|---|---|---|---|---|
| s-variegin | SDQGDVAEPKMHKTAPPF DFEAIPEEYLDDES (SEQ ID NO 1) | 0 | 8.50 ± 0.16 | 0.318 ± 0.020 |
|  |  | 10 | 9.62 ± 0.30 |  |
|  |  | 20 | 10.59 ± 0.30 |  |
|  |  | 30 | 11.54 ± 1.28 |  |
|  |  | 120 | 13.15 ± 1.25 |  |
|  |  | 1080 | 21.79 ± 5.64 |  |
|  |  | 1680 | 504.22 ± 27.98 |  |
|  |  | (1 mg/ml BSA) |  |  |
|  |  | 1680 | 53.41 ± 12.16 |  |
|  |  | (5 mg/ml BSA) |  |  |
|  |  | 1680 | 38.99 ± 0.43 |  |
|  |  | (10 mg/ml BSA) |  |  |
| EP25 | EPKMHKTAPPFDFEAIPEE YLDDES (SEQ ID NO 6) | 0 | 173.13 ± 25.86 | 0.365 ± 0.109 |
|  |  | 10 | 14.09 ± 1.12 |  |
|  |  | 20 | 13.12 ± 0.67 |  |
|  |  | 30 | 13.59 ± 1.34 |  |
|  |  | 120 | 12.43 ± 1.83 |  |
|  |  | 1080 | 26.80 ± 4.09 |  |
|  |  | 1680 | 437.92 ± 4.90 |  |
|  |  | (1 mg/ml BSA) |  |  |
|  |  | 1680 | 39.06 ± 9.37 |  |
|  |  | (5 mg/ml BSA) |  |  |
|  |  | 1680 | 38.43 ± 5.39 |  |
|  |  | (10 mg/ml BSA) |  |  |
| MH22 | MHKTAPPFDFEAIPEEYLD DES (SEQ ID NO 3) | 0 | 11.46 ± 0.71 | 13.16 ± 0.91 |
|  |  | 10 | 13.36 ± 0.76 |  |
|  |  | 20 | 12.34 ± 1.89 |  |
|  |  | 30 | 14.94 ± 0.77 |  |
|  |  | 120 | 14.63 ± 2.32 |  |
|  |  | 1080 | 34.52 ± 4.59 |  |
|  |  | 1680 | 479.74 ± 16.05 |  |
|  |  | (1 mg/ml BSA) |  |  |
|  |  | 1680 | 60.90 ± 3.05 |  |
|  |  | (5 mg/ml BSA) |  |  |
|  |  | 1680 | 62.89 ± 10.90 |  |
|  |  | (10 mg/ml BSA) |  |  |
| Hirulog-1 | $_D$FPRPGGGNGDFEEIPEEYL (SEQ ID NO 23) | 0 | 72.58 ± 3.90 | 2.94 ± 0.12 |
|  |  | 10 | 101.62 ± 12.92 |  |
|  |  | 45 | 133.85 ± 15.78 |  |
|  |  | 120 | 258.77 ± 25.72 |  |
|  |  | (1 mg/ml BSA) |  |  |
|  |  | 120 | 279.72 ± 4.74 |  |
|  |  | (5 mg/ml BSA) |  |  |
|  |  | 120 | 281.84 ± 6.21 |  |
|  |  | (10 mg/ml BSA) |  |  |
| EP25A22E | EPKMHKTAPPFDFEEIPEEY LDDES (SEQ ID NO 7) | 0 | 124.32 ± 22.74 | 0.311 ± 0.070 |
|  |  | 20 | 13.49 ± 2.08 |  |
|  |  | 30 | 13.55 ± 3.15 |  |

TABLE 3-continued

Comparison of IC$_{50}$ and K$_i$ values

| Peptide | Sequence | Pre-incubation time (min) | IC$_{50}$ (nM) | K$_i$ (nM) |
|---|---|---|---|---|
| MH22A22E | MHKTAPPFDFEEIPEEYLDDES (SEQ ID NO 5) | 0<br>20 | 13.62 ± 0.45<br>15.63 ± 0.36 | 15.07 ± 1.04 |
| EP21 | EPKMHKTAPPFDFEAIPEEYL (SEQ ID NO 8) | 0<br>20<br>30 | 176.87 ± 6.77<br>16.20 ± 2.93<br>13.85 ± 1.29 | 0.315 ± 0.024 |
| MH18 | MHKTAPPFDFEAIPEEYL (SEQ ID NO 20) | 0<br>20 | 10.93 ± 1.20<br>11.73 ± 1.88 | 14.94 ± 3.50 |
| DV24 | DVAEPKMHKTAPPFDFEAIPEEYL (SEQ ID NO 9) | 0<br>20 | 7.49 ± 0.28<br>10.07 ± 0.60 | 0.306 ± 0.029 |
| DV24K10R | DVAEPKMHKTAPPFDFEAIPEEYL (SEQ ID NO 10) | 0<br>20 | 6.98 ± 0.76<br>12.01 ± 0.41 | 0.259 ± 0.015 |

Example 3

Quantitative Whole Body Autoradiography Studies in Rats

The distribution of Variegin, was investigated in the rat, using [$^3$H]-labelled test substance. Experiments were conducted at a dose level of 0.4 mg/kg.

Experimental Procedures:

Dose Preparation and Evaluation

A solution of 1 mg of Variegin dissolved in 1 mL of dialysis buffer (50 mM sodium phosphate, 200 mM sodium chloride (pH 8.0)) was prepared and incubated with [$^3$H]-NSP (400 µCi).

The solution was transferred to a dialysis tube (1000 kda) and dialysed for approximately 96 hours the dialysis buffer was changed three times per day. The solution was then loaded onto a NAP5 column (pre-equilibrated with 10 mL buffer solution at pH8) and the eluate discarded. Buffer was then added and the eluate collected to provide a [$^3$H]-labelled protein solution at approximately 0.5 mg/mL.

Aliquots of the [$^3$H]-Variegin solution were removed for radioassay by liquid scintillation counting. Further aliquots of the [$^3$H]-Variegin solution were analysed by HPLC before dosing to confirm efficiency of protein labelling (see FIG. 26).

Dose Administration

Single intravenous doses were administered to each animal using a syringe and needle, by volume, at a dose level of 0.4 mg/kg (0.8 mL/kg bodyweight). The formulation was dispensed as a single pulse dose into a tail vein of the rat. The amount of dose administered to each rat was determined by volume dosed, and the stated radioactive concentration and specific activity of the dose solution.

Pharmacokinetic Study

[$^3$H]-Variegin was administered to three male rats as a single intravenous dose at a nominal dose level of 0.4 mg/kg. Serial blood samples were taken for plasma preparation, at the following times post dose: 0.5, 1, 2, 4, 6, 24 and 48 hours To obtain plasma, samples were centrifuged as soon as possible after collection. Plasma was harvested and an aliquot retained for radioactivity measurement. Blood cells were discarded.

Measurement of Radioactivity

The radioactivity associated with plasma was determined directly by liquid scintillation counting of known volumes of samples. Samples were mixed with Ultima Gold scintillant and counted using a Packard liquid scintillation counter with automatic external standard quench correction. After choosing the optimal channel setting, quench correction curves were prepared from radiochemical standards. The validity of the curves was checked throughout the experiments. Radioactivity with less than twice background counts was considered to be below the limit of accurate quantification.

Pharmacokinetics

The concentration of Variegin in the plasma following intravenous administration was analysed using PCModfit (Version 3.0). The kinetic data was characterised by a non-compartmental analysis (NCA). The following pharmacokinetic parameters were derived from the data: maximum peak plasma blood concentration (C$_{max}$); the time of maximum observed concentration (T$_{max}$); the terminal half-life (t1/2), and the area under the curve (AUC).

The AUC was determined using the linear/log trapezoidal method. A value of zero was used for any plasma concentrations recorded as below the limits of quantification (BLQ).

The AUC$_{inf}$(observed) was calculated as the area under the curve from the time of dosing extrapolated to time infinity based on the observed concentrations. The AUC$_{inf}$ parameter therefore is an extrapolated parameter which gives a more representative estimate of exposure as it contains the additional portion of the time-concentration profile from the last data point to a time (in the future) when the concentration is estimated to be zero.

Tissue Distribution Study

[$^3$H]-Variegin was administered to three male rats as a single intravenous dose at a nominal dose level of 0.4 mg/kg. At 0.5, 1 and 24 hours after dose administration, one rat was killed by CO$_2$ overdose. After sacrifice, the animals were frozen rapidly by total immersion in a bath of hexane cooled to ca. −80° C. with solid carbon dioxide.

Following removal of the whiskers, legs and tail, each frozen carcass was set in a block of 1% (w/v) aqueous carboxymethylcellulose and mounted onto a stage of a Leica CM3600 cryomicrotome maintained at ca. −20° C. Sagittal sections (nominally 30 µm) were then obtained from five levels through the carcass so as to include all major tissues and organs.

Level A: exorbital lachrymal gland
Level B: intra-orbital lachrymal gland
Level C: Harderian gland/adrenal gland
Level D: thyroid
Level E: brain and spinal cord The sections, mounted on autoradiography tape, were placed in contact with FUJI imaging plates (type BAS-III, Raytek Scientific Ltd, Sheffield). These procedures are based on the work of Ullberg (Acta. Radiol. Suppl. 118, 22).

Image Analysis of Whole-Body Autoradiograms

After exposure in a lead container stored in a freezer at ca. −75° C. for at least 14 days, the imaging plates were processed using a FUJI BAS 1500 Bio-image analyser (Raytek Scientific Ltd).

The electronic images were analysed using a validated PC-based image analysis package (SeeScan Densitometry software, LabLogic, Sheffield). A set of [$^3$H]-labelled blood standards were prepared and used to construct calibration lines over a range of radioactivity concentrations.

The lower limit of quantification for this procedure was defined as the lowest quantifiable standard included in the microscale (36.6 nCi/g). Individual tissue concentrations of radioactivity were expressed in nCi/g and converted to pg equivalents Variegin/g (μg equiv/g) using the calculated specific activity of test material in the dose formulation. This gave a lower limit of quantification of 6.83 μg equiv/g.

Wherever possible, the maximum area within a single autoradiograph was defined for each tissue for measurement. For some tissues this was impractical and so one particular region was selected for measurement. These tissues, along with the corresponding areas of measurement, are listed as follows:

| Tissue | Region defined for measurement |
| --- | --- |
| Blood | Heart |
| Bone marrow | Pelvic girdle |
| Brown fat | Hibernating gland |
| Lymph nodes | Mandibular |
| Muscle | Rump |
| Non-pigmented skin | Lower back |
| Stomach mucosa | Non-fundic |
| White fat | Peri-renal area |

Figure 27:
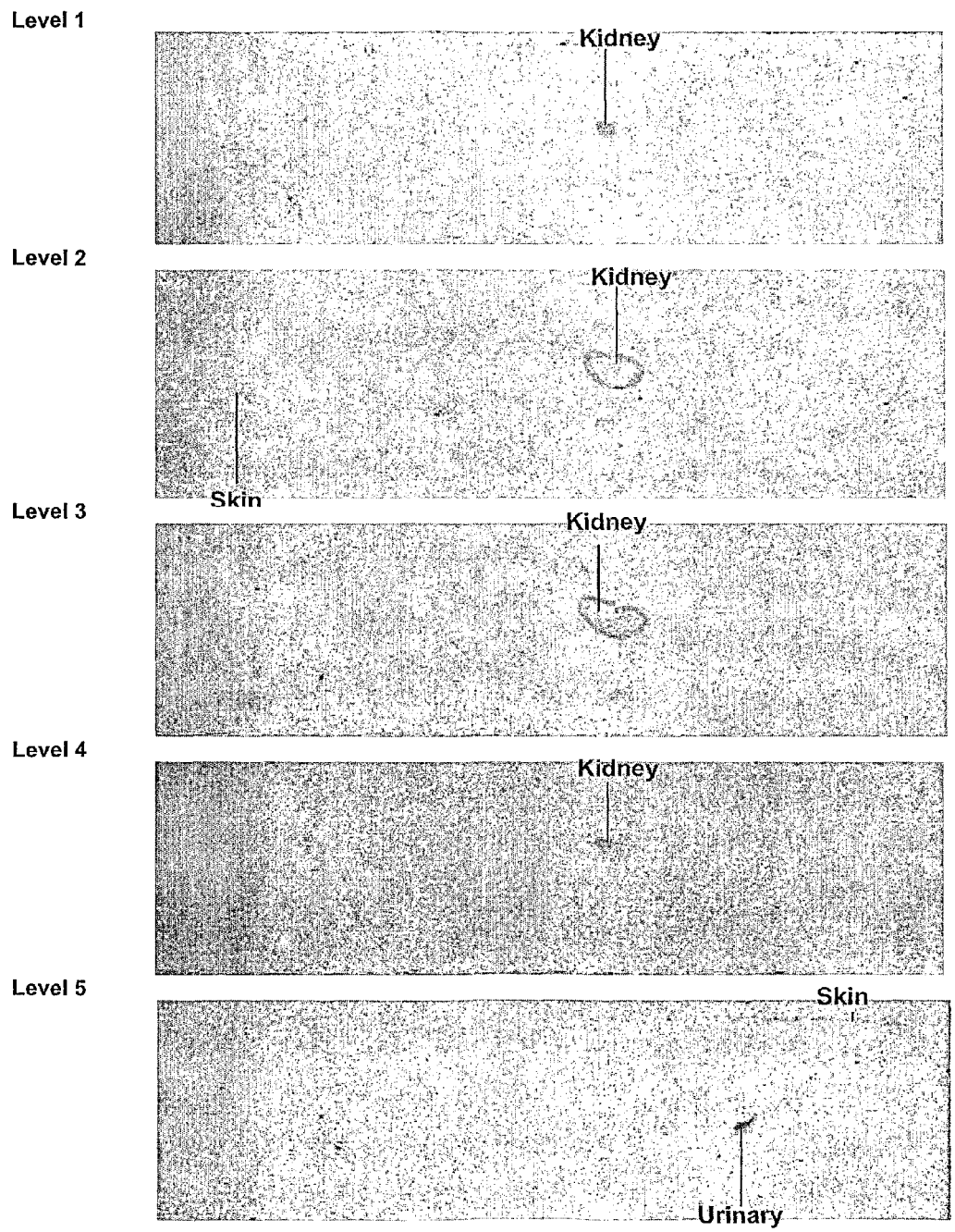

The electronic images of the autoradiograms were used to prepare FIGS. 27-29. Levels 1 to 5 in FIG. 27-29 refer to successive 1 cm longitudinal sections through the rat body.

Results and Discussion

Where concentrations are reported as μg or ng equivalents/g (mL), radioactivity is assumed to be associated with Variegin or with compounds of the same molecular weight. The specific activity of the dose solution was used for the calculation of concentrations (μg or ng equiv/g (mL)) in all cases.

Pharmacokinetic Study:

A summary of the mean pharmacokinetic parameters of total radioactivity observed following intravenous administration of [$^3$H]-Variegin to three male Sprague Dawley rats are given in Tables 4 and 5 below:

TABLE 4

Concentrations of total radioactivity in plasma obtained from male rats after intravenous administration of [$^3$H]-Variegin at a nominal dose level of 0.4 mg/kg

| Time (hours) | 1M | 2M | 3M | Mean (n = 3) | sd |
| --- | --- | --- | --- | --- | --- |
| 0.5 | 425.9 | 540.3 | 441.0 | 469.1 | 62.15 |
| 1 | 245.6 | 316.7 | 260.5 | 274.3 | 37.50 |
| 2 | 127.7 | 139.2 | 144.4 | 137.1 | 8.546 |
| 4 | 92.97 | 104.6 | 100.3 | 99.29 | 5.880 |

TABLE 4-continued

Concentrations of total radioactivity in plasma obtained from male rats after intravenous administration of [$^3$H]-Variegin at a nominal dose level of 0.4 mg/kg

| Time (hours) | 1M | 2M | 3M | Mean (n = 3) | sd |
| --- | --- | --- | --- | --- | --- |
| 6 | 98.61 | 122.6 | 101.4 | 107.5 | 13.12 |
| 24 | 96.47 | 92.32 | 102.2 | 97.00 | 4.961 |
| 48 | 83.17 | 84.89 | 83.62 | 83.89 | 0.892 |

BLD Below Limit of detection (<2x background dpm)
sd standard deviation

Results expressed as ng equivalents/g

TABLE 5

Summary of mean pharmacokinetic parameters (total radioactivity) measured in plasma obtained from male rats following a single intravenous administration of [$^3$H]-variegin.

| Parameter | Total Radioactivity |
| --- | --- |
| $C_{max}$ (ng equiv./g) | 469.1 |
| $T_{max}$ (hours) | 0.5 |
| $AUC_{0-48}$ (ng equiv./g.h) | 4943.4 |
| $AUC_{inf}$ (ng equiv./g.h) | 19147 |
| $t\frac{1}{2}^a$ (hours) | 117.2 |
| $t\frac{1}{2}^b$ (hours) | 0.86 |

$C_{max}$ = maximum plasma concentration
$T_{max}$ = time of maximum plasma concentration
$AUC_{0-48}$ = area under curve from time of dosing to last measurable concentration
$AUC_{inf}$ = area under curve from time of dosing extrapolated to infinity
$t\frac{1}{2}^a$ = apparent terminal elimination half life
$t\frac{1}{2}^b$ = apparent distribution half life Tissue Distribution Study:

The results of the tissue distribution study are shown in Tables 6 and 7 below.

TABLE 6

Concentrations of radioactivity in tissues of male albino rats following a single intravenous administration of [$^3$H]-Variegin at a nominal dose level of 0.4 mg/kg

| Tissue | 0.5 hours | 1 hour | 24 hours |
| --- | --- | --- | --- |
| Kidney | 25.7 | 18.8 | BLQ |
| Kidney cortex | 29.1 | BLQ | BLQ |
| Kidney medulla | 8.15 | BLQ | BLQ |
| Skin (non-pigmented) | 17.0 | BLQ | BLQ |
| Urinary bladder | 63.6 | 43.8 | BLQ |

Results expressed as μg equivalents/g
BLQ Below limit of quantification (<6.83 μg equivalents/g)

TABLE 7

Concentrations of radioactivity measured in tissues of male albino rats following a single intravenous administration of [$^3$H]-Variegin at a nominal dose level of 0.4 mg/kg

| Tissue | Rat 4M 0.5 hours | Rat 5M 1 hour | Rat 6M 24 hours |
| --- | --- | --- | --- |
| Kidney | 137.8 | 101.0 | BLQ |
| Kidney cortex | 156.0 | BLQ | BLQ |
| Kidney medulla | 43.7 | BLQ | BLQ |
| Skin (non-pigmented) | 91.2 | BLQ | BLQ |
| Urinary bladder | 341.0 | 234.5 | BLQ |

Results expressed as nCi/g
BLQ Below limit of quantification (36.6 nCi/g)

At 0.5 hours (the first sampling time point), radioactivity was distributed throughout limited tissues. Concentrations of radioactivity were observed in the kidney (25.7 μg equiv./g), (kidney cortex: 29.1 μg equiv./g and kidney medulla: 8.15 μg equiv./g), skin (17.0 μg equiv./g) and the urinary bladder (63.6 μg equiv./g). All other tissues were at levels below the limit of detection (<6.83 μg equiv./g). At 1 hour, concentrations were observed in the kidney (18.8 μg equiv./g) and the urinary bladder (43.8 μg equiv./g) only. By 24 hours, radioactivity in all tissues had declined to below the limit of detection.

Conclusion:

The results indicate that after dosing, absorbed radioactivity was distributed throughout limited tissues. Radioactivity concentrations in the brain were at levels below the limit of quantification at all time points, which would suggest that there is no transfer of test compound across the blood-brain barrier. Maximal concentrations in tissues were observed at 0.5 hours, the first sampling time point. Greatest concentrations of radioactivity were observed in the kidney and urinary bladder. After 24 hours, radioactivity in all tissues had declined to below the limit of detection.

These data indicate that [$^3$H]-Variegin is eliminated very rapidly from the rat. The data obtained is also consistent with the published behaviour of hirudin in the rat where 80% of the radioactivity was recovered in the kidney (Bichler, Baynes and Thorpe, Biochem J (1993) 296, 771-776).

These studies thus confirm that variegin, like other small peptide anti-thrombin agents such as bivalirudin, is rapidly excreted by the renal route. This property makes it suitable for short-term intravenous anticoagulation during surgical procedures. Since direct thrombin inhibitors, unlike heparin which is an indirect thrombin inhibitor, cannot be reversed by the use of vitamin K, having a short half-life is an advantage as in the event of haemorrhage the drug will be eliminated rapidly making other measures to remove residual drug such as ultrafiltration or dialysis less necessary. If prolonged anticoagulation is needed the drug can be administered by continuous intravenous infusion but on cessation, assuming normal renal function, almost all residual drug will be cleared in a period of between 1 and 2 hours. For short procedures such as coronary arthroplasty which typically last about 30 minutes a single bolus injection should provide adequate cover and be eliminated without the need for reversal.

REFERENCES (1) Huntington J A. Molecular recognition mechanisms of thrombin. J Thromb Haemost. 2005; 3:1861-1872.
(2) Di Cera E. Thrombin interactions. Chest. 2003; 124:11S-17S.
(3) Davie E W, Fujikawa K, Kisiel W. The coagulation cascade: initiation, maintenance, and regulation. Biochemistry. 1991; 30:10363-10370.
(4) Davie E W. A brief historical review of the waterfall/cascade of blood coagulation. J Biol Chem. 2003; 278: 50819-50832.
(5) Lane D A, Philippou H, Huntington J A. Directing thrombin. Blood. 2005; 106:2605-2612.
(6) Schwienhorst A. Direct thrombin inhibitors—a survey of recent developments. Cell Mol Life Sci. 2006; 63:2773-2791.
(7) Hirsh J, O'Donnell M, Weitz J I. New anticoagulants. Blood. 2005; 105:453-463.
(8) Gurm H S, Bhatt D L. Thrombin, an ideal target for pharmacological inhibition: a review of direct thrombin inhibitors. Am Heart J. 2005; 149:S43-S53.
(9) Bates S M, Weitz J I. The status of new anticoagulants. Br J Haematol. 2006; 134:3-19.
(10) Markwardt F. The development of hirudin as an antithrombotic drug. Thromb Res. 1994; 74:1-23.
(11) Grutter M G, Priestle J P, Rahuel J et al. Crystal structure of the thrombin-hirudin complex: a novel mode of serine protease inhibition. EMBO J. 1990; 9:2361-2365.
(12) Rydel T J, Ravichandran K G, Tulinsky A et al. The structure of a complex of recombinant hirudin and human alpha-thrombin. Science. 1990; 249:277-280.
(13) Rydel T J, Tulinsky A, Bode W, Huber R. Refined structure of the hirudin-thrombin complex. J Mol Biol. 1991; 221:583-601.
(14) Maraganore J M, Bourdon P, Jablonski J, Ramachandran K L, Fenton J W. Design and characterization of hirulogs: a novel class of bivalent peptide inhibitors of thrombin. Biochemistry. 1990; 29:7095-7101.
(15) Skrzypczak-Jankun E, Carperos V E, Ravichandran K G et al. Structure of the hirugen and hirulog 1 complexes of alpha-thrombin. J Mol Biol. 1991; 221:1379-1393.
(16) Champagne D E. Antihemostatic molecules from saliva of blood-feeding arthropods. Pathophysiol Haemost Thromb. 2005; 34:221-227.
(17) Mans B J, Neitz A W. Adaptation of ticks to a blood-feeding environment: evolution from a functional perspective. Insect Biochem Mol Biol. 2004; 34:1-17.
(18) Kazimirova M, Sulanova M, Trimnellt A R et al. Anticoagulant activities in salivary glands of tabanid flies. Med Vet Entomol. 2002; 16:301-309.
(19) Subburaju S, Kini R M. Isolation and purification of superbins I and II from *Austrelaps superbus* (copperhead) snake venom and their anticoagulant and antiplatelet effects. Toxicon. 1997; 35:1239-1250.
(20) Banerjee Y, Mizuguchi J, Iwanaga S, Kini R M. Hemextin AB complex, a unique anticoagulant protein complex from *Hemachatus haemachatus* (African Ringhals cobra) venom that inhibits clot initiation and factor VIIa activity. J Biol Chem. 2005; 280:42601-42611.
(21) Soejima K, Mimura N, Yonemura H et al. An efficient refolding method for the preparation of recombinant human prethrombin-2 and characterization of the recombinant-derived alpha-thrombin. J Biochem (Tokyo). 2001; 130:269-277.
(22) Yonemura H, Imamura T, Soejima K et al. Preparation of recombinant alpha-thrombin: high-level expression of recombinant human prethrombin-2 and its activation by recombinant ecarin. J Biochem (Tokyo). 2004; 135:577-582.
(23) Kazimirova M, Jancinova V, Petrikova M et al. An inhibitor of thrombin-stimulated blood platelet aggregation from the salivary glands of the hard tick *Amblyomma variegatum* (Acari: Ixodidae). Exp Appl Acarol. 2002; 28:97-105.
(24) Stone S R, Hofsteenge J. Kinetics of the inhibition of thrombin by hirudin. Biochemistry. 1986; 25:4622-4628.
(25) Myles T, Le Bonniec B F, Betz A, Stone S R. Electrostatic steering and ionic tethering in the formation of thrombin-hirudin complexes: the role of the thrombin anion-binding exosite-I. Biochemistry. 2001; 40:4972-4979.
(26) Morrison J F, Walsh C T. The behavior and significance of slow-binding enzyme inhibitors. Adv Enzymol Relat Areas Mol Biol. 1988; 61:201-301.
(27) Rezaie A R. Kinetics of factor Xa inhibition by recombinant tick anticoagulant peptide: both active site and exosite interactions are required for a slow- and tight-binding inhibition mechanism. Biochemistry. 2004; 43:3368-3375.

(28) Naski M C, Fenton J W, Maraganore J M, Olson S T, Shafer J A. The COOH-terminal domain of hirudin. An exosite-directed competitive inhibitor of the action of alpha-thrombin on fibrinogen. J Biol Chem. 1990; 265: 13484-13489.

(29) Maraganore J M, Chao B, Joseph M L, Jablonski J, Ramachandran K L. Anticoagulant activity of synthetic hirudin peptides. J Biol Chem. 1989; 264:8692-8698.

(30) Bode W, Huber R. Natural protein proteinase inhibitors and their interaction with proteinases. Eur J Biochem. 1992; 204:433-451.

(31) Friedrich T, Kroger B, Bialojan S et al. A Kazal-type inhibitor with thrombin specificity from *Rhodnius prolixus*. J Biol Chem. 1993; 268:16216-16222.

(32) van de L A, Lamba D, Bauer M et al. Two heads are better than one: crystal structure of the insect derived double domain Kazal inhibitor rhodniin in complex with thrombin. EMBO J. 1995; 14:5149-5157.

(33) van de L A, Stubbs M T, Bode W et al. The ornithodorin-thrombin crystal structure, a key to the TAP enigma? EMBO J. 1996; 15:6011-6017.

(34) Salzet M, Chopin V, Baert J, Matias I, Malecha J. Theromin, a novel leech thrombin inhibitor. J Biol Chem. 2000; 275:30774-30780.

(35) Strube K H, Kroger B, Bialojan S, Otte M, Dodt J. Isolation, sequence analysis, and cloning of haemadin. An anticoagulant peptide from the Indian leech. J Biol Chem. 1993; 268:8590-8595.

(36) Richardson J L, Kroger B, Hoeffken W et al. Crystal structure of the human alpha-thrombin-haemadin complex: an exosite II-binding inhibitor. EMBO J. 2000; 19:5650-5660.

(37) Fuentes-Prior P, Noeske-Jungblut C, Donner P et al. Structure of the thrombin complex with triabin, a lipocalin-like exosite-binding inhibitor derived from a triatomine bug. Proc Natl Acad Sci USA. 1997; 94:11845-11850.

(38) Noeske-Jungblut C, Haendler B, Donner P et al. Triabin, a highly potent exosite inhibitor of thrombin. J Biol Chem. 1995; 270:28629-28634.

(39) Zingali R B, Jandrot-Perrus M, Guillin M C, Bon C. Bothrojaracin, a new thrombin inhibitor isolated from *Bothrops jararaca* venom: characterization and mechanism of thrombin inhibition. Biochemistry. 1993; 32:10794-10802.

(40) Cappello M, Bergum P W, Vlasuk G P et al. Isolation and characterization of the tsetse thrombin inhibitor: a potent antithrombotic peptide from the saliva of *Glossina morsitans* morsitans. Am J Trop Med Hyg. 1996; 54:475-480.

(41) Cappello M, Li S, Chen X et al. Tsetse thrombin inhibitor: bloodmeal-induced expression of an anticoagulant in salivary glands and gut tissue of *Glossina morsitans* morsitans. Proc Natl Acad Sci USA. 1998; 95:14290-14295.

(42) Ibrahim M A, Ghazy A H, Maharem T, Khalil M. Isolation and properties of two forms of thrombin inhibitor from the nymphs of the camel tick *Hyalomma dromedarii* (Acari: Ixodidae). Exp Appl Acarol. 2001; 25:675-698.

(43) Witting J I, Bourdon P, Brezniak D V, Maraganore J M, Fenton J W. Thrombin-specific inhibition by and slow cleavage of hirulog-1. Biochem J. 1992; 283 (Pt 3):737-743.

(44) Page M J, Macgillivray R T, Di Cera E. Determinants of specificity in coagulation proteases. J Thromb Haemost. 2005; 3:2401-2408.

(45) Bode W, Turk D, Karshikov A. The refined 1.9-A X-ray crystal structure of D-Phe-Pro-Arg chloromethylketone-inhibited human alpha-thrombin: structure analysis, overall structure, electrostatic properties, detailed active-site geometry, and structure-function relationships. Protein Sci. 1992; 1:426-471.

(46) Jackman M P, Parry M A, Hofsteenge J, Stone S R. Intrinsic fluorescence changes and rapid kinetics of the reaction of thrombin with hirudin. J Biol Chem. 1992; 267:15375-15383.

The invention claimed is:

1. A thrombin inhibitor, wherein said thrombin inhibitor consists of a PEGylated form of an amino acid sequence selected from the group consisting of:

```
                                               (SEQ ID NO 6)
EPKMHKTAPPFDFEAIPEEYLDDES (EP25-interaction with
active site and exosite I);

(SEQ ID NO 16)
APPFDFEAIPEEYLDDES (AP18 - exosite I);

(SEQ ID NO 17)
SDQGDVAEPKMHKT (exosite II and active site);

(SEQ ID NO 18)
SDQGDVA (exosite II);

(SEQ ID NO 19)
EPKMHKT (active site);

(SEQ ID NO 2)
SDQGDVAEPK (cleavage product 1);

(SEQ ID NO 3)
MHKTAPPFDFEAIPEEYLDDES (cleavage product 2; MH22);

(SEQ ID NO 11)
SDQGDVAEPKMHKTAPPFDFEAIPEEYL;

(SEQ ID NO 12)
SDQADRAQPKLHRNAPQGDFEAIPDEYL;

(SEQ ID NO 13)
SDQSGRAQPKLPRNAPQGDFEAIPDEYL;

(SEQ ID NO 14)
SDQGDVAEPKMHKTAPPGDFEAIPEEYLD;
and (SEQ ID NO 15)
SDQADVAEPKMHKTAPPGDFEAIPEEYLD.
```

2. The thrombin inhibitor according to claim 1 that consists of a PEGylated form of an amino acid sequence selected from the group consisting of:

```
                                               (SEQ ID NO 6)
EPKMHKTAPPFDFEAIPEEYLDDES (EP25);

(SEQ ID NO 16)
APPFDFEAIPEEYLDDES (AP18);

(SEQ ID NO 18)
SDQGDVA (exosite II);

(SEQ ID NO 19)
EPKMHKT (active site);

(SEQ ID NO 16)
APPFDFEAIPEEYLDDES (exosite I);

(SEQ ID NO 2)
SDQGDVAEPK (cleavage product 1);

(SEQ ID NO 3)
MHKTAPPFDFEAIPEEYLDDES (cleavage product 2);

(SEQ ID NO 20)
MHKTAPPFDFEAIPEEYL (MH18);
and (SEQ ID NO 9)
DVAEPKMHKTAPPFDFEAIPEEYL (DV24).
```

3. A thrombin inhibitor, wherein said thrombin inhibitor consists of a PEGylated form of an amino acid sequence selected from the group consisting of:

```
                                               (SEQ ID NO 9)
DVAEPKMHKTAPPFDFEAIPEEYL (DV24);

(SEQ ID NO 8)
EPKMHKTAPPFDFEAIPEEYL (EP21);

(SEQ ID NO 20)
MHKTAPPFDFEAIPEEYL (MH18);

(SEQ ID NO 7)
EPKMHKTAPPFDFEEIPEEYLDDES (EP25A22E);

(SEQ ID NO 10)
DVAEPRMHKTAPPFDFEAIPEEYL (DV24K10R);
and (SEQ ID NO 5)
MHKTAPPFDFEEIPEEYLDDES (MH22A22E).
```

4. The thrombin inhibitor according to claim 1 that consists of a PEGylated form of an amino acid sequence selected from the group consisting of:

```
                                               (SEQ ID NO 7)
EPKMHKTAPPFDFEEIPEEYLDDES (EP25A22E);

(SEQ ID NO 10)
DVAEPRMHKTAPPFDFEAIPEEYL (DV24K10R);
and (SEQ ID NO 5)
MHKTAPPFDFEEIPEEYLDDES (MH22A22E).
```

5. A thrombin inhibitor, wherein said thrombin inhibitor consists of an amino acid sequence selected from the group consisting of:

```
                                              (SEQ ID NO 12)
SDQADRAQPKLHRNAPQGDFEAIPDEYL;

(SEQ ID NO 13)
SDQSGRAQPKLPRNAPQGDFEAIPDEYL;

(SEQ ID NO 14)
SDQGDVAEPKMHKTAPPGDFEAIPEEYLD;

(SEQ ID NO 15)
SDQADVAEPKMHKTAPPGDFEAIPEEYLD;

(SEQ ID NO 7)
EPKMHKTAPPFDFEEIPEEYLDDES (EP25A22E);
```

-continued

```
                                         (SEQ ID NO 10)
DVAEPRMHKTAPPFDFEAIPEEYL (DV24K10R);
and (SEQ ID NO 5)
MHKTAPPFDFEEIPEEYLDDES (MH22A22E)
``` or is a functional equivalent of SEQ ID NO: 5, 7, 10, 14 or 15 wherein said functional equivalent is modified by glycosylation at threonine.

6. A complex of thrombin and a thrombin inhibitor according to any one of claims 1 to 4 5, and 3.

7. A pharmaceutical composition comprising a thrombin inhibitor according to any one of claims 1 to 4 5, and 3 and a pharmaceutically acceptable carrier.

8. A method of treating Trousseau's syndrome comprising administering to a patient in need thereof a thrombin inhibitor according to any one of claims 1 to 4, 5, and 3 in a therapeutically effective amount.

9. A method of inhibiting thrombin activity by exposing thrombin to the thrombin inhibitor of claim 1, 5, or 3.

10. The method according to claim 9, wherein said method is conducted in vitro.

11. The method according to claim 9, wherein said method is conducted in vivo.

* * * * *

UNITED STATES PATENT AND TRADEMARK OFFICE
CERTIFICATE OF CORRECTION

PATENT NO.         : 9,217,027 B2
APPLICATION NO.    : 12/665256
DATED              : December 22, 2015
INVENTOR(S)        : Maria Kazimirova et al.

Page 1 of 1

It is certified that error appears in the above-identified patent and that said Letters Patent is hereby corrected as shown below:

Title page

Item 12, line number 2, Applicant respectfully requests the first named inventor be corrected as follows:

"Kazimtrova et al." to -- Kazimirova et al. --

Item 75, line number 1, Applicant respectfully requests the first named inventor be corrected as follows:

"Maria Kazimtrova" to -- Maria Kazimirova --

Signed and Sealed this
Second Day of August, 2016

Michelle K. Lee
*Director of the United States Patent and Trademark Office*

SEQUENCE LISTING

```
<160> NUMBER OF SEQ ID NOS: 23

<210> SEQ ID NO 1
<211> LENGTH: 32
<212> TYPE: PRT
<213> ORGANISM: Artificial Sequence
<220> FEATURE:
<223> OTHER INFORMATION: Thrombin inhibitor fragment

<400> SEQUENCE: 1

Ser Asp Gln Gly Asp Val Ala Glu Pro Lys Met His Lys Thr Ala Pro
1               5                   10                  15

Pro Phe Asp Phe Glu Ala Ile Pro Glu Glu Tyr Leu Asp Asp Glu Ser
            20                  25                  30

<210> SEQ ID NO 2
<211> LENGTH: 10
<212> TYPE: PRT
<213> ORGANISM: Artificial Sequence
<220> FEATURE:
<223> OTHER INFORMATION: Thrombin inhibitor fragment

<400> SEQUENCE: 2

Ser Asp Gln Gly Asp Val Ala Glu Pro Lys
1               5                   10
```

```
<210> SEQ ID NO 3
<211> LENGTH: 22
<212> TYPE: PRT
<213> ORGANISM: Artificial Sequence
<220> FEATURE:
<223> OTHER INFORMATION: Thrombin inhibitor fragment

<400> SEQUENCE: 3

Met His Lys Thr Ala Pro Pro Phe Asp Phe Glu Ala Ile Pro Glu Glu
1               5                   10                  15

Tyr Leu Asp Asp Glu Ser
            20

<210> SEQ ID NO 4
<211> LENGTH: 32
<212> TYPE: PRT
<213> ORGANISM: Artificial Sequence
<220> FEATURE:
<223> OTHER INFORMATION: Thrombin inhibitor fragment

<400> SEQUENCE: 4

Ser Asp Gln Gly Asp Val Ala Glu Pro Lys Met His Lys Thr Ala Pro
1               5                   10                  15

Pro Phe Asp Phe Glu Ala Ile Pro Glu Glu Tyr Leu Asp Asp His Ser
            20                  25                  30

<210> SEQ ID NO 5
<211> LENGTH: 22
<212> TYPE: PRT
<213> ORGANISM: Artificial Sequence
<220> FEATURE:
<223> OTHER INFORMATION: Thrombin inhibitor fragment

<400> SEQUENCE: 5

Met His Lys Thr Ala Pro Pro Phe Asp Phe Glu Glu Ile Pro Glu Glu
1               5                   10                  15

Tyr Leu Asp Asp Glu Ser
            20

<210> SEQ ID NO 6
<211> LENGTH: 25
<212> TYPE: PRT
<213> ORGANISM: Artificial Sequence
<220> FEATURE:
<223> OTHER INFORMATION: Thrombin inhibitor fragment

<400> SEQUENCE: 6

Glu Pro Lys Met His Lys Thr Ala Pro Pro Phe Asp Phe Glu Ala Ile
1               5                   10                  15

Pro Glu Glu Tyr Leu Asp Asp Glu Ser
            20                  25

<210> SEQ ID NO 7
<211> LENGTH: 25
<212> TYPE: PRT
<213> ORGANISM: Artificial Sequence
<220> FEATURE:
<223> OTHER INFORMATION: Thrombin inhibitor fragment

<400> SEQUENCE: 7

Glu Pro Lys Met His Lys Thr Ala Pro Pro Phe Asp Phe Glu Glu Ile
1               5                   10                  15

Pro Glu Glu Tyr Leu Asp Asp Glu Ser
            20                  25
```

<210> SEQ ID NO 8
<211> LENGTH: 21
<212> TYPE: PRT
<213> ORGANISM: Artificial Sequence
<220> FEATURE:
<223> OTHER INFORMATION: Thrombin inhibitor fragment

<400> SEQUENCE: 8

Glu Pro Lys Met His Lys Thr Ala Pro Pro Phe Asp Phe Glu Ala Ile
1               5                   10                  15

Pro Glu Glu Tyr Leu
            20

<210> SEQ ID NO 9
<211> LENGTH: 24
<212> TYPE: PRT
<213> ORGANISM: Artificial Sequence
<220> FEATURE:
<223> OTHER INFORMATION: Thrombin inhibitor fragment

<400> SEQUENCE: 9

Asp Val Ala Glu Pro Lys Met His Lys Thr Ala Pro Pro Phe Asp Phe
1               5                   10                  15

Glu Ala Ile Pro Glu Glu Tyr Leu
            20

<210> SEQ ID NO 10
<211> LENGTH: 24
<212> TYPE: PRT
<213> ORGANISM: Artificial Sequence
<220> FEATURE:
<223> OTHER INFORMATION: Thrombin inhibitor fragment

<400> SEQUENCE: 10

Asp Val Ala Glu Pro Arg Met His Lys Thr Ala Pro Pro Phe Asp Phe
1               5                   10                  15

Glu Ala Ile Pro Glu Glu Tyr Leu
            20

<210> SEQ ID NO 11
<211> LENGTH: 28
<212> TYPE: PRT
<213> ORGANISM: Artificial Sequence
<220> FEATURE:
<223> OTHER INFORMATION: Thrombin inhibitor fragment

<400> SEQUENCE: 11

Ser Asp Gln Gly Asp Val Ala Glu Pro Lys Met His Lys Thr Ala Pro
1               5                   10                  15

Pro Phe Asp Phe Glu Ala Ile Pro Glu Glu Tyr Leu
            20                  25

<210> SEQ ID NO 12
<211> LENGTH: 28
<212> TYPE: PRT
<213> ORGANISM: Artificial Sequence
<220> FEATURE:
<223> OTHER INFORMATION: Thrombin inhibitor fragment

<400> SEQUENCE: 12

Ser Asp Gln Ala Asp Arg Ala Gln Pro Lys Leu His Arg Asn Ala Pro
1               5                   10                  15

Gln Gly Asp Phe Glu Ala Ile Pro Asp Glu Tyr Leu
            20                  25

<210> SEQ ID NO 13
<211> LENGTH: 28
<212> TYPE: PRT
<213> ORGANISM: Artificial Sequence
<220> FEATURE:
<223> OTHER INFORMATION: Thrombin inhibitor fragment

<400> SEQUENCE: 13

Ser Asp Gln Ser Gly Arg Ala Gln Pro Lys Leu Pro Arg Asn Ala Pro
1               5                   10                  15

Gln Gly Asp Phe Glu Ala Ile Pro Asp Glu Tyr Leu
            20                  25

<210> SEQ ID NO 14
<211> LENGTH: 29
<212> TYPE: PRT
<213> ORGANISM: Artificial Sequence
<220> FEATURE:
<223> OTHER INFORMATION: Thrombin inhibitor fragment

<400> SEQUENCE: 14

Ser Asp Gln Gly Asp Val Ala Glu Pro Lys Met His Lys Thr Ala Pro
1               5                   10                  15

Pro Gly Asp Phe Glu Ala Ile Pro Glu Glu Tyr Leu Asp
            20                  25

<210> SEQ ID NO 15
<211> LENGTH: 29
<212> TYPE: PRT
<213> ORGANISM: Artificial Sequence
<220> FEATURE:
<223> OTHER INFORMATION: Thrombin inhibitor fragment

<400> SEQUENCE: 15

Ser Asp Gln Ala Asp Val Ala Glu Pro Lys Met His Lys Thr Ala Pro
1               5                   10                  15

Pro Gly Asp Phe Glu Ala Ile Pro Glu Glu Tyr Leu Asp
            20                  25

<210> SEQ ID NO 16
<211> LENGTH: 18
<212> TYPE: PRT
<213> ORGANISM: Artificial Sequence
<220> FEATURE:
<223> OTHER INFORMATION: Thrombin inhibitor fragment

<400> SEQUENCE: 16

Ala Pro Pro Phe Asp Phe Glu Ala Ile Pro Glu Glu Tyr Leu Asp Asp
1               5                   10                  15

Glu Ser

<210> SEQ ID NO 17
<211> LENGTH: 14
<212> TYPE: PRT
<213> ORGANISM: Artificial Sequence
<220> FEATURE:
<223> OTHER INFORMATION: Thrombin inhibitor fragment

<400> SEQUENCE: 17

Ser Asp Gln Gly Asp Val Ala Glu Pro Lys Met His Lys Thr
1               5                   10

<210> SEQ ID NO 18

```
<211> LENGTH: 7
<212> TYPE: PRT
<213> ORGANISM: Artificial Sequence
<220> FEATURE:
<223> OTHER INFORMATION: Thrombin inhibitor fragment

<400> SEQUENCE: 18

Ser Asp Gln Gly Asp Val Ala
1               5

<210> SEQ ID NO 19
<211> LENGTH: 7
<212> TYPE: PRT
<213> ORGANISM: Artificial Sequence
<220> FEATURE:
<223> OTHER INFORMATION: Thrombin inhibitor fragment

<400> SEQUENCE: 19

Glu Pro Lys Met His Lys Thr
1               5

<210> SEQ ID NO 20
<211> LENGTH: 18
<212> TYPE: PRT
<213> ORGANISM: Artificial Sequence
<220> FEATURE:
<223> OTHER INFORMATION: Thrombin inhibitor fragment

<400> SEQUENCE: 20

Met His Lys Thr Ala Pro Pro Phe Asp Phe Glu Ala Ile Pro Glu
1               5                   10                  15

Glu Tyr Leu

<210> SEQ ID NO 21
<211> LENGTH: 10
<212> TYPE: PRT
<213> ORGANISM: Amblyomma variegatum
<220> FEATURE:
<223> OTHER INFORMATION: Vagarin C-terminal fragment

<400> SEQUENCE: 21

Asp Phe Glu Ala Ile Pro Glu Glu Tyr Leu
1               5                   10

<210> SEQ ID NO 22
<211> LENGTH: 10
<212> TYPE: PRT
<213> ORGANISM: Amblyomma variegatum
<220> FEATURE:
<223> OTHER INFORMATION: Hirudin C-terminal fragment

<400> SEQUENCE: 22

Asp Phe Glu Glu Ile Pro Glu Glu Tyr Leu
1               5                   10

<210> SEQ ID NO 23
<211> LENGTH: 20
<212> TYPE: PRT
<213> ORGANISM: Artificial Sequence
<220> FEATURE:
<223> OTHER INFORMATION: Hirudin homolog fragment
<220> FEATURE:
<221> NAME/KEY: Site
<222> LOCATION: 1
<223> OTHER INFORMATION: Phe is a D amino acid

<400> SEQUENCE: 23
```

```
Phe Pro Arg Pro Gly Gly Gly Gly Asn Gly Asp Phe Glu Glu Ile
1               5                   10                  15

Pro Glu Glu Tyr Leu
            20
```